United States Patent
Cragg et al.

(10) Patent No.: US 7,547,324 B2
(45) Date of Patent: Jun. 16, 2009

(54) SPINAL MOBILITY PRESERVATION APPARATUS HAVING AN EXPANDABLE MEMBRANE

(75) Inventors: Andrew H. Cragg, Edina, MN (US); Robert L. Assell, Wilmington, NC (US); Stephen D. Ainsworth, Wilmington, NC (US); Eugene A. Dickhudt, St. Paul, MN (US); Bradley J. Wessman, Wilmington, NC (US)

(73) Assignee: TranS1, Inc., Wilmington, NC (US)

( * ) Notice: Subject to any disclaimer, the term of this patent is extended or adjusted under 35 U.S.C. 154(b) by 386 days.

(21) Appl. No.: 10/972,176

(22) Filed: Oct. 22, 2004

(65) Prior Publication Data

US 2005/0149191 A1   Jul. 7, 2005

Related U.S. Application Data

(63) Continuation of application No. 10/309,416, filed on Dec. 3, 2002, now Pat. No. 6,921,403, which is a continuation-in-part of application No. 10/125,771, filed on Apr. 18, 2002, now Pat. No. 6,899,716, which is a continuation-in-part of application No. 09/848,556, filed on May 3, 2001, now Pat. No. 7,014,633, which is a continuation-in-part of application No. 09/782,583, filed on Feb. 13, 2001, now Pat. No. 6,588,390.

(60) Provisional application No. 60/558,069, filed on Mar. 31, 2004, provisional application No. 60/513,899, filed on Oct. 23, 2003, provisional application No. 60/182,748, filed on Feb. 16, 2000.

(51) Int. Cl.
*A61F 2/44* (2006.01)

(52) U.S. Cl. ............................................. 623/17.11

(58) Field of Classification Search .................. 411/19, 411/383, 384, 392; 604/96.01; 606/61, 72–73; 623/17.11–17.16
See application file for complete search history.

(56) References Cited

U.S. PATENT DOCUMENTS

| | | | |
|---|---|---|---|
| 2,586,556 A | * | 2/1952 | Mullikin ..................... 411/339 |
| 3,367,326 A | | 2/1968 | Frazier |
| 3,837,347 A | * | 9/1974 | Tower ........................ 607/128 |

(Continued)

FOREIGN PATENT DOCUMENTS

EP   1 330 987 B1   7/2003

(Continued)

*Primary Examiner*—Eduardo C Robert
*Assistant Examiner*—Nicholas Woodall
(74) *Attorney, Agent, or Firm*—Kevin W. Cyr; Cyr & Assocaites, P.A.

(57) ABSTRACT

A spinal mobility preservation apparatus and methods are disclosed. The spinal mobility preservation apparatus may include a proximal body, an intermediate body, a distal body, and an expandable membrane. The proximal body and the distal body secure the mobility preservation apparatus to adjacent vertebral bodies. At least one of an intermediate body and an expandable membrane secure the proximal body to the distal body and provide a degree of support to a spinal motion segment defined by the adjacent vertebral bodies. A single proximal body and an expandable membrane may also compose a spinal mobility preservation apparatus. The proximal body secured to one of a superior or an inferior vertebral body and the expandable membrane extending into the intervertebral disc space to support the spinal motion segment.

8 Claims, 13 Drawing Sheets

U.S. PATENT DOCUMENTS

| | | | |
|---|---|---|---|
| 3,867,728 A | 2/1975 | Stubstad et al. | |
| 3,875,595 A | 4/1975 | Froning | |
| 4,276,874 A * | 7/1981 | Wolvek et al. | 600/18 |
| 4,309,777 A | 1/1982 | Patil | |
| 4,446,578 A | 5/1984 | Perkins et al. | |
| 4,858,601 A | 8/1989 | Glisson | |
| 4,874,389 A | 10/1989 | Downey | |
| 5,002,576 A * | 3/1991 | Fuhrmann et al. | 623/17.15 |
| 5,047,055 A | 9/1991 | Bao et al. | |
| 5,192,326 A | 3/1993 | Bao et al. | |
| 5,242,444 A | 9/1993 | MacMillan | |
| 5,246,458 A | 9/1993 | Graham | |
| 5,338,297 A * | 8/1994 | Kocur et al. | 604/103.03 |
| 5,423,816 A | 6/1995 | Lin | |
| 5,458,642 A | 10/1995 | Beer et al. | |
| 5,534,028 A | 7/1996 | Bao et al. | |
| 5,549,679 A | 8/1996 | Kuslich | |
| 5,556,429 A | 9/1996 | Felt | |
| 5,645,597 A | 7/1997 | Krapiva | |
| 5,827,328 A | 10/1998 | Buttermann | |
| 5,928,284 A | 7/1999 | Mehdizadeh | |
| 5,954,671 A | 9/1999 | O'Neill | |
| 5,976,186 A | 11/1999 | Bao et al. | |
| 6,030,162 A | 2/2000 | Huebner | |
| 6,053,916 A | 4/2000 | Moore | |
| 6,086,589 A | 7/2000 | Kuslich et al. | |
| 6,140,452 A | 10/2000 | Felt et al. | |
| 6,175,758 B1 | 1/2001 | Kambin | |
| 6,187,048 B1 | 2/2001 | Milner et al. | |
| 6,235,043 B1 * | 5/2001 | Reiley et al. | 606/192 |
| 6,280,475 B1 | 8/2001 | Bao et al. | |
| 6,299,615 B1 | 10/2001 | Huebner | |
| 6,306,140 B1 | 10/2001 | Siddiqui | |
| 6,306,177 B1 | 10/2001 | Felt et al. | |
| 6,319,254 B1 | 11/2001 | Giet et al. | |
| 6,395,032 B1 | 5/2002 | Gauchet | |
| 6,402,784 B1 | 6/2002 | Wardlaw | |
| 6,419,704 B1 | 7/2002 | Ferree | |
| 6,440,138 B1 | 8/2002 | Reiley et al. | |
| 6,443,988 B2 | 9/2002 | Felt et al. | |
| 6,482,235 B1 | 11/2002 | Lambrecht et al. | |
| 6,500,173 B2 | 12/2002 | Underwood et al. | |
| 6,520,992 B1 | 2/2003 | Zollner et al. | |
| 6,558,386 B1 | 5/2003 | Cragg | |
| 6,558,390 B2 | 5/2003 | Cragg | |
| 6,562,046 B2 | 5/2003 | Sasso | |
| 6,582,466 B1 * | 6/2003 | Gauchet | 623/17.11 |
| 6,626,943 B2 * | 9/2003 | Eberlein et al. | 623/17.15 |
| 6,719,797 B1 | 4/2004 | Ferree | |
| 6,733,532 B1 * | 5/2004 | Gauchet et al. | 623/17.12 |
| 6,746,451 B2 | 6/2004 | Middleton et al. | |
| 6,793,656 B1 | 9/2004 | Mathews | |
| 6,805,697 B1 | 10/2004 | Helm et al. | |
| 7,048,717 B1 * | 5/2006 | Frassica | 604/165.04 |
| 7,291,150 B2 * | 11/2007 | Graf | 606/61 |
| 2001/0004710 A1 | 6/2001 | Felt et al. | |
| 2001/0049527 A1 | 12/2001 | Cragg | |
| 2002/0026244 A1 | 2/2002 | Trieu | |
| 2002/0032447 A1 | 3/2002 | Weikel et al. | |
| 2002/0035400 A1 * | 3/2002 | Bryan et al. | 623/17.15 |
| 2002/0068975 A1 | 6/2002 | Teitelbaum et al. | |
| 2002/0095154 A1 | 7/2002 | Atkinson et al. | |
| 2002/0147461 A1 | 10/2002 | Aldrich | |
| 2002/0147479 A1 | 10/2002 | Aldrich | |
| 2002/0151979 A1 | 10/2002 | Lambrecht et al. | |
| 2002/0156531 A1 | 10/2002 | Felt et al. | |
| 2002/0198527 A1 * | 12/2002 | Muckter | 606/73 |
| 2003/0083688 A1 | 5/2003 | Simonson | |
| 2003/0158556 A1 | 8/2003 | Taras et al. | |
| 2003/0195628 A1 | 10/2003 | Bao et al. | |
| 2003/0195630 A1 | 10/2003 | Ferree | |
| 2003/0220643 A1 | 11/2003 | Ferree | |
| 2003/0220649 A1 | 11/2003 | Bao et al. | |
| 2004/0002708 A1 | 1/2004 | Ritland | |
| 2004/0010317 A1 | 1/2004 | Lambrecht et al. | |
| 2004/0030392 A1 | 2/2004 | Lambrecht et al. | |
| 2004/0034429 A1 | 2/2004 | Lambrecht et al. | |
| 2004/0044412 A1 | 3/2004 | Lambrecht et al. | |
| 2004/0097924 A1 | 5/2004 | Lambrecht et al. | |
| 2004/0098756 A1 | 5/2004 | Singh | |
| 2004/0220296 A1 | 11/2004 | Lowman et al. | |
| 2004/0267269 A1 | 12/2004 | Middleton et al. | |
| 2005/0004593 A1 | 1/2005 | Simonson | |
| 2005/0010297 A1 | 1/2005 | Watson et al. | |
| 2005/0027358 A1 | 2/2005 | Suddaby | |

FOREIGN PATENT DOCUMENTS

| | | |
|---|---|---|
| FR | 2 814 936 | 4/2002 |
| WO | WO 92/10982 | 7/1992 |
| WO | WO 97/26847 | 7/1997 |
| WO | WO 02/17825 | 3/2002 |
| WO | WO 02/085262 | 11/2002 |
| WO | WO 03/047472 | 6/2003 |
| WO | WO 03/088878 | 10/2003 |
| WO | WO 2004/052248 | 6/2004 |

* cited by examiner

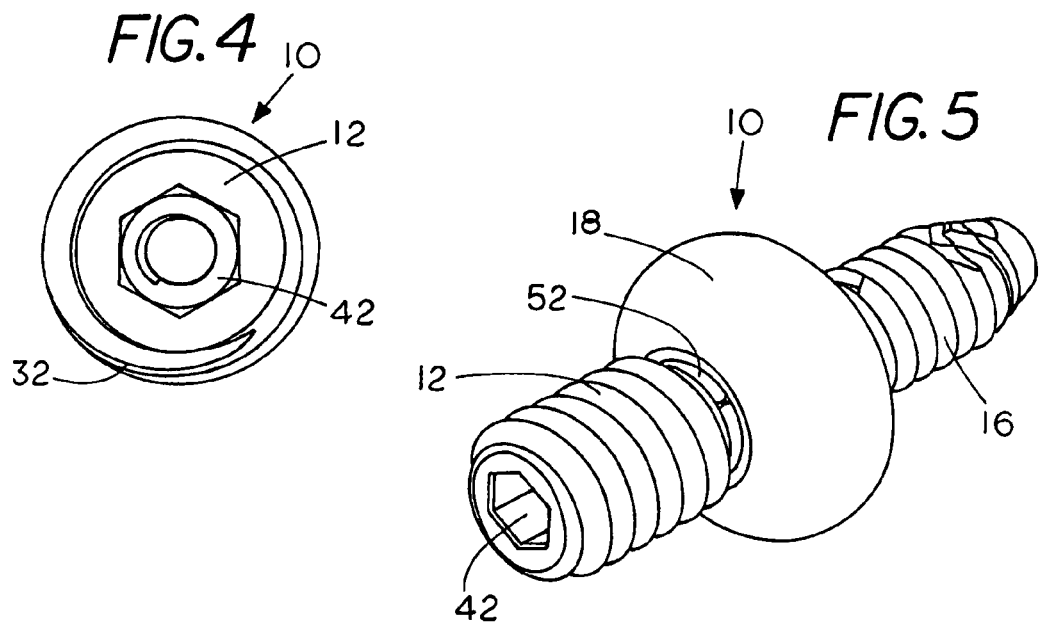
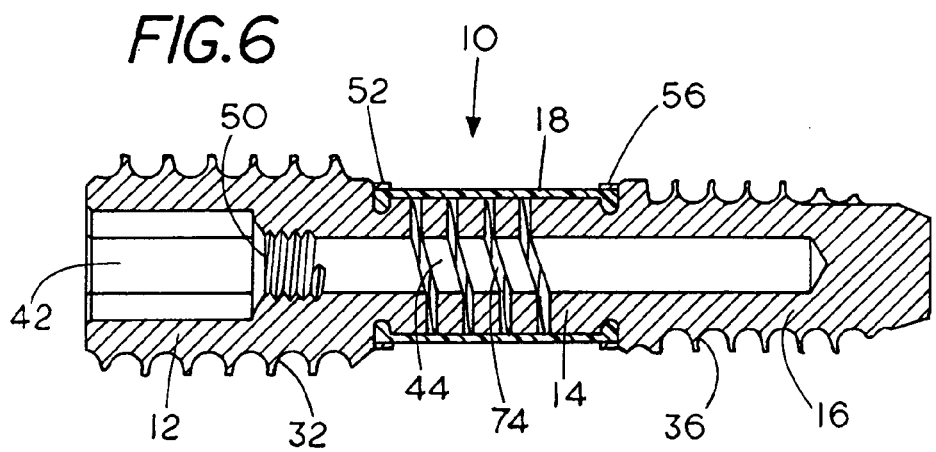
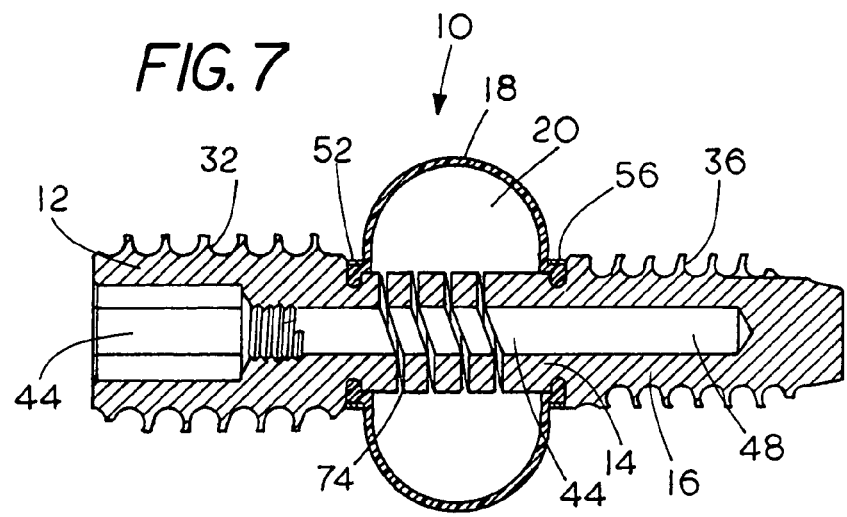

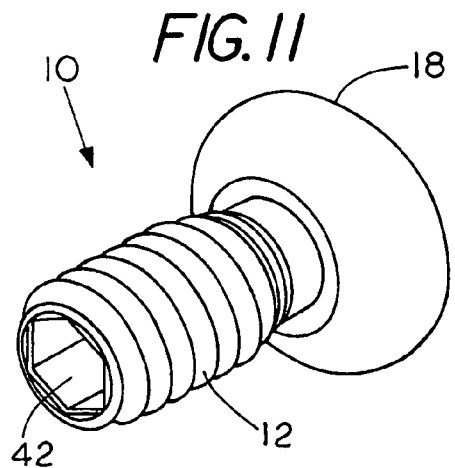
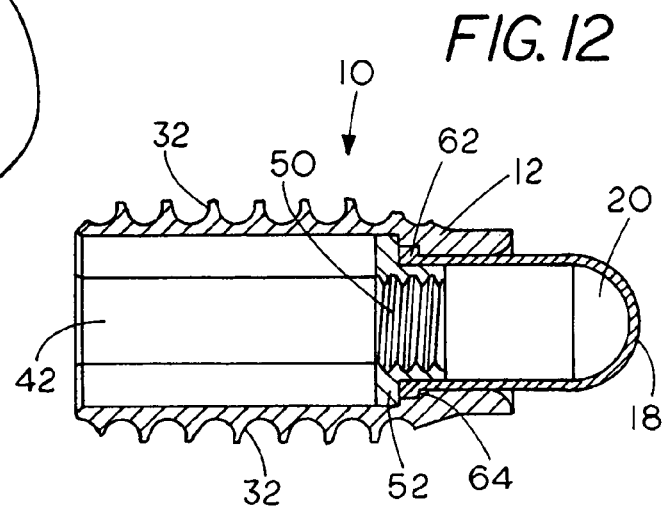
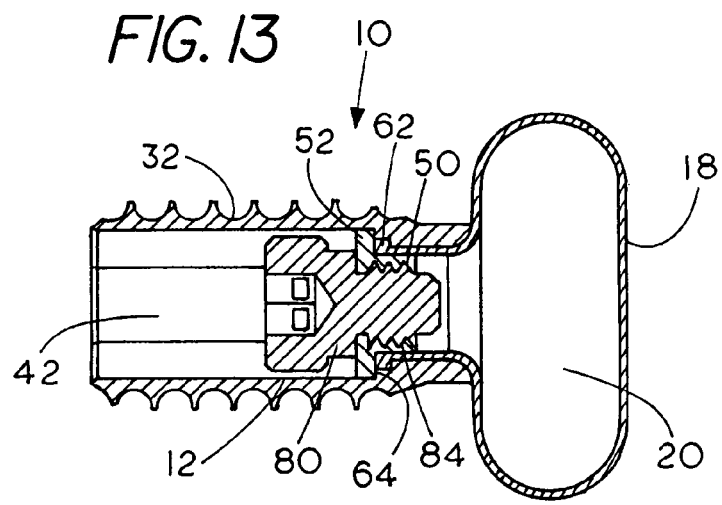
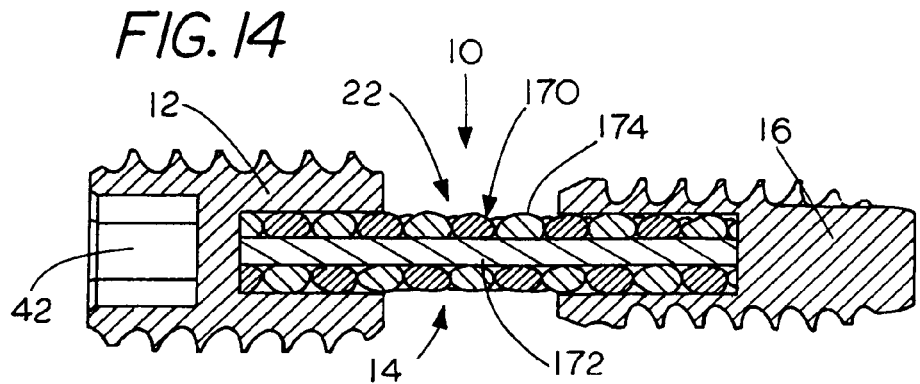

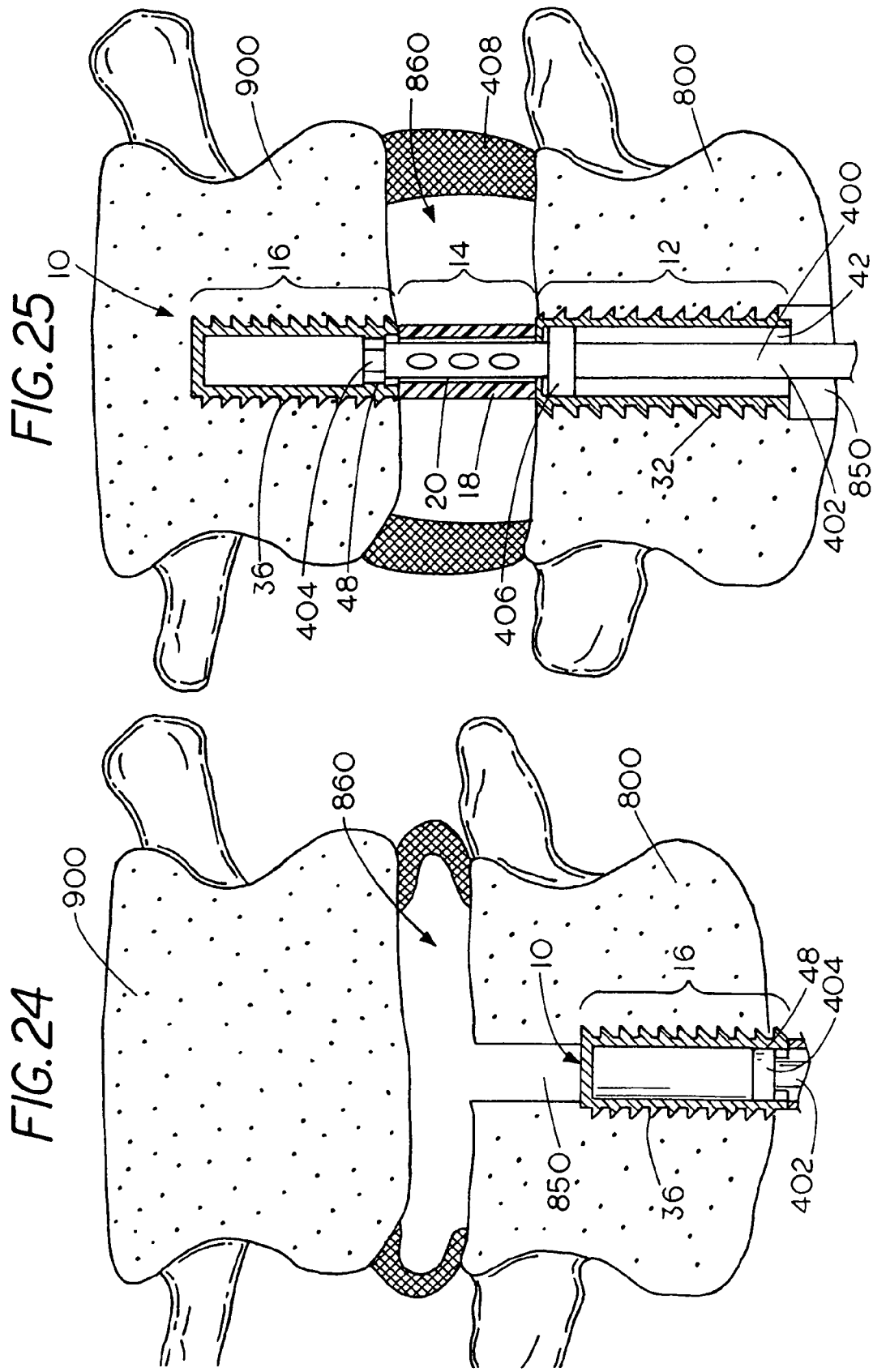

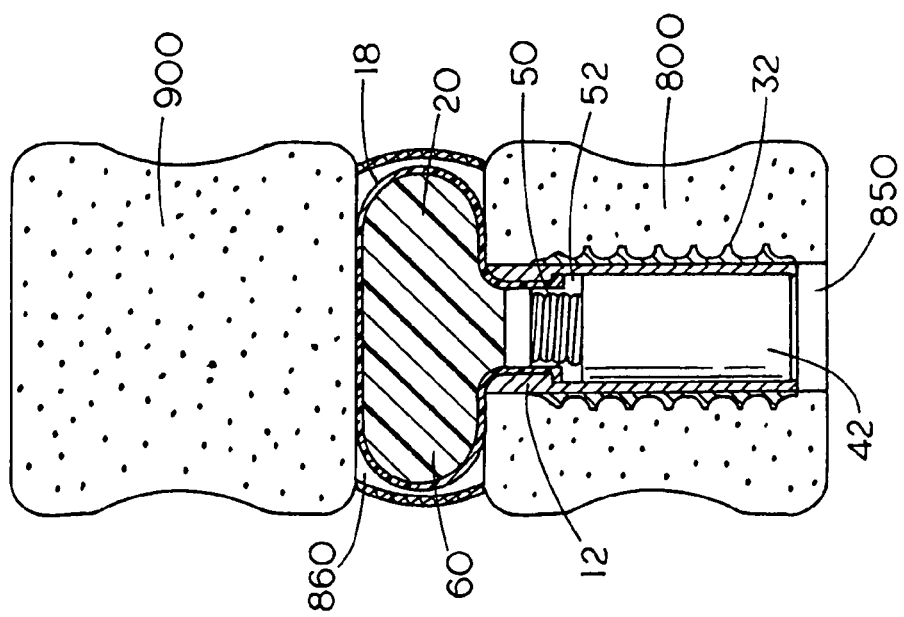
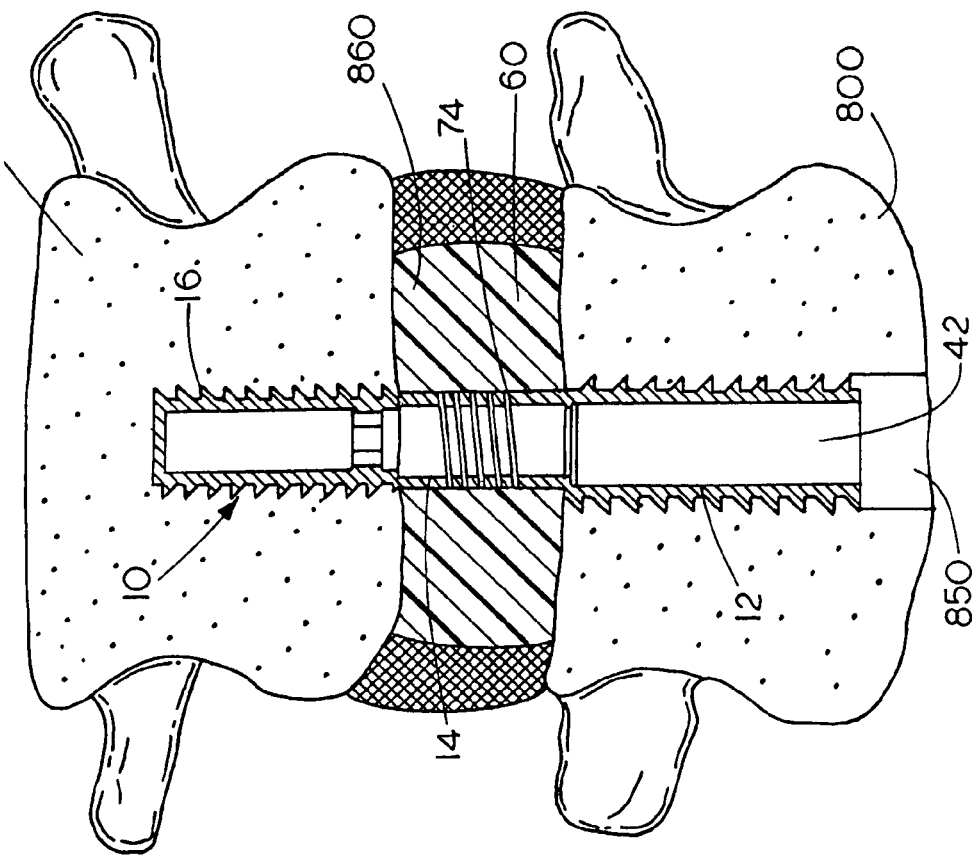

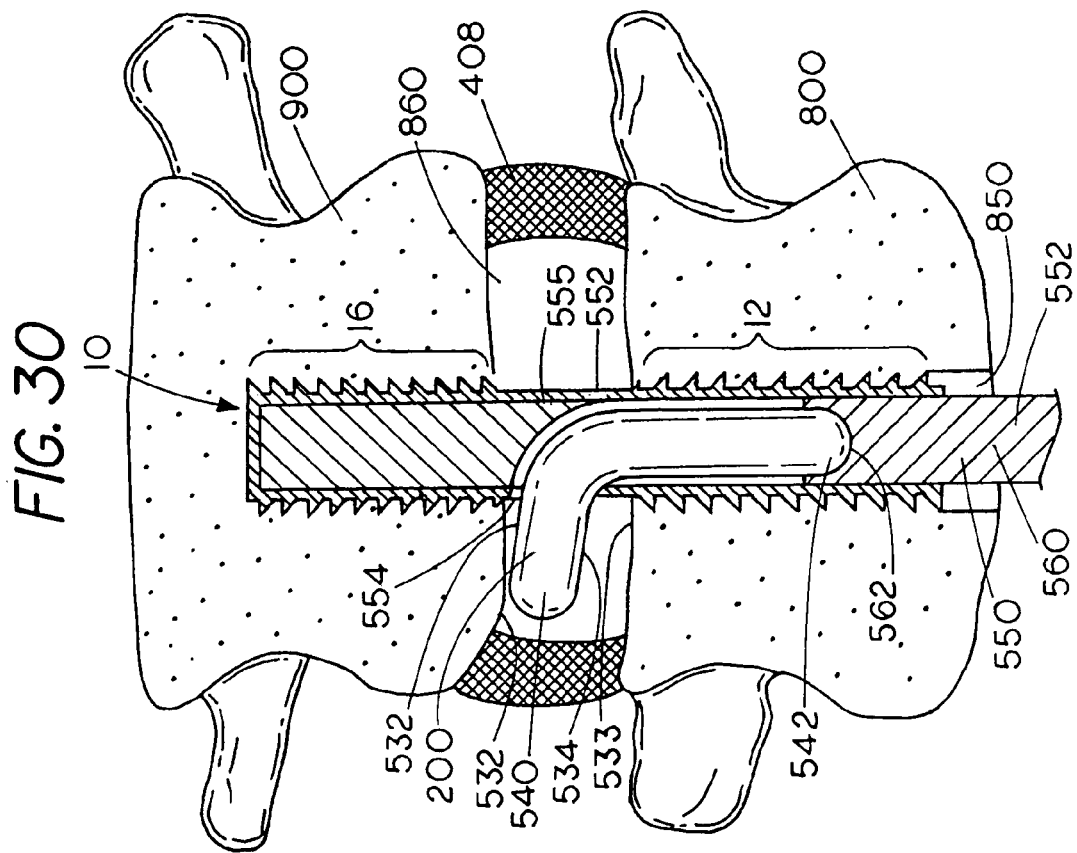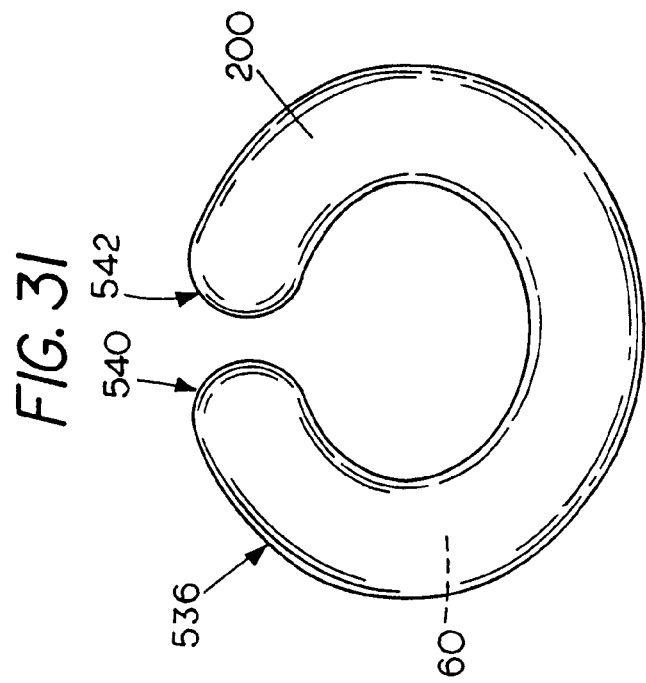

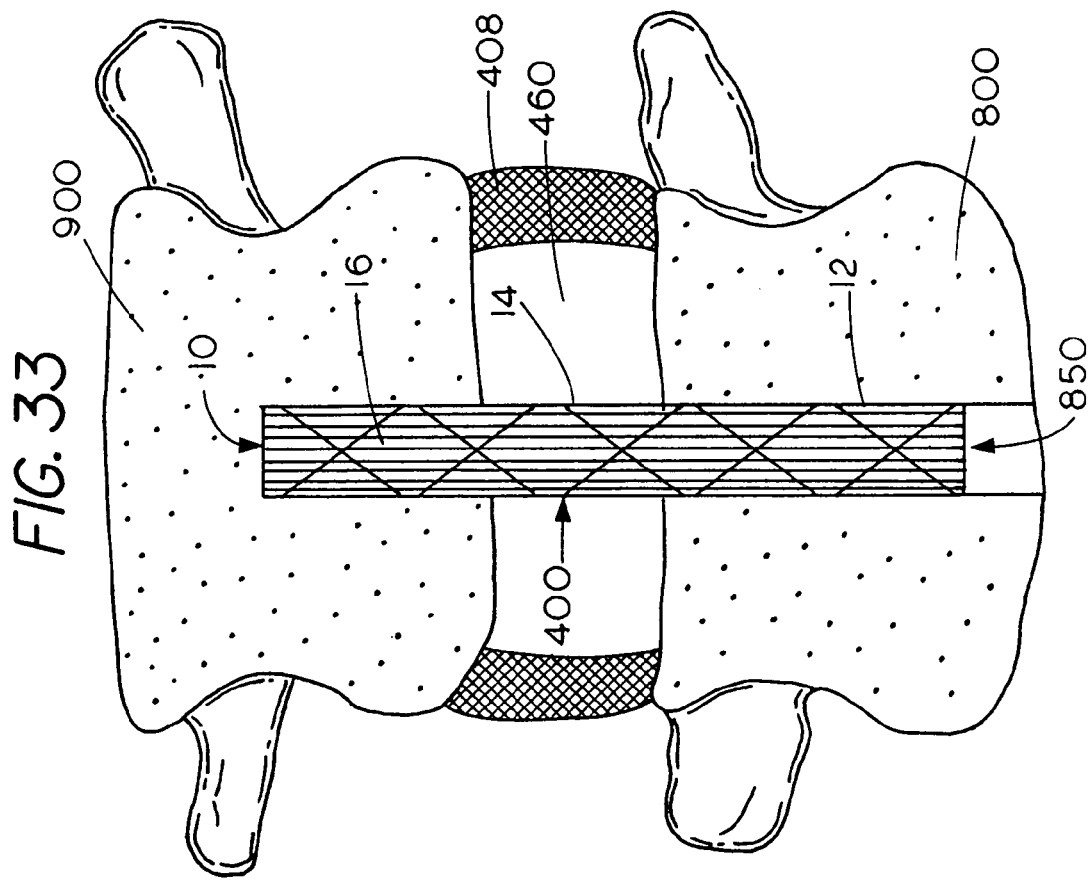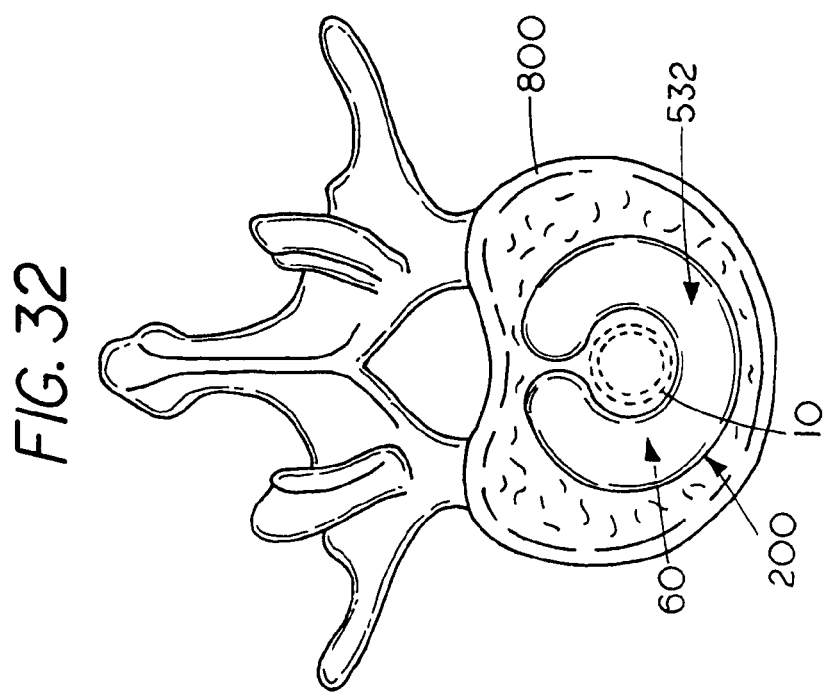

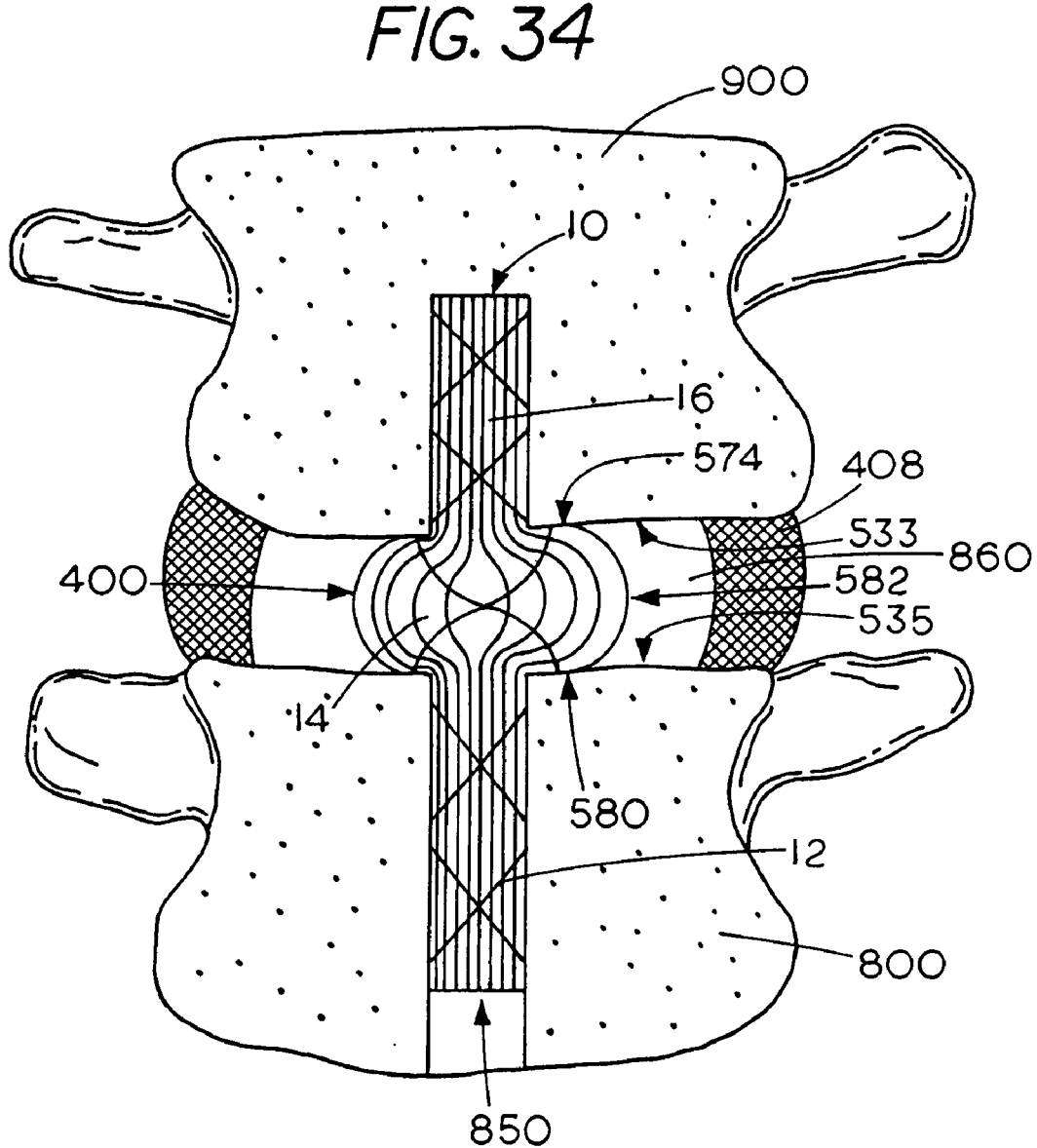

SPINAL MOBILITY PRESERVATION APPARATUS HAVING AN EXPANDABLE MEMBRANE

CROSS-REFERENCE TO RELATED APPLICATIONS

The present Utility Patent Application is a continuation of U.S. patent application Ser. No. 10/309,416 filed on Dec. 3, 2002, now U.S. Pat. No. 6,921,403, which is a continuation-in-part of U.S. patent application Ser. No. 10/125,771 filed on Apr. 18, 2002, now U.S. Pat. No. 6,899,716, which is a continuation-in-part of U.S. patent application Ser. No. 09/848,556 filed on May 3, 2001, now U.S. Pat. No. 7,014,633, which is a continuation-in-part of U.S. patent application Ser. No. 09/782,583 filed on Feb. 13, 2001, now U.S. Pat. No. 6,588,390, which, in turn, claims priority and benefits from U.S. Provisional Patent Application Ser. No. 60/182,748 filed on Feb. 16, 2000, each of which are incorporated in their entirety into this disclosure by reference. The present Utility Patent Application claims priority and benefits from and commonly assigned U.S. Provisional Patent Application Nos. 60/558,069, filed Mar. 31, 2004 and 60/513,899, filed Oct. 23, 2003, the disclosures of which are hereby incorporated by reference.

BACKGROUND OF THE INVENTION

1. Field of the Invention

The present invention relates to surgically implantable devices and, more particularly, to an apparatus and method for supporting the spine.

2. Description of the Related Art

Chronic lower back pain is a primary cause of lost work days in the United States. It is also a significant factor affecting both workforce productivity and health care expense. Therapeutic procedures for alleviating back pain range from conservative methods, e.g., with intermittent heat, rest, rehabilitative exercises, and medications to relieve pain, muscle spasm, and inflammation, to progressively more active and invasive surgical methods which may be indicated if these treatments are unsuccessful, including various spinal arthroplasties, and eventually even spinal arthrodesis, i.e., surgical fusion.

There are currently over 700,000 surgical procedures performed annually to treat lower back pain in the U.S. In 2004, it is conservatively estimated that there will be more than 200,000 lumbar fusions performed in the U.S., and more than 300,000 worldwide. These procedures represent approximately a $1 billion endeavor in an attempt to alleviate patients' pain. In addition, statistics show that only about 70% of these procedures performed will be successful in achieving this end.

Approximately 60% of spinal surgery takes place in the lumbar spine, and of that portion approximately 80% involves the lower lumbar vertebrae designated as the fourth lumbar vertebra ("L4"), the fifth lumbar vertebra ("L5"), and the first sacral vertebra ("S1"). Persistent low back pain is often attributable to degeneration of the disc between L5 and S1. Traditional, conservative methods of treatment include bed rest, pain and muscle relaxant medication, physical therapy or steroid injection. Upon failure of conservative therapy, spinal pain has traditionally been treated by surgical interventions. These surgeries have included spinal arthroplasty; arthrodesis, or fusion, which cause the vertebrae above and below the disc to grow solidly together and form a single, solid piece of bone. Yet, statistics show that only about 70% of these procedures performed will be successful in relieving pain.

There are multiple causes for a patient's lower back pain. The pain is frequently hypothesized to arise one or more of the following: bulging of the posterior annulus or PLL with subsequent nerve impingement; tears, fissures or cracks in the outer, innervated layers of the annulus; motion induced leakage of nuclear material through the annulus and subsequent irritation of surrounding tissue in response to the foreign body reaction, or facet pain. Generally, it is believed that 75% of cases are associated with degenerative disc disease. In cases of degenerative disc disease, the intervertebral disc of the spine suffers reduced mechanical functionality typically due to dehydration of the nucleus pulposus. Surgical procedures, such as spinal fusion and discectomy, may alleviate pain, but do not restore normal physiological disc function attributable to healthy anatomical form, i.e., intact disc structures such as the nucleus pulposus and annulus fibrosis, as described below.

The spinal column or backbone encloses the spinal cord and consists of 33 vertebrae superimposed upon one another in a series which provides a flexible supporting column for the trunk and head. The vertebrae cephalad (i.e., toward the head or superior) to the sacral vertebrae are separated by fibrocartilaginous intervertebral discs and are united by articular capsules and by ligaments. The uppermost seven vertebrae are referred to as the cervical vertebrae, and the next lower twelve vertebrae are referred to as the thoracic, or dorsal, vertebrae. The next lower succeeding five vertebrae below the thoracic vertebrae are referred to as the lumbar vertebrae and are designated L1-L5 in descending order. The next lower succeeding five vertebrae below the lumbar vertebrae are referred to as the sacral vertebrae and are numbered S1-S5 in descending order. The final four vertebrae below the sacral vertebrae are referred to as the coccygeal vertebrae. In adults, the five sacral vertebrae fuse to form a single bone referred to as the sacrum, and the four rudimentary coccyx vertebrae fuse to form another bone called the coccyx or commonly the "tail bone". The number of vertebrae is sometimes increased by an additional vertebra in one region, and sometimes one may be absent in another region.

Each vertebra has a spinous process, which is a bony prominence behind the spinal cord that shields the spinal cord's nerve tissue. The vertebrae also have a strong bony "vertebral body" in front of the spinal cord to provide a platform suitable for weight-bearing. Each vertebral body has relatively strong, cortical bone layer comprising the exposed outside surface of the body, including the endplates, and weaker, cancellous bone comprising the center of the vertebral body. The bodies of successive lumbar, thoracic and cervical vertebrae articulate with one another and are separated by the intervertebral discs. Each intervertebral disc comprises a fibrous cartilage shell enclosing a central mass, the "nucleus pulposus" (or "nucleus" herein) that provides for cushioning and dampening of compressive forces to the spinal column. The shell enclosing the nucleus comprises cartilaginous endplates adhered to the opposed cortical bone endplates of the cephalad and caudal vertebral bodies and the "annulus fibrosis" (or "annulus" herein) comprising multiple layers of opposing collagen fibers running circumferentially around the nucleus pulposus and connecting the cartilaginous endplates. The natural, physiological nucleus is comprised of hydrophilic (water attracting) mucopolysacharides and fibrous strands of protein polymers. In a healthy adult spine, the nucleus is about 80% water by mass. The disc is a hydrostatic system. The nucleus acts as a confined fluid within the annulus. It converts compressive on the vertebral end plates (axial loads) into tension on the annulus fibers. The nucleus is relatively inelastic, but the annulus can bulge outward slightly to accommodate loads axially applied to the spinal motion segment.

The intervertebral discs are anterior to the spinal canal and located between the opposed end faces or endplates of a cephalad and a caudal vertebral bodies. The inferior articular processes articulate with the superior articular processes of the next succeeding vertebra in the caudal (i.e., toward the feet or inferior) direction. Several ligaments hold the vertebrae in position yet permit a limited degree of movement. The ligaments include the supraspinous, the interspinous, the anterior and the posterior longitudinal, and the ligamenta flava. The assembly of two vertebral bodies, the interposed, intervertebral, spinal disc and the attached ligaments, muscles and facet joints is referred to as a "spinal motion segment". In essence, the spine is designed so that vertebrae "stacked" together can provide a movable support structure while also protecting the spinal cord's nervous tissue that extends down the spinal column from the brain.

The spine has defined range of motion. Its range of motion can be described in terms of degrees of motion. More particularly, the spines range of motion is typically described relative to translation and rotation about three orthogonal planes relative to an instantaneous center of rotation around the vertical axis of the spine. This can generally be broken down into six degrees of motion. These include flexion, extension, compression, rotation, lateral bending, and distraction.

Flexion and extension of the spine combine forward sliding and rotation of the vertebrae. The facet joints and the annulus resist the forward sliding. Rotation is resisted by the annulus; capsules of the facet joints; action of the back muscles, and passive tension generated by the thoracolumbar fascia. Extension is resisted by the facet joints, and secondarily by the annulus. The spine is typically resistant to injury if the force is only in pure flexion, as the combination of the facet joints and disc are intrinsically stable in this plane. While the spinal muscles can be injured during forceful flexion since they are important in controlling this motion, ensuing pain is not typically chronic. Extension is impaired by impaction of the facet joints and eventually the inferior articular process against the lamina. This can result in a cartilage injury of the facet joint; disruption of the facet capsule, and facet joint or pars interarticularis fracture.

Compression of the spine is due to body weight and loads applied to the spine. Body weight is a minor compressive load. The major compressive load on the spine is produced by the back muscles. As a person bends forward, the body weight plus an external load must be balanced by the force generated by the back muscles. That is, muscle loads balance gravitational loads so that the spine is in equilibrium, to preclude us from falling over. The external force is calculated by multiplying the load times the perpendicular distance of the load from the spine. In essence, the further the load is from the spine, the larger the compressive load is on the spine. Since the back muscles act close to the spine, they must exert large forces to balance the load. The force generated by the back muscles results in compression of spinal structures. Most of the compressive loads (~80%) are sustained by the anterior column which includes the intervertebral discs and the vertebral bodies.

Compression injuries occur by two main mechanisms. It generally occurs by either axial loading by gravity or by muscle action. Gravitational injuries result from a fall onto the buttocks while muscular injuries result from severe exertion during pulling or lifting. A serious consequence of the injury is a fracture of the vertebral end plate. Since the end plate is critical to disc nutrition, an injury can change the biochemical and metabolic state of the disc. If the end plate heals, the disc may suffer no malice. However, if the end plate does not heal, the nucleus can undergo harmful changes. The nucleus loses its proteoglycans and thus, its water-binding capacity. The hydrostatic properties of the nucleus are compromised. Instead of sharing the load between the nucleus and the annulus, more load is transferred to the annulus. The annulus fibers then fail. In addition to annular tears, the layers of the annular separate (delaminate). The disc may collapse or it may maintain its height with progressive annular tearing. If the annulus is significantly weakened, there may be a rupture of the disc whereby the nuclear material migrates into the annulus or into the spinal canal causing nerve root compression.

Rotation of the spine is accomplished by the contraction of the abdominal muscles acting through the thorax and the thoracolumbar fascia. There are no primary muscles responsible for lumbar rotation. The facet joints and the collagen fibers of the annulus resist this rotation. In rotation, only 50% of the collagen fibers are in tension at any time, which renders the annulus susceptible to injury.

The spine is particularly susceptible to injury in a loading combination of rotation and flexion. Flexion pre-stresses the annular fibers. As the spine rotates, compression occurs on the facet joint surfaces of the joint opposite the rotation. Distraction occurs on the facet joint on the same side of the rotation. The center of rotation of the motion segment shifts from the back of the disc to the facet joint in compression. The disc shifts sideways and shear forces on the annular fibers are significant. Since the annular fibers are weak in this direction, they can tear. If the rotation continues, the facet joints can sustain cartilage injury, fracture, and capsular tears while the annulus can tear in several different ways. Any of these injuries can be a source of pain.

Lateral bending is a combination of lateral flexion and rotation through the annulus and facet joints.

Pure distraction rarely occurs and is usually a combination of tension and compression on the spinal joints depending on the direction of applied force. An example of a distraction force is therapeutic spinal traction to "unload" the spine. In the context of the present invention, the term distraction may refer procedurally to an elevation in height that increases the intervertebral disc space 860 resulting during or from introduction of a spinal implant. Temporary distraction will generally refer to elevation of disc height by an apparaus which is subsequently removed but wherein the elevation is retained intra-operatively, while the patient remains prone. Thus, an implant may be inserted into an elevated disc space 860 first created by another apparatus, and thereafter physical presence and dimensionality of the implanted apparatus would preserve the level of distraction.

Prior devices have typically not preserved, restored or otherwise managed these six ranges of motion. Accordingly, a need exists for apparatus and methods for preserving, restoring, and/or managing mobility of the spine.

As noted above, the nucleus pulposus that forms the center portion of the intervertebral disc consists of 80% water that is absorbed by the proteoglycans in a healthy adult spine. With aging, the nucleus becomes less fluid and more viscous and sometimes even dehydrates and contracts causing severe pain in many instances. This is sometimes referred to as "isolated disc resorption". The intervertebral discs serve as "dampeners" between each vertebral body. They generally function to minimize the impact of movement on the spinal column. Intervertebral disc degeneration, which may be marked by a decrease in water content within the nucleus, can render the intervertebral discs ineffective in transferring loads to the annulus layers. In addition, the annulus tends to thicken, desiccate, and become more rigid with age. This decreases the ability of the annulus to elastically deform under load which can make it susceptible to fracturing or fissuring. One form of disc degeneration occurs when the annulus fissures or is torn. The fissure may or may not be accompanied by extrusion of nucleus material into and beyond the annulus. The fissure itself may be the sole morphological change, above and beyond generalized degenerative changes in the connective tissue of the disc, and disc fissures can nevertheless be painful and debilitating. Biochemicals contained within the nucleus are enabled to escape through the fissure and irritate nearby structures.

A fissure also may be associated with a herniation or rupture of the annulus causing the nucleus to bulge outward or extrude out through the fissure and impinge upon the spinal column or nerves. This is commonly termed a "ruptured" or "slipped" disc. Herniations may take a number of forms. With a contained disc herniation, the nucleus may work its way partly through the annulus but is still contained within the annulus or beneath the posterior longitudinal ligament, and there are no free nucleus fragments in the spinal canal. Nevertheless, even a contained disc herniation is problematic because the outward protrusion can press on the spinal cord or on spinal nerves causing sciatica.

Another disc problem occurs when the disc bulges outward circumferentially in all directions and not just in one location. This occurs when, over time, the disc weakens bulges outward and takes on a "roll" shape. Mechanical stiffness of the joint is reduced and the spinal motion segment may become unstable, shortening the spinal cord segment. As the disc "roll" extends beyond the normal circumference, the disc height may be compromised, and foramina with nerve roots are compressed causing pain. Current treatment methods other than spinal fusion for symptomatic disc rolls and herniated discs include "laminectomy" which involves the surgical exposure of the annulus and surgical excision of the symptomatic portion of the herniated disc followed by a relatively lengthy recuperation period. In addition, osteophytes may form on the outer surface of the disc roll and further encroach on the spinal canal and foramina through which nerves pass. The cephalad vertebra may eventually settle on top of the caudal vertebra. This condition is called "lumbar spondylosis".

Various other surgical treatments that attempt to preserve the intervertebral spinal disc and to simply relieve pain include a "discectomy" or "disc decompression" to remove some or most of the interior nucleus thereby decompressing and decreasing outward pressure on the annulus. In less invasive microsurgical procedures known as "microlumbar discectomy" and "automated percutaneous lumbar discectomy", the nucleus is removed by suction through a needle laterally extended through the annulus. Although these procedures are less invasive than open surgery, they nevertheless suffer the possibility of injury to the nerve root and dural sac, perineural scar formation, re-herniation of the site of the surgery, and instability due to excess bone removal. In addition, they generally involve the perforation of the annulus.

Although damaged discs and vertebral bodies can be identified with sophisticated diagnostic imaging, existing surgical interventions so extensive and clinical outcomes are not consistently satisfactory. Furthermore, patients undergoing such fusion surgery experience typically have significant complications and uncomfortable, prolonged convalescence. Surgical complications may include disc space 860 infection, nerve root injury, hematoma formation, instability of adjacent vertebrae, and disruption of muscles, tendons, and ligaments.

Any level of the spine can be affected by disc degeneration. When disc degeneration affects the spine of the neck, it is referred to as cervical disc disease, while when the mid-back is affected, the condition is referred to as thoracic disc disease. Disc degeneration that affects the lumbar spine causes pain localized to the low back and is sometimes common in older persons and known as lumbago Degenerative arthritis (osteoarthritis) of the facet joints is also a cause of localized lumbar pain that can be diagnosed via x-ray analysis.

Radiculopathy refers to nerve irritation caused by damage to the disc between the vertebrae. This occurs because of degeneration of the annulus fibrosis of the disc, or due to traumatic injury, or both. Weakening of the annulus may lead to disc bulging and herniation. With bulging and herniation, the nucleus pulposus can rupture through the annulus and abut the spinal cord or its nerves as they exit the bony spinal column. When disc herniation occurs, the rupture of the nucleus pulposus into or through the annulus may irritate adjacent nervous tissue, causing local pain, or discogenic pain, in the affected area.

The pain from degenerative disc or joint disease of the spine may be treated conservatively with intermittent heat, rest, rehabilitative exercises, and medications to relieve pain, muscle spasm, and inflammation. However, if these treatments are unsuccessful, progressively more active interventions may be necessary. These more active interventions may include spinal arthroplasty including prosthetic nucleus device implantation; annulus repair, and total disc replacement, and eventually, even spinal arthrodesis. The nature of the intervention performed depends on the overall status of the spine, and the age and health of the patient. In some cases, the intervention may include the removal of the herniated disc with laminotomy (a small hole in the bone of the spine surrounding the spinal cord), a laminectomy (removal of the bony wall), percutaneous discectomy (removal by needle technique through the skin), chemonucleolysis (various chemical disc-dissolving procedures), among other procedures.

When narrowing of the spaces in the spine results in compression of the nerve roots or spinal cord a condition known as spinal stenosis may occur. Spinal stenosis occurs when bony spurs or soft tissues, such as discs, impinge upon the spinal canal to compress the nerve roots or spinal cord. Spinal stenosis occurs most often in the lumbar spine, but also occurs in the cervical spine and less often in the thoracic spine. It is frequently caused by degeneration of the discs between the vertebrae due to osteoarthritis. Rheumatoid arthritis usually affects people at an earlier age than osteoarthritis does and is associated with inflammation and enlargement of the soft tissues of the joints. The portions of the vertebral column with the greatest mobility, i.e., the cervical spine, are often the portions most affected in people with rheumatoid arthritis. However, there are known non-arthritic causes of spinal stenosis. Some non-arthritic causes of spinal stenosis include tumors of the spine, trauma, Paget's disease of bone, and fluorosis.

Therapeutic procedures to alleviate pain are restore function are described in a progression of treatment from spinal arthroplasty to spinal arthrodesis. As used herein, spinal arthroplasty encompasses options for treating disc degeneration when arthrodesis is deemed too radical an intervention based on an assessment of the patient's age, degree of disc degeneration, and prognosis. Spinal arthrodesis, or fusion, involves a discectomy, i.e., surgical removal of the disc, followed by the subsequent immobilization of a spinal motion segment. A spinal motion segment is generally comprised of two adjacent vertebral bodies separated axially by a spinal disc. The procedure of discectomy and "fusion" of the vertebral bodies results in the two vertebrae effectively becoming one solid bone. Accordingly, the procedure terminates all motion at that joint in an attempt to eliminate or at least ameliorate discogenic pain. The benefit of fusion is pain relief and the down side is elimination of motion at the fused joint, which can hinder function. This surgical option is reserved for patients with advanced disc degeneration.

Several companies are pursuing the development of prosthesis for the human spine, intended to partly or completely replace a physiological disc. In individuals where the degree of degeneration has not progressed to destruction of the annulus, rather than a total artificial disc replacement, a preferred treatment option may be to replace or augment the nucleus pulposus. This augmentation may involve the deployment of a prosthetic disc nucleus. As noted previously, the normal nucleus is contained within the space bounded by the bony vertebrae above and below it and the annulus fibrosus, which circumferentially surrounds it. In this way the nucleus is completely encapsulated and sealed with the only communication to the body being a fluid exchange that takes place through the bone interface with the vertebrae, known as the endplates. The hydroscopic material comprising the physiological nucleus has an affinity for water which is sufficiently powerful to distract (i.e., elevate or "inflate") the intervertebral disc space, despite the significant physiological loads that are carried across the disc in normal activities. These forces, which range from about 0.4× to about 1.8× body weight, generate local pressure well above normal blood pressure, and the nucleus and inner annulus tissue are, in fact, effectively avascular. In essence, the existence of the nucleus, as a cushion, and the annulus, as a flexible member, contributes to the range of motion in the normal disc.

As noted previously, some current devices are configured to form an artificial disc or an artificial nucleus. However, many of these devices are susceptible to movement between the vertebral bodies. Further, they may erode or degrade. In addition, they may extrude through the site of implantation in the annulus or otherwise migrate out of place. Some of these drawbacks relate to the fact that their deployment typically involves a virtually complete discectomy achieved by instruments introduced laterally through the patient's body to the disc site and manipulated to cut away or drill lateral holes through the disc and adjoining cortical bone. The endplates of the vertebral bodies, which comprise very hard cortical bone and help to give the vertebral bodies needed strength, are usually weakened or destroyed during the drilling. The vertebral endplates are special cartilage structures that surround the top and bottom of each vertebra and are in direct contact with the disc. They are important to the nutrition of the disc because they allow the passage of nutrients and water into the disc. If these structures are injured, it can lead to deterioration of the disc and altered disc function. Not only do the large laterally drilled hole or holes compromise the integrity of the vertebral bodies, but the spinal cord can be injured if they are drilled too posteriorly.

Alternatively, current devices are sometimes deployed through a surgically created or enlarged hole in the annulus. The annulus fibrosis consists of tough, thick collagen fibers. The collagen fibers which comprise the annulus fibrosis are arranged in concentric, alternating layers. Intra-layer orientation of these fibers is parallel, however, each alternating (i.e., interlayer) layers' collagen fibers are oriented obliquely (~120'). This oblique orientation allows the annulus to resist forces in both vertical and horizontal directions. Axial compression of a disc results in increased pressure in the disc space. This pressure is transferred to the annulus in the form of loads (stresses) perpendicular to the wall of the annulus. With applied stress, these fibrous layers are put in tension and the angle from horizontal decreases to better resist the load, i.e., the annulus works to resist these perpendicular stresses by transferring the loads around the circumference of the annulus (Hoop Stress). Vertical tension resists bending and distraction (flexion and extension). Horizontal tension resists rotation and sliding (i.e., twisting). While the vertical components of the annulus' layers enable the disc to withstand forward and backward bending well, only half of the horizontal fibers of the annulus are engaged during a rotational movement. In general, the disc is more susceptible to injury during a twisting motion, deriving its primary protection during rotation from the posterior facet joints; however, this risk is even greater if and when the annulus is compromised.

Moreover, annulus disruption will remain post-operatively, and present a pathway for device extrusion and migration in addition to compromising the physiological biomechanics of the disc structure. Other devices, in an attempt to provide sufficient mechanical integrity to withstand the stresses to which they will be subjected, are configured to be so firm, stiff, and inflexible that they tend to erode the bone or become imbedded, over time, in the vertebral bodies, a phenomenon known as "subsidence", sometimes also termed "telescoping". The result of subsidence is that the effective length of the vertebral column is shortened, which can subsequently cause damage to the nerve root and nerves that pass between the two adjacent vertebrae.

SUMMARY OF THE INVENTION

In one aspect, the present invention may provide alternative options for treating disc degeneration when arthrodesis or fusion is deemed too radical an intervention based on an assessment of the patient's age, degree of disc degeneration, and prognosis. Specifically, the present invention includes an axially deployed mobility preservation apparatus which may provide discogenic pain relief and dynamic stabilization, by elevating and maintaining distraction while preserving mobility. The mobility preservation apparatus may also restore or manage range of motion and, thereby substantially improve biomechanical function as compared to current methods and devices.

In the context of the present invention, "biomechanics" will refer to physiological forces on intervertebral disc components (individually and collectively) attributable to movement of the lumbar spine, described in the previous explanation of the six degrees of freedom which comprise spinal range of motion.

In one aspect of the present invention, spinal axially deployed mobility preservation apparatus are deployed into the disc space 860 in a minimally traumatic fashion via a trans-sacral, axial approach rather than laterally through the annulus. The trans-sacral, axial approach permits axial implantation without compromising it anatomically or functionally impairing its physiological load sharing by accessing the nucleus laterally through a hole or fissure in the annulus. Risks of expulsion or migration through an uncompromised annulus are inherently less, and are reduced even further by a mobility preservation apparatus having at least one bone anchor in accordance with the present invention. A mobility preservation apparatus in accordance with the present invention typically includes one or more bone anchor to engage at least one vertebral body. The mobility preservation apparatus may also include an access tract plug to seal at least one axial access tract into at least one vertebral body through which the mobility preservation apparatus may be deployed. Yet another advantage of the mobility preservation apparatus in accordance with the present invention is that their axial deployment in the spine may enable anchoring in the vertebral body which is readily accessible through axial access methods and provides a relatively large bone for anchoring.

In the context of the present invention, "dynamic" refers to non-static devices with an inherent ability to allow mobility by enabling or facilitating forces or load bearing that assist or substitute for physiological structures that are otherwise compromised, weakened or absent. The mobility preservation apparatus of the present invention may provide dynamic stabilization across a progression-of-treatment interventions for treating symptomatic discogenic pain, ranging from treatment in patients where little degeneration or collapse is evident radio-graphically, to those for whom prosthetic nucleus devices or total disc replacements are indicated. For example, a mobility preservation apparatus having a prosthetic nucleus would be indicated in patients with a greater degree of degeneration and loss of disc height but not to the stage where advanced annular break-down is present. A mobility preservation apparatus having a prosthetic nucleus may go beyond dynamic stabilization by filling the de-nucleated space left by an aggressive nucleectomy with an appropriate material. Here, the goal may be to restore, as opposed to preserve, disc height and motion. A mobility preservation apparatus having a larger prosthetic nucleus may provide a total disc replacement which would be indicated with more advanced disease than with a standard prosthetic nucleus but where some annular function remains. The mobility preservation apparatus in accordance with the present invention may be configured to augment, preserve, restore, and/or manage the physiological function according to the intervention indicated. In general, the axial mobility preservation apparatus of the present invention disclosed herein may be configured as devices with an aspect ratio of greater than 1. That is, the dimension in the axial vertebral plane of the mobility preservation apparatus is greater than its dimension in any orthogonal direction to that axial vertebral plane in close proximity to the physiological instantaneous center of axial rotation. The mobility preservation apparatus can be deployed in an orientation in approximately the line of principal compressive stress. Further, the mobility preservation apparatus can be placed at approximately the center of rotation vis à human disc motion segment.

In one aspect of the present invention, certain embodiments of the mobility preservation apparatus include an elongated body having an intermediate section in between distal and proximal threaded bone anchor portions. The intermediate section may include at least a portion which is flexible. The flexible portion may be a cable, a spring, a spiral flexure, a notched flexure, a flexible coupler, a set of stacked-washers over a cable or wire, inflatable bladder (e.g., expandable membrane), or another element or combination of elements as will be recognized by those skilled in the art upon review of the present disclosure. The flexible portion may serve as the dampener previously described and is able to assimilate forces or redistribute loads. Hence, in accordance with this aspect of the present invention, the mobility preservation apparatus may include a proximal and a distal body connected by an intermediate section with one or more flexible portions. The elongated body may be configured from a one-piece, two-piece, or three-piece design. The mobility preservation apparatus may be configured with or without an expandable membrane that may maximize surface area over which loads are distributed, and that may or may not assist in distraction. The expandable membrane may be integral, it may be elastomeric or elastic, and it may be foldable to expand into an unfolded position to be expandable. The mobility preservation apparatus may include cable designs for its intermediate section. The cable may be one piece of fixed length with or without an inflatable membrane, or two or more parts of variable length. The mobility preservation apparatus may include ball and track multi-component designs as the flexible portion of the intermediate section. In another embodiment, an expandable membrane component may be folded within a cannulated section of the mobility device during device delivery to the target site, and then deployed, e.g., unfolded, in situ via expansion by infusion or inflation. A non-inflatable collar may also be provided and used in conjunction with the expanding membrane. The collar is first deployed by folding or may be secured to the expanding membrane, and is configured to conform with (i.e., buttress) the annulus to prevent migration or leakage of the membrane through herniations. The cross sectional area of the collar is stiffer, relative to the expandable membrane. In a preferred embodiment the collar is from between about 8 mm-12 mm high and about 0.5 to 1.0 mm thick (see FIGS. 13 & 14). In another embodiment, the mobility preservation apparatus may include a single bone anchor secured to a prosthetic nucleus.

In another embodiment of the present invention, the axially deployed, spinal mobility preservation apparatus is configured to further include a prosthetic nucleus including a semi-compliant expandable membrane to contain at least one prosthetic nucleus material. The prosthetic nucleus material is typically biocompatible and may be physiologic saline, an elastomer, a hydrogel, or combinations or blends thereof. In one aspect, the prosthetic nucleus is configured to functionally reproduce the same load-bearing characteristics as the natural disc's nucleus pulposus, to preserve and restore mobility. The expandable membrane may be configured to contain prosthetic nucleus material delivered through an elongated delivery tube or catheter, wherein the distal end of the tube is inserted through a cannula into the proximal end of the mobility preservation apparatus which end engages an expandable membrane which is attached in or on the elongated body. The expandable membrane is typically attached or secured to the elongated body by an adhesive or by laser-welding of a retainer ring either to the interior walls of a lumen at the proximal end of the elongated body, or directly to its distal end. The expandable membrane is enlarged or filled through a lumen, apertures or fenestrations which enable fluid communication between the exterior and interior of the intermediate segment of the mobility preservation apparatus and through which prosthetic nucleus material is infused into the expandable membrane which is deployed over and surrounding the intermediate segment. In this manner, the expandable membrane may inflate and extend into the intervertebral disc space. In one aspect, when filled, the expandable membrane conformably contacts the surfaces within the intervertebral disc space. The expandable membrane may be configured from an elastomeric material, with a Durometer Shore A hardness in the range of substantially about 20-90, that is deployable, stable and biocompatible in situ, e.g., such as silicone rubber. The ultimate expansion of the membrane is typically limited by contact with the end plates and the annulus, preventing rupture of the membrane due to over inflation.

The expandable membrane is typically expanded with a prosthetic nucleus material that may include elastomeric solids and/or viscoelastic gels, i.e., materials whose viscoelastic properties (e.g., rheology and compressibility) in conjunction with the biomechanical properties of outer expandable membrane, enable them to perform in an functional manner which is substantially equivalent to the physiologic disc nucleus. In one embodiment, the prosthetic nucleus material is a hydrogel. The hydrogel can be introduced into the membrane in a liquid or dry particulate form or in microspheres or beads. For example, one hydrogel is formulated as a mixture of hydrogel polyacrylonitrile or any hydrophilic acrylate derivative with a unique multiblock copolymer structure or any other hydrogel material having the ability to imbibe and expel fluids while maintaining its structure under various stresses.

As an example, the hydrogel can be formulated as a mixture of polyvinyl alcohol and water. The hydrogel core formed within the envelope will swell as it absorbs fluids through the porous fabric wall of the envelope, preferably in the manner of a native nucleus. When fully hydrated, the hydrogel core may have a water content of between 25-95%. The hydrogel material of one suitable embodiment is manufactured under the trade name Hypan® by Hymedix International, Inc., and has a water content of about 80-95%. Another hydrogel system comprises natural hyaluronan gels or blends that may be chemically altered to enhance structure, e.g., scaffolding ability or physical state, and optimize biomechanical properties in situ via laser exposure, e.g., to convert liquid into a solid. Yet other hydrogels (Poly(ethylene glycol) (PEG); Poly(ethylene Oxide) (PEO); Poly(vinyl pyrollidine) (PVP)) or blends of hydrogels (e.g., Poly(vinyl acetate) (PVA)/PVP; PEG-based/Polyethylene (PE) glycated hydrogels; crosslinked aliphatic polyoxaamide polymers; or combinations of synthetic and native polypeptides or glycosaminoglycans (GAGs) such as such as actin, fibrinogen, collagen and elastin; chondroitin, keratin and dermatan sulfate; chitosan) and/or elastomers or other combinations (e.g., incorporation of an ionic or hydrophobic monomer into the hydrogel network, to engineer a reversibly responsive polymer) that optimize desired intramolecular and intermolecular bonding arrangements and reproduce the viscoelastic properties of the native nucleus, may also be used. Conceptually, this is enabled from understanding fundamental relationships between the structure of the polymer (e.g., molecular weight; cross-linking density, etc.) under physiological conditions and the physical properties of the resulting hydrogels. As noted previously, the native nucleus consists of mostly type II collagen (cartilage like) and large protein macromolecules called proteoglycans that absorb water into the disc and are extremely important to the biomechanical properties of the disc. Hydrogels modify their molecular arrangement, volume and/or phase when acted upon by a specific stimulus such as temperature, light, a pH change or other chemical inducement, osmotic pressure or mechanical stress, or electric field, and selection of the prosthetic nucleus material of the present invention is not limited in scope with respect to materials' trigger stimuli, and may include those that are either chemically and/or physically cross-linked gels (e.g., via ion-complexation or those that are thermoreversibly cross-linked) as suitable. Hence in a preferred embodiment, the prosthetic nucleus material is selected based on its stability under physiological conditions and/or in physiological fluids, including the ability withstand load, resist shear stresses and fatigue forces, or other factors that might otherwise induce fragmentation or otherwise promote extrusion or migration, or fractional mass loss over time.

As noted earlier, the mobility preservation apparatus of the present invention may be deployed following complete or partial nucleectomy to remove all or most of the nucleus, respectively, to create a space within the intervertebral disc. However, generally the access tract through which a prosthetic nucleus device containing the prosthetic nucleus material is axially deployed will be smaller spatially than the volume of the intervertebral disc space 860 to be augmented or replaced. To compensate for the spatial discrepancy, in one variation, already described above, an expandable membrane or bladder is inserted in a relaxed, folded or unfilled state into the prepared space and the prosthetic nucleus material is injected or infused into the bladder, to expand the membrane in situ.

In another aspect, the expandable membrane comprises a moisture permeable expandable membrane. The expandable membrane is partially filled with a hydroscopic prosthetic nucleus material prior to axial deployment into the intervertebral disc space. Due to an infusion of moisture from physiologic fluid present in the disc space 860 through the moisture permeable expandable membrane, the prosthetic nucleus material subsequently swells in situ, leaving an expanded, semi-compliant prosthetic nucleus that provides distraction and maximum surface area in conformable contact with the intervertebral disc space 860 surfaces and structures. In some embodiments, this prosthetic nucleus may effectively distribute physiologic loads. In yet another variation, a partially filled permeable membrane may be pre-formed and sealed prior to deployment.

In some aspects of the present invention, the mobility preservation includes an expandable membrane configured to contain prosthetic nucleus material comprising hydrogels that are implanted or inserted in a dehydrated condition, for example by means of a glycerin carrier. The hydrogels are typically 3-dimensional structures consisting mainly of hydrophilic (i.e., very high affinity for water) polymeric materials or copolymers which retain water, without dissolving, within a network stability that is achieved through the presence of chemical or physical cross-links (e.g., entanglements; crystallites; primary covalent or secondary hydrogen, ionic, or Van der Waals bonds). In this manner, the overall bulk of the mobility preservation apparatus is reduced, allowing it to be inserted through a smaller access and the subsequent hydration, which results in an increase in volume of the hydrogel, may assist in disc distraction to at least partially restore disc height. In certain embodiments the prosthetic nucleus material may remain fluid, while in other embodiments, devices may be configured for deployment via minimal access, by introducing the hydrogel or polymeric material in a first state or condition (e.g., flowable), and to then allow or induce conversion of the material to a second phase or state, (e.g., to a solid). In this manner, the material can be introduced through the smallest possible access and yet still be provided in sufficient quantity to fill the disc space 860 and provide the desired function. Examples of methods to convert a material from a first flowable state to a second solid state include but are not limited to: a temperature phase change as from a melted state to a frozen state, polymerization of a monomer or low molecular weight polymer such as with the use of a catalyst; laser or UV cross-linking of a liquid polymer resulting in a solid; leaching of a solvent by replacing it with water (for example: polyacrylonitrile-polyacrylamide hydrogel can be dissolved in dimethylsulfoxide (DMSO) resulting in a flowable liquid which will instantly transform to a solid in the presence of water, into which the DMSO will preferentially flow); and use of reverse gelation polymers, such as Pluronic™, commercially available from BASF, Inc., Mount Olive, N.J. (USA), that are liquid at room temperature and form a solid at elevated temperatures such as body temperature, etc.

The specific configuration of the expandable membrane may vary depending on the intended treatment or function.

For example, in another embodiment of the present invention, the moisture-permeable expandable membrane is configured from a bioabsorbable material which remains in place to assume physiologic loads while the prosthetic nucleus material is swelling and the access site is healing.

In yet another aspect of the present invention, the expandable membrane is coated on its external surface with a therapeutic agent to be delivered, administered to the structures in which it is in conformal contact when fully filled and deployed.

In another embodiment, the expandable membrane component contains pre-inserted prosthetic nucleus material sealed therein. More specifically, the expandable membrane is configured as an envelope comprising tightly woven or knit fabric of polymeric fibers, e.g., Dacron™ or other material with a comparable tensile modulus. The envelope may be formed from other tightly woven, high molecular weight, high tenacity, flexible polymeric fabric e.g., high molecular weight polyethylene, polyester, polyolefin, polyethylene terephthalate, polytetrafluoroethylene, polysulfone, nylons, or any other high molecular weight, and other high tenacity materials including carbon fiber yarns, ceramic fibers, metallic fibers, etc. The fabric has pores that are small enough to confine the prosthetic nucleus material within the envelope while allowing passage (e.g., bi-directional) of low molecular weight hydration fluids or therapeutic agents. Preferably, the openings have an average diameter of approximately 10 micrometers, although other dimensions are acceptable. While the fabric is described as woven, any other configuration having a semi-permeable or microporous attribute can be used. The flexible material allows expansion and contraction of the hydrogel core (prosthetic nucleus material) in a controlled fashion. The hydrogel core serves to cushion the disc in the manner of the native nucleus pulposus more effectively when the envelope fabric is flexible and semi-compliant, having a burst strength that is greater than the swelling pressure of the hydrogel core when fully hydrated to prevent rending and loss of the hydrogel core. By having an envelope or jacket that is both flexible and semi-compliant, i.e., the elasticity being "modulus matched" to the native nucleus, the filled envelope is effective as a dampener, and properly assumes and distributes loads. When fully hydrated, an inelastic envelope expanded to its full capacity may not stretch or give when a load is applied and cannot deform, since the compression modulus in the normal load range is nearly vertical or incompressible, or distribute loads uniformly, thereby likely resulting in device subsidence and/or transition syndrome.

In another aspect, the expandable membrane comprises non-woven fibers, e.g., of a similar type used in the manufacture of Tyvek™ film.

In yet another aspect, a moisture-permeable polymeric expandable membrane may comprise a biaxially oriented membrane modified to be microporous by mechanical means, such as of laser drilling, or by chemical means, e.g., leaching out sacrificial salt particles to achieve a satisfactory end configuration.

In another aspect of the present invention, the expandable membrane containing the prosthetic nucleus material is configured to include an integral collar that extends axially about the expandable membrane and which is either secured to or integrally formed within the expandable membrane. The integral collar makes the expandable membrane is stiffer at its lateral surfaces than its inferior and superior surfaces. The expandable membrane with an integral collar may be deployed alone or in combination with a separate elastomeric collar that can abut the annulus. Mobility preservation apparatus with the integral collar may effectively functions as a prosthetic disc and provide the same load-bearing characteristics as the natural disc without undergoing the invasiveness of current total disc replacement procedures. The balance of compliancy and stiffness whether provided as a collar and/or as an expandable membrane with an integral stiffer component as previously described, enables the expanded expandable membrane to cushion a motion segment, without collapsing under compressive load. That is, the expanded expandable membrane with or without additional component provides dampening of instantaneous load, and also maintains effective surface area of conformal contact (congruent interface) between the mobility preservation apparatus and the annulus and the inferior and superior end plate surfaces, respectively. In turn, this yields a more uniform, radial distribution of loads to more closely approximate physiological load sharing. In accordance with this aspect of the present invention, the mobility devices disclosed herein are less likely to cause the phenomena of subsidence and/or transition syndrome. As used herein, subsidence refers to the detrimental descent of an orthopedic implant into bone that surrounds it. Transition syndrome refers to altered biomechanics and kinematics of contiguous vertebral levels and concomitant risk of adjacent motion segment instability that may occur as a result of spinal therapeutic procedures that are suboptimal in terms of their ability to restore physiological function and properties, and thus risk a cascading deleterious effect on surrounding otherwise healthy tissue.

In another variation of the present invention, the previously noted spatial discrepancy is obviated by prosthetic nucleus materials which are deployed directly into the denucleated space to augment or replace the intervertebral disc, after which the access tract is sealed in order to retain the prosthetic nucleus material by precluding migration or expulsion. More specifically, the prosthetic nucleus material, independent of an expandable membrane or envelope, may be introduced directly into the prepared intervertebral disc space, when the annulus is known to be intact. In this embodiment, the prosthetic nucleus material serves as the "air" in the "tire" of the disc, and is selected based on, among other attributes, including: biocompatibility; resistance to fractional mass loss over time and hence ability to provide or maintain distraction over time; distribute loads (hydrostatic pressure in the disc), for example. Further, the prosthetic nucleus material may be particularly selected to restore tensile hoop stress in the annulus. The selected prosthetic nucleus material may include biomedical grade hydrogels or blends thereof (e.g., hydrogel/hydrogel, or hydrogel/elastomer). Cross-linked hyaluronic acid, such as is available from Fidia Corporation in Italy, is an example of a suitable material, however, many natural and man-made hydrogels or blends thereof may be configured to achieve similar properties without inflammatory response. The efficacy of this embodiment for its intended function is further predicated on the requirement that the access site to the disc space 860 is sealed to preclude prosthetic nucleus material migration or expulsion. Any one of numerous valve configurations, e.g., self-sealing valve assemblies or flow-stop devices may suitably serve this function. Materials suitable for anchoring are similarly suitable as plugs, such as non-absorbable threaded plugs, including those fabricated from medical grade polyether-ether-ketone (PEEK) such as that commercially available from Invibio Inc., in Lancashire, United Kingdom, or polyether-ketone-ketone (PEKK) available from Coors-Tech Corporation, in Colorado, or alternatively, conventional polymethylmethacrylate (PMMA); ultra high molecular weight polyethylene (UHMWPE), or other suitable polymers in combination with autologous or allograft bone dowels may be used as plugs. One advantage of this embodiment would be the concomitant use of prosthetic nucleus material comprising hydrogels as in situ delivery vehicles for a range of therapeutic compounds (e.g., capitalizing on their biodegradability, through chemical hydrolysis or as enzymatically catalyzed). Moreover, certain bioactive hydrogels (e.g., such as those based on photo-crosslinked poly(ethylene oxide) [PEO], or block polypeptide or amino acid hydrogels), may be used to engineer tissue, e.g., cartilage; or to serve as a dimensional matrix that promotes nerve regeneration, or reduces scar tissue formation.

In another aspect of the present invention, the mobility preservation apparatus may both decompress the disc and alleviate pain usually caused by posterior nerve impingement, by either inducing slight segmental kyphosis or straight elevation; or by creating limits and/or resistance to segmental motion. In this manner, mobility preservation apparatus are able to provide both stable anterior and posterior load support (e.g., loads that may approximate 10 times the body weight of a patient) and adequate medial-lateral and rotational support, without adjunctive posterior instrumentation and without accompanying osteogenesis. Thus, unlike spinal fusion devices where accompanying osteogenesis results in permanent immobilization of the motion segment, the mobility preservation apparatus of the present invention may be revisable, and also convertible. That is, they may be explanted, replaced, or converted in the progression-of-treatment options from prosthetic nucleus to total disc replacement up to and including fusion. In certain embodiments of the present invention, the mobility preservation apparatus may include multiple, modular components which facilitate such convertibility. For example, a rod or plug may be inserted into the proximal end of a cannulated female inferior anchor portion. The plug may extend sufficiently through and distally into the fenestrated midsection of the elongated that the effective flexibility of the mobility preservation apparatus is compromised. If compromised sufficiently, the mobility preservation apparatus with the plug may now serve as an immobilization or fusion device. In addition, osteogenic materials may also be introduced through the into the intervertebral disc space 860 to facilitate the fusion of adjacent vertebrae.

In a yet another aspect of the present invention, the mobility preservation apparatus of the present invention is configured to include biocompatible materials that meet ISO 10993 standards for long-term implants, and/or are able to withstand, without wear, long term normal ranges of physiological loading. For example, the mobility preservation apparatus could withstand between about 1250 Newtons (N) (280 lbf) and 2250N (500 lbf) axial compression; 100 N (25 lbf) and 450N (100 lbf) of both lateral and sagittal shear, respectively, through full ROM over the lifetime of the mobility preservation apparatus, or up to about $40 \times 10^6$ cycles. Additionally, the mobility preservation apparatus of the present invention are preferably able to tolerate short term maximum physiological loads through full ROM of about 8000 Newtons (N) (1800 lbf) axial compression; about 2000 N (450 lbf) lateral shear; and about 3000 N (675 lbf) sagittal shear, over about 20 continuous cycles without failing. Yet another advantage of the mobility preservation apparatus of the present invention, in addition to sharing and distributing physiological loading and motion, is the ability to also assimilate forces artificially introduced in the event of ancillary therapeutic procedures, such as for example pedicle screw insertion.

In the context herein, "biocompatible" refers to an absence of chronic inflammation response when or if physiological tissues are in contact with, or exposed to (e.g., wear debris) the materials and devices of the present invention. In addition to biocompatibility, in another aspect of the present invention the materials of the mobility preservation apparatus are sterilizable; visible and/or imageable, e.g., fluoroscopically; or via CT (computed tomography), or MRI (magnetic resonance imaging). It will be understood that with MRIs, the materials must be substantially free of iron. Moreover, in consideration of contrast, detail, and spatial sensitivity, it is contemplated that contrast media or other materials (e.g., barium sulfate) may be employed in configuring mobility preservation apparatus when and where needed and appropriate, to supplement or modify radiolucency or radio-opaqueness.

It is another aspect of the present invention to provide spinal mobility preservation apparatus which preferably do not impede the mobility of, and are responsive to the physiological Instantaneous Center of Rotation (ICOR). Further, in one embodiment, the mobility preservation apparatus provides anterior-posterior translation and has a mobile ICOR. The mobility preservation apparatus of the present invention may not adversely impact the stiffness of the motion segment being treated. For example, mobility preservation apparatus axially deployed in the L5-S1 lumbar spine may enable/accommodate a range of motion of between about 10° to 15° flexion; between about 7° to about 10° extension; about 4° to about 9° of left or right lateral bending and between about 1° to about 2° clockwise or counterclockwise axial rotation. Mobility preservation apparatus implanted in L4-L5 may enable/accommodate a range of motion of between about 8° to 10° flexion; between about 5° to about 7° extension; between about 4° to about 9° left or right lateral bending; and between about 1° to about 4° clockwise or counterclockwise axial rotation.

In yet another aspect of the present invention, mobility preservation apparatus may be configured to manage mobility by controlling resistance to motion. This can be accomplished by varying stiffness which may be accomplished by varying cross-sectional area and other features, and hence stiffness. In addition or alternatively, mobility preservation apparatus may be configured to create limitations to motion. This can be accomplished by incorporation of at least one mechanical stop. As used herein, "resistance" refers to the force required to move through a full range of motion, whereas in contrast, "limitation" refers to not force but degree, i.e., curtailment of full range of motion in one or more directions.

Thus, in one aspect of the present invention, mobility preservation apparatus may be configured to restore full and/or unconstrained range of motion, but in general the expanded expandable membranes function to restore mobility rather than control or manage motion. In contrast, yet another aspect of the present invention includes mobility preservation apparatus which provide motion management. The mobility preservation apparatus which provide motion management may allow a semi-constrained range of motion where full range of motion is allowed in combination with increased resistance to motion; or a limited range of motion wherein the extent of motion in one or more degrees of freedom is mechanically limited, with or without increased resistance to motion. The mobility preservation apparatus which provide motion management may be configured to include expandable membranes, and hence incorporate the mechanical functions of a prosthetic nucleus material.

Yet another aspect of the present invention to provide spinal mobility preservation apparatus that induces and maintains maximum distraction while being implantable and functional within a wide range in anatomies. In one embodiment, mobility preservation apparatus provide from between about 2 mm to about 10 mm, of distraction, and can accommodate physiological lateral disc diameter from between about 15 mm up to about 50 mm; sagittal disc diameter from between about 10 mm up to about 40 mm (i.e., in the median plane between the anterior and posterior sides); disc heights from between about 5 mm and about 15 mm; and "wedge angles" from between about 5 degrees and about 15 degrees. As used herein, wedge angle refers to the relative angle of the faces of the inferior and superior vertebral endplates of a motion segment, one to the other.

In certain aspects, the present invention may involve surgical tools sets and methods for accessing and preparing vertebral elements, such as inter-vertebral motion segments located within a human lumbar and sacral spine for therapeutic procedures. In the context of the present invention, "motion segments" comprise adjacent vertebrae separated by intact or damaged spinal discs.

In particular embodiments of the present invention, instrumentation system components and their methods of use, individually and in combination and over or through one another, form or enlarge a posterior or anterior percutaneous tract; access, fragment and extract tissue (e.g., nucleus pulposus,); or otherwise prepare vertebral elements and inter-vertebral motion segments for dynamic stabilization via implantation of therapeutic procedures and spinal devices. Instrumentation may be introduced and aligned through the percutaneous pathways and according to the trans-sacral axial access methods. The alignment may be accomplished using biplane fluoroscopy, endoscopy, or other radio-imaging methods, as guidance to insure that the channel is positioned mid-line to the anterior/posterior and lateral sacral view.

Certain of the surgical tools take the form of elongated solid body members extending from proximal to distal ends thereof. Such solid body members may be used in combination or sequentially with elongated, cannulated body members. Hence, for example, design constraints, in addition to outside diameter (O.D.) tolerances and limitations imposed by virtue of patient anatomies, such as tube wall thickness, material selection/mechanical strength, and inside diameter (I.D.) also become considerations, e.g., to enable unrestricted passage over guide members or through hollow body members without incurring deformation that may impair or otherwise preclude intended function. Certain of these solid body and hollow body members can have distal means, mechanisms, or apertures that may be configured or manipulated for either precluding or facilitating engagement with tissue; the latter including piercing; tapping; dilating; excising; fragmenting; extracting; drilling; distracting (e.g. elevating); repairing; restoring; augmenting; tamping; anchoring; stabilizing; fixing, or fusing tissue. Certain of these solid body and hollow body members can have proximal means, mechanisms, pins, slots or apertures that may be configured or manipulated to engage; grasp; twist; pilot; angle; align; extend; expose, retract; drive; attach or otherwise interact to enable or facilitate the functionality of other components within the surgical tools set, e.g., the distal means and mechanisms noted above in this paragraph. Moreover, in accordance with the present invention the individual components comprised in the tools sets, or kits, may include a guide pin introducer; guide pins with various distal end and proximal end configurations (e.g., tips; handles, respectively); soft tissue and bone dilators and dilator sheath(s); cutters; tissue extraction tools; twist drills; an exchange rod and exchange cannula system; distraction tools; augmentation, and repair tools.

In a particularly preferred procedure, these instrumentation system components are visualization aligned axially, and progressively inserted into a human lumbar-sacral spine through the minimally invasive percutaneous entry site adjacent the coccyx to access the S1-L5 or L4 disc space 860 to perform a partial or total nucleectomy, without compromising the annulus fibrosis, unlike current surgical discectomy procedures. Conventional discectomies are performed through a surgically created or enlarged hole in the annulus that remains post-operatively, and represents a contraindicated pathway for extrusion and migration of natural or augmented tissue, or implants, and that also compromise the biomechanics of the physiological disc structure.

Moreover, in accordance with the techniques and surgical tool sets, and in particular the cutters and extraction tool configurations of the present invention, a substantially greater amount (volume) of nucleus pulposus by, in comparison with other non-open discectomy procedures in practice, may be removed, as needed. In particular, the instrumentation systems and techniques embodied in the present invention more effectively, with less immediate trauma, and without residual negative physiological impacts that may occur as a result of invasion of the annulus, prepare an inter-vertebral motion segment for subsequent receipt of therapeutic procedures, and enables axial placement of implants close to and in alignment with the human spine's physiological center of rotation.

Other specific advantages over current practice may include: the patient is in a prone position that is easily adaptable to other posterior instrumentation; blood loss is minimal; soft tissue structures, such as veins, arteries, nerves may be are preserved; substantially less surgical & anesthesia time is required compared with conventional procedures; and the implants of the present invention may restore function not merely alleviate pain. These and other advantages and features of the surgical tools sets and techniques disclosed in the present invention will be more readily understood from the following detailed description of the preferred embodiments thereof, when considered in conjunction with the accompanying figures.

BRIEF DESCRIPTION OF THE DRAWINGS

FIG. 4 illustrates a proximal end view of an embodiment of a mobility preservation apparatus;

FIG. 5 illustrates a perspective view of an embodiment of a mobility preservation apparatus with an expandable membrane in the expanded position;

FIG. 6 illustrates a cross-section of a side view of an embodiment of a mobility preservation apparatus having a unitary elongated body with an expandable membrane in an unexpanded position;

FIG. 7 illustrates a cross-section of a side view of an embodiment of a mobility preservation apparatus having a unitary elongated body with an expandable membrane in an expanded position;

FIG. 11 illustrates a perspective view of an embodiment of a mobility preservation apparatus with the expandable membrane in an expanded position;

FIG. 12 illustrates a cross-section of a side view of an embodiment of a mobility preservation apparatus with the expandable membrane in an unexpanded position;

FIG. 13 illustrates a cross-section of a side view of a single anchor prosthetic nucleus apparatus with the expandable membrane in the expanded position;

FIG. 14 illustrates a cross-section of a side view of an embodiment of a mobility preservation apparatus with a cable design for the flexible element;

FIG. 24 illustrates a partial cross-section of an embodiment of the proximal body of a mobility preservation apparatus in accordance with the present invention with a driver positioned to axially rotate the mobility preservation apparatus being inserted into a bore within a vertebral body;

FIG. 25 illustrates a partial cross-section of an embodiment of a mobility preservation apparatus in accordance with the present invention axially positioned between vertebral bodies of a spinal motion segment;

FIG. 28 illustrates a partial cross-section of an embodiment of a mobility preservation apparatus in accordance with the present invention without an expandable membrane which is axially positioned between vertebral bodies of a spinal motion segment after prosthetic nucleus material has substantially filled the intervertebral disc space;

FIG. 29 illustrates a cross-section of a side view of an embodiment of a mobility preservation apparatus having single body positioned within a vertebral body and with the expandable membrane expanded within the intervertebral disc space;

FIG. 30 illustrates a partial cross-section of an embodiment of a mobility preservation apparatus having an embodiment of a preformed prosthetic nucleus in accordance with the present invention being positioned through the mobility preservation apparatus and into an intervertebral disc space;

FIG. 31 illustrates top view of an embodiment of a preformed prosthetic nucleus in accordance with the present invention;

FIG. 32 illustrates a top view of a cross-section of an embodiment of a mobility preservation apparatus in accordance with the present invention axially positioned between vertebral bodies of a spinal motion segment;

FIG. 33 illlustrates a partial cross-section of an embodiment of a mobility preservation apparatus in accordance with the present invention axially positioned between vertebral bodies of a spinal motion segment with an unexpanded the expandable membrane; and FIG. 34 illustrates a partial cross-section of an embodiment of a mobility preservation apparatus in accordance with the present invention axially positioned between vertebral bodies of a spinal motion segment after prosthetic nucleus material has at least partly expanded the expandable membrane.

DETAILED DESCRIPTION OF THE INVENTION

Figure 1:
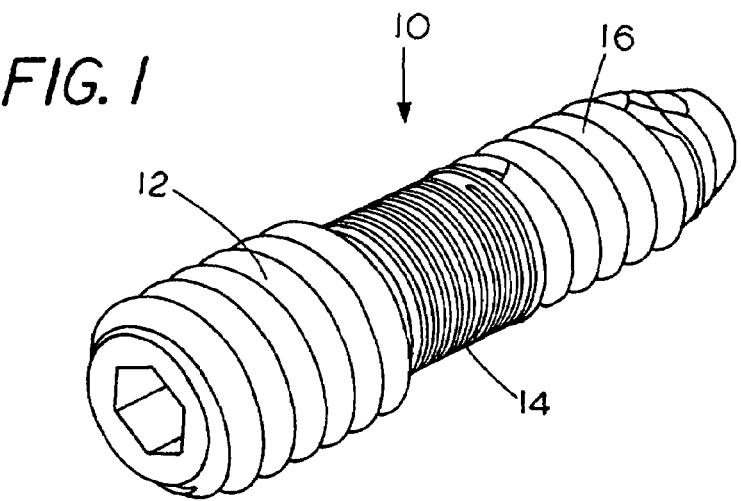
FIG. 1 illustrates a perspective view of an embodiment of a mobility preservation apparatus without an expandable membrane.

Embodiments of mobility preservation apparatus 10 in accordance with the present invention are generally illustrated throughout the figures for exemplary purposes. A mobility preservation apparatus 10 are generally configured as an elongated body that is substantially radially symmetrical about its longitudinal axis as illustrated throughout the figures. A mobility preservation apparatus 10 may include a proximal body 12, an intermediate body 14, a distal body 16 and an expandable membrane 18 operatively connected to one another as discussed below. In accordance with the present invention, mobility preservation apparatus 10 are generally configured to be implanted axially within the spine. More particularly, mobility preservation apparatus 10 may position at least a portion of the mobility preservation apparatus 10 in the disc space 860 between two adjacent vertebrae when positioned within a patient. The mobility preservation apparatus 10 may carry at least a portion of the load which would normally be transferred to a healthy intervertebral disk. In one aspect, the adjacent vertebrae may be S1 and L5.

Various configurations and embodiments of mobility preservation apparatus 10 are illustrated throughout the figures. A mobility preservation apparatus 10 are typically formed or configured as a one, two, or three piece elongated body or may be otherwise configured as will be apparent to those skilled in the art upon review of the present disclosure. The mobility preservation apparatus 10 may be configured as an elongated body that is substantially radially symmetrical about its longitudinal axis. In one embodiment, a mobility preservation apparatus 10 may include a body 12 secured to an expandable membrane 18. In another embodiment, a mobility preservation apparatus 10 may include a proximal body 12 and a distal body 16 secured to an expandable membrane 18. In yet another embodiment, the mobility preservation apparatus 10 may include a proximal body 12 and distal body 16 with the proximal body 12 and distal body 16 secured to one another by an intermediate body 14 with at least a portion of the intermediate body including a flexible element 22. In still another embodiment, the mobility preservation apparatus 10 may include a proximal body 12 and distal body 16 with the proximal body 12 and distal body 16 secured to one another by an intermediate body 14 and the intermediate body including an expandable membrane 18.

As illustrated for exemplary purposes in FIGS. 24 to 30, 32 33 and 34, mobility preservation apparatus 10 may be secured to and extend between adjacent caudad and cephalad positioned vertebral bodies. The mobility preservation apparatus 10 is typically positioned at the approximate center of movement between the two vertebral bodies. The mobility preservation apparatus 10 may be generally configured for axial implantation through a longitudinal bore 850 in a vertebral body and at least partially into or through a disc space 860 resulting from the nucleectomy procedure. The implantation of embodiments of a mobility preservation apparatus 10 may be enabled following partial or complete nucleectomy and temporary distraction. As used herein, temporary distraction refers to the elevation of disc height relative to an adjacent disk. A mobility preservation apparatus 10 may be inserted into an elevated disc space 860 or may itself elevate the disc space 860 and, thereafter, may preserve that height space. Suitable surgical instrumentation systems and techniques for access, distraction and implantation using an anterior transsacral axial approach are disclosed in commonly assigned U.S. patent applications having Ser. Nos. 10/309,416; 10/125,771; 09/848,556; and 60/182,748, and U.S. Pat. Nos. 6,558,386; 6,558,390; 6,575,979; and 6,790,210, the disclosures of which are hereby incorporated by reference. Those skilled in the art will recognize additional methods for implantation of a mobility preservation apparatus 10 upon review of the following disclosure and the attached figures.

A mobility preservation apparatus 10 implanted by the above referenced methods may decompress the disc and alleviate pain caused by nerve impingement, usually posterior, either inducing slight segmental kyphosis or straight elevation, and/or by creating limits and resistance to segmental motion. In this manner, mobility preservation apparatus 10 may be able to provide both stable anterior and posterior load support and a degree of medial-lateral and rotational support, without adjunctive posterior instrumentation and without accompanying osteogenesis. In some exemplary embodiments, a mobility preservation apparatus 10 may be configured to support loads that may approximate ten (10) times the body weight of a patient.

A mobility preservation apparatus 10 may be generally configured to provide some degree of dynamic stabilization. In the context of the present invention, dynamic refers to non-static devices with an inherent ability to allow mobility by enabling or facilitating forces or load bearing that assist or substitute for physiological structures that are otherwise compromised, weakened or absent. More specifically, certain embodiments of mobility preservation apparatus 10 are disclosed which eschew immobilization in favor of providing dynamic stabilization. By design, some of these embodiments may resist and limit of motion in a controlled manner. As used in this context, "resist" or "resistance" refers to the force required to move through a full range of motion, whereas in contrast, "limit" or "limitation" refers to not force but degree. That is, "limit" or "limitation" refers to curtailment of full range of motion in one or more directions. With respect to the lumbar spine, the normal full range of motion typically allows for about twelve (12) degrees of flexion, about eight (8) degrees of extension, about nine (9) degrees of left or right lateral bend, and about 2 degrees of clockwise or counterclockwise motion. Thus, mobility preservation apparatus 10 may be configured to include, for example, a mechanical stop(s) to limit motion, and/or provide resistance to motion beyond a desired range.

Thus, for example, mobility preservation apparatus in accordance with the present invention which have been configured for the lumbar spine generally can permit at least about four (4) degrees, often at least about eight (8) degrees and preferably no more than about twelve (12) degrees or fourteen (14) degrees of flexion. The device will generally permit at least about four (4) degrees, often at least about six (6) degrees and preferably no more than about eight (8) degrees or ten (10) degrees of extension. The device will generally permit at least about 0.5 degrees, often at least about one (1) degree and preferably no more than about two (2) degrees or three (3) degrees of rotation, depending upon the desired clinical performance. With respect to the spine generally, mobility preservation apparatus 10 in accordance with the invention may provide up to about 100% or 125% of the normal full range of motion for any particular motion segment being treated. Endpoints to the range of motion may either be abrupt, such as by the use of first and second complementary mechanical stop surfaces, or may be dampened by an increase in resistance to further motion.

In one aspect, resistance to motion may be altered by varying cross-sectional area and hence stiffness, any of a variety of gradual ramps, friction surfaces or gradual dimensional mismatches, or other biomechanical properties relevant to preserving or restoring physiological function with respect to mobility. In various embodiments, the mobility preservation apparatus 10 may be designed to provide full, unconstrained (e.g., beyond the normal anatomical) range of motion, semi-constrained (e.g., approximately normal anatomical) range of motion where full range of motion is allowed in combination with increased resistance to motion, or limited range of motion wherein the extent of motion in one or more degrees of freedom is mechanically limited, with or without increased resistance to motion.

With particular respect to a mobility preservation apparatus 10 incorporating the ball and track configuration as a flexible element 22, discussed below, the mobility preservation apparatus 10 may be configured for the lumbar spine generally will permit at least about 4 degrees, often at least about 8 degrees and preferably no more than about 20 degrees of flexion (bending forwards). The mobility preservation apparatus 10 will generally permit at least about 4 degrees, often at least about 6 degrees and preferably no more than about 20 degrees of extension (bending backwards). Rotation is unconstrained through normal range of motion.

In one embodiment, the mobility preservation apparatus 10 may approximate the biomechanical properties of the physiological vertebal or disc structure(s) depending on the particular function(s) for which therapeutic procedure(s) are indicated. In one aspect, the mobility preservation apparatus 10 may be substantially matched bulk and compression modulus. As used herein, this is referred to as modulus matched. Further, a series of mobility preservation apparatus 10 providing dynamic stabilization may be provided across a progression-of-treatment for treating symptomatic discogenic pain, ranging from treatment in patients where little degeneration or collapse is evident radio-graphically, or other conditions for which additional spinal support may be beneficial.

In another aspect, a mobility preservation apparatus 10 is configured to mechanically and adjustably, distract a disc space 860 and is configured to subsequently be deployed so that it is oriented in approximately the line of principal compressive stress. For example, the mobility preservation apparatus 10 may be configured to be placed at approximately the center of rotation in a human disc motion segment. Moreover, the mobility preservation apparatus 10 may configured to be deployable without compromising the annulus and to dissipate and share physiologic loads with the normal load bearing biological structures. These load bearing structures will typically include the annulus and the nucleus pulposus, either alone or in combination.

In an exemplary configuration having at least a proximal body 12 and a distal body 16, the overall length of mobility preservation apparatus 10 may range from about 40 mm to about 60 mm. Typically, the mobility preservation apparatus 10 will have an aspect ratio of at least one. Typically, the proximal body 12 and distal body 16 will be substantially coaxially aligned to facilitate the axial implantation of mobility preservation apparatus 10 through a bore 860 in a vertebral body. The aspect ratio measured as the ratio of the overall length to the largest diameter along the length. Proximal body 12 and distal body 16 are typically sized and configured based on size, weight and support needs for a particular patient as will be recognized by those skilled in the art upon review of the present disclosure. In some exemplary embodiments for threaded bone anchors, a smaller mobility preservation apparatus may include a proximal body 12 having first threads 32 with a major thread diameter of about 0.5" and a minor thread diameter of about 0.4", and a distal body 16 having second threads 36 with a major thread diameter of about 0.4" and a minor thread diameter of about 0.2". A larger mobility preservation apparatus 10 may include a proximal body 12 having first threads 32 with a major thread diameter of about 0.6" and a minor thread diameter of about 0.4", and a distal body 16 having second threads 36 with a major thread diameter of about 0.43" and a minor thread diameter of about 0.3". Frequently, the major thread diameters range from about 0.25" to about 0.75", and minor thread diameters range from about 0.125" to about 0.5". However, the sizes and relative proportions may be varied as required for particular patients and applications.

The proximal body 12, intermediate body 14, and distal body 16 can be formed from a wide range of materials that will be recognized by those skilled in the art upon review of the present disclosure. In one aspect, the material may be a metal alloy such as, Ti6Al4V, Elgiloy™ (a super alloy of cobalt chrome), MP35N, stainless steel, or other materials according to the biomechanical properties being selected by design. Typically, the alloy will be selected for high tensile strength, which may be greater than 300,000 pounds per square inch, as well as high fatigue strength. The components may also be formed from a biocompatible material selected for its abrasion and/or wear resistant, such as for example cobalt chrome superalloys, such as Stellite™, available from Deloro Stellite, Inc., distributed from Goshen, Ind. In another aspect, the mobility preservation apparatus 10 may be configured from a biocompatible polymeric material, such as for example, polyether-ether-ketone (PEEK) or polyether-ketone-ketone (PEKK). In other aspects, the mobility preservation apparatus may be constructed from polymers, metals, and other materials or combinations of materials with suitable biomechanical properties to engage the vertebral body and withstand the loads transferred to the mobility preservation apparatus 10.

Figure 27:
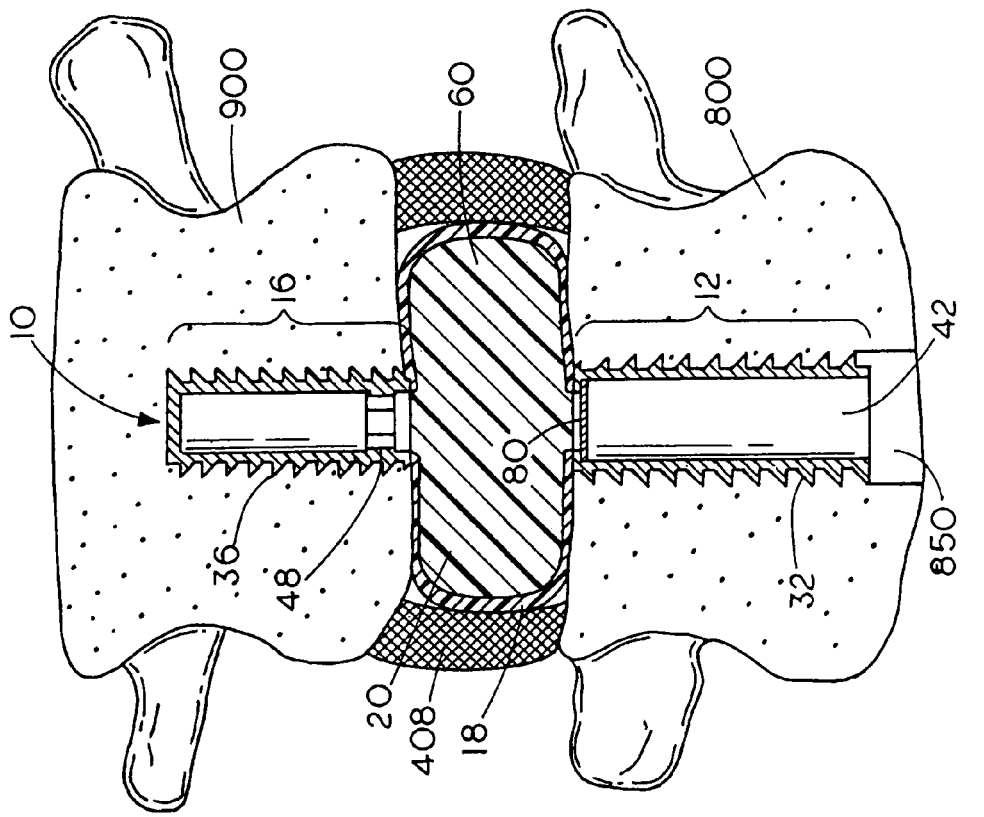
FIG. 27 illustrates a partial cross-section of an embodiment of a mobility preservation apparatus in accordance with the present invention axially positioned between vertebral bodies of a spinal motion segment after prosthetic nucleus material has expanded the expandable membrane.
Figure 26:
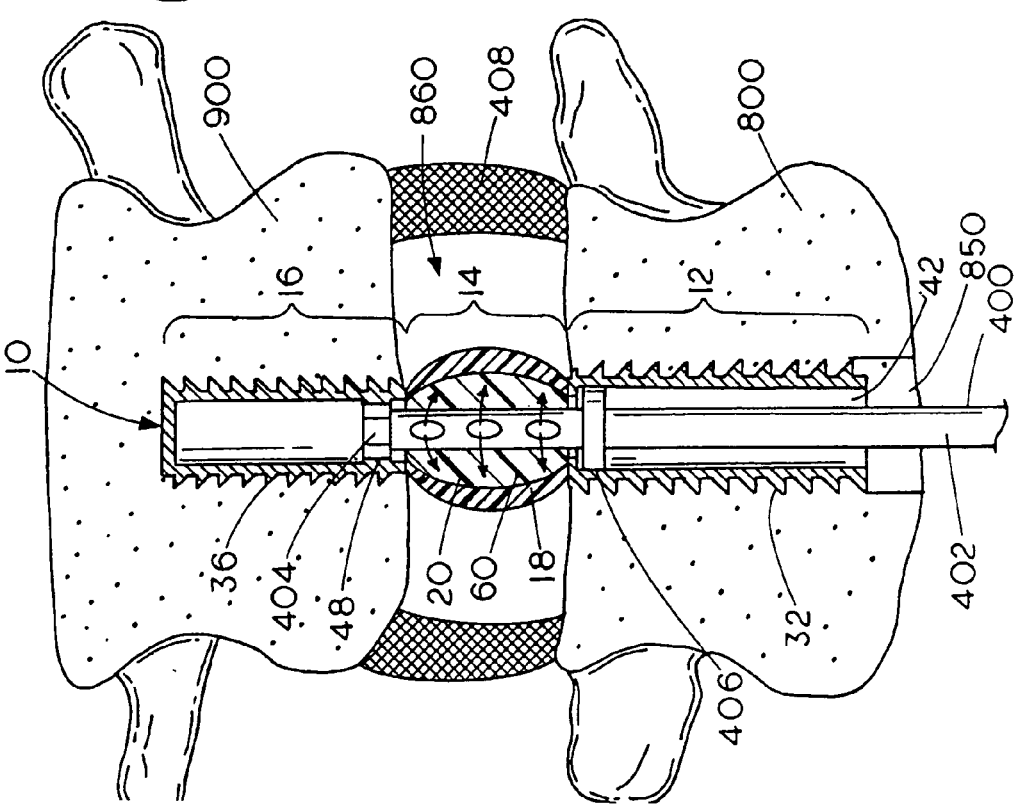
FIG. 26 illustrates a partial cross-section of an embodiment of a mobility preservation apparatus in accordance with the present invention axially positioned between vertebral bodies of a spinal motion segment after prosthetic nucleus material provided through the introducer has at least partially expanded the expandable membrane.

In embodiments including a proximal body 12 and distal body 16, the mobility preservation apparatus 10 is generally configured to extend between adjacent cephalad and caudad vertebral bodies, such as for example between the vertebral bodies of the L5 and S1 vertebrae. Exemplary positioning of such embodiments is illustrated in FIGS. 25 to 28, 30, and 32 to 34. Proximal body 12 is generally configured to secure the proximal end of mobility preservation apparatus 10 to a caudad positioned vertebral body 800. Accordingly, the proximal body 12 will typically include a first retention structure 32. For exemplary purposes, first retention structure 32 has been illustrated as a first thread 32 formed on the exterior surface of the proximal body 12 throughout the figures. The first retention structure 32 is configured to secure proximal body 12 in a bore 850 through a caudad vertebral body 800, as illustrated in FIGS. 26 and 27. In another aspect, first retention structure 32 of proximal body 12 may be configured to be compressionally or slidably secure proximal body 12 within bore 850. In yet another aspect, the first retention structure 32 may include an ingrowth structure to promote bone ingrowth to secure proximal body 12 within bore 850. Additional configurations for first retention structure 32 will be evident to those skilled in the art upon review of the present disclosure. The proximal body 12 may define a proximal lumen 42. In certain embodiments, the proximal lumen 42 may function as access port and may reside along the longitudinal axis. The proximal lumen 42 may extend coaxially from the proximal end to the distal end of proximal body 12.

Distal body 16 is generally configured to secure the distal end of mobility preservation apparatus 10 to a cephalad positioned vertebral body 900. Accordingly, the distal body 16 will typically include a second retention structure 36. For exemplary purposes, second retention structure 36 has been illustrated as a second thread 36 formed on the exterior surface of the distal body 16 throughout the figures. The second retention structure 36 is configured to secure distal body 16 in a bore 850 through a cephalad vertebral body 900, as illustrated in FIGS. 26 and 27. In another aspect, second retention structure 36 of distal body 16 may be configured to be compressionally or slidably secure distal body 16 within bore 850. In yet another aspect, the second retention structure 36 may include structure to promote bone ingrowth to secure distal body 16 within bore 850. Additional configurations for second retention structure 36 will be evident to those skilled in the art upon review of the present disclosure. The distal body 16 may define a proximal lumen 42. The proximal lumen 42 may extend coaxially from the proximal end to the distal end of distal body 16.

In some embodiments, the intermediate body 14 is an intermediate portion that bridges the proximal body 12 and distal body 16. The intermediate body 14 may be configured to assimilate forces or redistribute loads incurred between adjacent vertebrae. The intermediate body 14 is typically secured at a proximal end to the proximal body 12 and at a distal end to the distal body 16. In one aspect, the proximal body 12, the intermediate section 14 and the distal body 16 may be formed from a single piece of material. The intermediate body 14 may include an intermediate lumen 44. Intermediate lumen 44 may extend from the proximal end to the distal end of the intermediate body 14 or may extend to the proximal end of the intermediate body 14 and be in fluid communication with one or more fenestrations 74, discussed below. In one aspect, the intermediate lumen 44 may extend coaxially from the proximal end to the distal end of intermediate body 14.

The intermediate body 14 typically includes a flexible element 22 to permit a limited degree of movement between the relative positions of the proximal body 12 and the distal body 16. The flexible element 22 can comprise at least a portion of the intermediate body 14 and may be coextensive with the intermediate body 14. The flexible element 22 of intermediate body 14 may include a cable, a spring, a helical flexure, a notched flexure, stacked-washers, a ball and track configuration, or a combination thereof, or other flexible members to serve as a "shock absorber," a point of articulation and/or a pivot point for movement of adjacent vertebrae secured to the mobility preservation apparatus 10. When the flexible element 22 of intermediate body 14 is a spring or helical flexure, the helical flexure is typically configured to support a static load of between 10 lbs and 300 lbs at 1 mm of deflection. Typically, the helical flexure is configured to support a static load of between 50 lbs and 200 lbs at 1 mm of deflection. In an exemplary embodiment, the helical flexure is configured to support about 100 lbs. at 1 mm deflection. The load supported by a helical flexure may be modified, by changing the number of coils per turn, changing the spring constant, and/or by altering "waist" diameter of the helical flexure.

Further, the intermediate body 14 may define one or more fenestrations 74 through which a prosthetic nucleus material 60 may be inserted into an expansion chamber 20 defined by the expandable membrane 18. In other aspects, the fenestrations 74 may relate solely to the function of flexible element 22. As discussed above, fenestrations 74 may be in fluid communication with an intermediate lumen 44 defined by intermediate body 14. The intermediate lumen 44 may extend coaxially from the proximal end of the intermediate body 14 to the fenestrations 74. In other embodiments, intermediate lumen 44 extends from the proximal end to the distal end of intermediate body 14. Further, intermediate lumen 44 may be coaxial and in communication with the proximal lumen 42 when intermediate section 14 is secured to proximal body 12.

The expandable membrane 18 is generally configured to expand into the disc space 860 to provide a degree of support to adjacent vertebral bodies 800, 900. The expandable membrane 18 may define an expansion chamber 20. In one aspect, the expansion chamber 20 may be defined with the expandable membrane 18 in a relaxed position. In other aspects, the expansion chamber 20 is only defined when the expandable membrane 18 is at least in part expanded. The expandable membrane 18 is typically expanded in situ by the addition and/or hydration of a prosthetic nucleus material 60 into and/or in an expansion chamber 20 as illustrated in FIGS. 26 and 27. The expandable membrane 18 may maintain the position of the prosthetic nucleus material 60 within the expansion chamber 20. The expandable membrane 18 may be configured to assimilate forces or redistribute loads incurred between adjacent vertebrae when in an expanded configuration. The expandable membrane 18 is typically configured to circumferentially extend about or from the longitudinal axis of at least a portion of the proximal body 12, the intermediate section 14 and/or the distal body 16. In one aspect, the expandable membrane 18 may be configured to inflate within the disc space 860 until it comformably contacts all or substantially all of the surfaces within the disc space 860. In the expanded position, expandable membrane 18 may be configured to functionally reproduce the same load-bearing characteristics as the natural disc's nucleus pulposus. In this manner, a mobility preservation apparatus 10 may preserve and restore mobility to a spinal motion segment. In embodiments with an intermediate body 14, the expandable membrane 18 is typically configured to circumferentially extend about the longitudinal axis of at least a portion of the intermediate body 14. In this embodiment, the expandable membrane 18 may be configured as a tube that extends from the proximal body 12 to the distal body 16 with the intermediate body 14 extending through the lumen of the tube. In this configuration, the inner surface of the tube will define the expansion chamber 20 as prosthetic nucleus material 60 is infused into the mobility preservation apparatus 10.

In embodiments without an intermediate body 14 of elongated body 12, the expandable membrane 18 is typically configured to function as the intermediate body 14 by connecting proximal body 12 to distal body 16. In this embodiment, the expandable membrane 18 may be configured as a tube extending between the proximal body 12 and distal body 16 to which it is secured. Again, in this configuration, the inner surface of the tube will define the expansion chamber 20 as prosthetic nucleus material 60 is infused into the mobility preservation apparatus 10. In embodiments with only a single proximal body 12, the expandable membrane 18 may be secured to an end of the proximal body 12. The expandable membrane 18 may expand outward from the end of the proximal body 12 to contact intervertebral disc space 860 left by a nucleectomy procedure. In this embodiment, the expandable membrane 18 is similar to a balloon with the inner surface of the balloon defining the expansion chamber 20.

The expandable membrane 18 is typically formed from an elastomeric material having desired expandability, flexibility and durability characteristics. The expandable membrane 18 may be formed from an elastomeric material that is deployable, stable and biocompatible. The elastomeric material may have a durometer shore A hardness in the range of substantially about 20-90. In certain configurations as will be recognized by those skilled in the art, this range of durometer shore A hardness will result in a compliant membrane. One example of a suitable elastomeric material is silicone rubber exhibiting elongation of between about 500% and about 1500%, and most preferably at about 1000%, and having a wall thickness of 0.220". The specific configuration and physical properties of the expandable membrane may vary depending on the intended treatment or function. For example, the expandable membrane 18 may be configured from a moisture-permeable bioabsorbable material which could remain in place to assume physiologic loads while the prosthetic nucleus material 60 is swelling and the access site is healing. The expandable membrane 18 may also be coated with a therapeutic agent to be delivered, administered to the structures in which it is in conformal contact when fully filled and deployed. In one exemplary embodiment, the therapeutic agent could be coated on the external surface of the expandable membrane.

Figure 21:
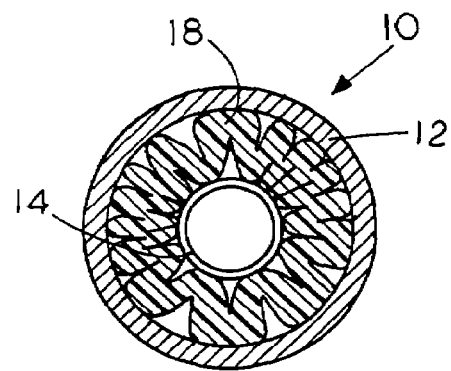
FIG. 21 illustrates a cross-section of an end view through the intermediate body of an embodiment of the expandable membrane as a folded envelope.

In another embodiment, the mobility preservation apparatus 10 is configured as a pre-formed expandable membrane 18 component containing pre-inserted prosthetic nucleus material 60 sealed within an expansion chamber 20. More specifically, the expandable membrane 18 may be configured as an envelope comprising tightly woven or knit fabric of polymeric fibers, such as for example Dacron™ or other material with a comparable tensile modulus. The expandable membrane 18 configured as an envelope may be folded about the intermediate body 14 as illustrated in FIG. 21 for implantation purposes. The envelope may be formed from other tightly woven, high molecular weight, high tenacity, flexible polymeric fabric, such as for example high molecular weight polyethylene, polyester, polyolefin, polyethylene terephthalate, polytetrafluoroethylene, polysulfone, nylons, or any other high molecular weight, and other high tenacity materials including carbon fiber yarns, ceramic fibers, metallic fibers, etc. The fabric may have pores that are small enough to confine the prosthetic nucleus material within the envelope while allowing passage (unidirectional or bi-directional) of low molecular weight hydration fluids or therapeutic agents. In one exemplary embodiment, the openings have an average diameter of approximately 10 micrometers, although other dimensions are acceptable. While the fabric is described as woven, any other configuration having a semi-permeable or microporous attribute can be used. The selected material may allow for expansion and contraction of the prosthetic nucleus material 60 in a controlled fashion. The prosthetic nucleus material 60 may more effectively cushion the disc in the manner of the native nucleus pulposus when the envelope fabric is flexible and semi-compliant. Typically, the fabric will have a burst strength that is greater than the swelling pressure of the prosthetic nucleus material 60 when fully hydrated to prevent rending and loss of the hydrogel core. By having an envelope or jacket that is both flexible and semi-compliant, and, in some instances, with the elasticity being modulus matched to the native nucleus, the filled envelope can be effective as a dampener, and may properly assume and distribute loads. When fully hydrated, an inelastic envelope expanded to its full capacity may not stretch or give when a load is applied and cannot deform, since the compression modulus in the normal load range is nearly vertical or incompressible, or distribute loads uniformly, thereby likely resulting in device subsidence and/or transition syndrome.

In yet another embodiment, the expandable membrane 18 may be composed of non-woven fibers. These non-woven fibers may be of a similar type to those used in the manufacture of Tyvek™ film. In another embodiment, a moisture-permeable polymeric expandable membrane 18 may comprise a biaxially oriented membrane modified to be microporous by mechanical means, such as of laser drilling, or by chemical methods. In one aspect, the chemical methods may involve the leaching out of sacrificial salt particles to achieve a satisfactory end configuration. These chemical methods may result in openings in the 10 micrometer range. Under certain conditions, such end configurations may promote tissue ingrowth.

In another embodiment, the expandable membrane 18 is composed of a moisture permeable material that is partially filled with a prosthetic nucleus material 60 prior to axial implantation and deployment into the prepared space. The expandable membrane 18 may also be sealed prior to implantation. The prosthetic nucleus material 60 of this variation will typically be hydroscopic. Due to an infusion of moisture from physiologic fluid present in the disc space 860 through the moisture permeable material of the expandable membrane 18, the prosthetic nucleus material 60 swells in situ, to expand a semi-compliant expandable membrane 18. The expanded expandable membrane 18 may then provide distraction and maximum surface area. In some aspects, the expandable membrane 18 may expand to conformably contact the surfaces and structures of the intervertebral disc space 860. Accordingly, the expandable membrane 18 may effectively distribute physiologic loads.

In embodiments with at least a proximal body 12 and a distal body 16, the expandable membrane 18 is typically sealing secured one or more of the proximal body 12, distal body 16 and the intermediate body 14. In one aspect, the expandable membrane 18 is sealing secured at its proximal end to the distal end of proximal body 12 and at its distal end to the proximal end of distal body 16. In another aspect, the expandable membrane 18 is sealingly secured at its proximal end about the proximal end of the intermediate body 14 and at its distal end about the distal end of the intermediate body 14. When fenestrations 74 are included on the intermediate body 14, expandable membrane 18 is typically secured at locations both proximal and distal to any fenestrations 74 or other passages through which prosthetic nucleus material 60 may pass to expand of the expandable membrane 18. In embodiments with only a proximal body 12, expandable membrane 18 is typically attached to the distal end of the proximal body 12 and is in fluid communication with proximal lumen 42 for purposes of expansion.

The expandable membrane 18 may be mechanically, chemically or otherwise secured to one or more of the proximal body 12, distal body 16 and the intermediate body 14. In one aspect, retainer rings may be provided about the expandable membrane 18 to secure the expandable membrane 18 to the adjacent components as illustrated in FIGS. 5 to 10, 12, 13, 19 and 20. FIGS. 5 to 13 illustrate some details of embodiments for securing the expandable membrane 18 to or into the adjacent structure. Typically, a first retainer ring 52 will secure the proximal end of the expandable membrane 18 and a second retainer ring 56 will secure the distal end of the expandable membrane 18. In one aspect, the retainer rings may be laser-welded to further secure the ring about the expandable membrane 18. As illustrated in FIGS. 5 to 10 for exemplary purposes, the expandable membrane 18 may be adhesively affixed and/or engaged by laser welding of a retainer ring, to or into the proximal body 12 and the distal body 16. The expandable membrane 18 may be secured with an adhesive. One suitable adhesive is a silicone adhesive.

The expandable membrane 18 may be expanded by injection of a prosthetic nucleus material 60. In one aspect, the injection of prosthetic nucleus material 60 may be under high pressure. Typically, the prosthetic nucleus material 60 is injected into the expandable membrane 18 with a syringe. In this manner, the expandable membrane 18 may inflate and extend into the intervertebral disc space 860 until it conformably contacts the surfaces within the intervertebral disc space 860. The ultimate expansion of the expandable membrane 18 can be limited by contact with and movement of the end plates of the adjacent vertebral bodies and the annulus. Prosthetic nucleus materials 60 may include saline, viscoelastic gels, elastomeric solids, or blends or combinations thereof.

In a preferred aspect, prosthetic nucleus material 60 can be a hydrogel, which can be introduced into the expansion chamber 20 of the expandable membrane 18 in a liquid or dry particulate form or in microspheres or beads. Further, regardless of the material, the prosthetic nucleus material preferably has a Shore D range from between A10 to D90. For example, one hydrogel is formulated as a mixture of hydrogel polyacrylonitrile or any hydrophilic acrylate derivative with a unique multiblock copolymer structure or any other hydrogel material having the ability to imbibe and expel fluids while maintaining its structure under various stresses. As an example, the hydrogel can be formulated as a mixture of polyvinyl alcohol and water. The hydrogel core formed within the expandable membrane 18 will swell as it absorbs fluids through the porous fabric wall of the expandable membrane 18, preferably in the manner of a native nucleus. When fully hydrated, the hydrogel core may have a water content of between 25-95%. The hydrogel material of one suitable embodiment is manufactured under the trade name Hypang by Hymedix International, Inc., and has a water content of about 80-95%. Another hydrogel system comprises natural hyaluronan gels or blends that may be chemically altered to enhance structure, e.g., scaffolding ability or physical state, and optimize biomechanical properties in situ via laser exposure, e.g., to convert liquid into a solid. Yet other hydrogels (such as, PEG; PEO; PVP) or blends of hydrogels (such as, PVA/PVP; PEG-based/PE glycated hydrogels; crosslinked aliphatic polyoxaamide polymers; or combinations of synthetic and native polypeptides or GAGs, such as actin, fibrinogen, collagen and elastin; chondroitin, keratin and dermatan sulfate; chitosan) and/or elastomers or other combinations (e.g., incorporation of an ionic or hydrophobic monomer into the hydrogel network, to engineer a reversibly responsive polymer) that optimize desired intramolecular and intermolecular bonding arrangements and reproduce the viscoelastic properties of the native nucleus, may also be used. Conceptually, this is enabled from understanding fundamental relationships between the structure of the polymer (e.g., molecular weight; cross-linking density, etc.) under physiological conditions and the physical properties of the resulting hydrogels. As noted previously, the native nucleus consists of mostly type II collagen (cartilage like) and large protein macromolecules called proteoglycans that absorb water into the disc and are extremely important to the biomechanical properties of the disc. Hydrogels modify their molecular arrangement, volume and/or phase when acted upon by a specific stimulus such as temperature, light, a pH change or other chemical inducement, osmotic pressure or mechanical stress, or electric field, and selection of the prosthetic nucleus material of the present invention is not limited in scope with respect to materials' trigger stimuli, and may include those that are either chemically and/or physically cross-linked gels (e.g., via ion-complexation or those that are thermoreversibly cross-linked) as suitable. Hence in a preferred embodiment, the prosthetic nucleus material is selected based on its stability under physiological conditions and/or in physiological fluids, including the ability withstand load, resist shear stresses and fatigue forces, or other factors that might otherwise induce fragmentation or otherwise promote extrusion or migration, or fractional mass loss over time.

In other aspects, the expandable membrane 18 may be configured to contain prosthetic nucleus material 60 comprising hydrogels that are implanted or inserted in a dehydrated condition, for example by means of a glycerin carrier. The hydrogels are typically 3-dimensional structures consisting mainly of hydrophilic (i.e., very high affinity for water) polymeric materials or copolymers which retain water, without dissolving, within a network stability that is achieved through the presence of chemical or physical crosslinks (e.g., entanglements; crystallites; primary covalent or secondary hydrogen, ionic, or Van der Waals bonds). In this manner, the overall bulk of the mobility preservation apparatus 10 may be reduced, allowing the hydrogel to be inserted through a smaller access and the subsequent hydration, which results in an increase in volume of the hydrogel, may assist in disc distraction to at least partially restore disc height. In certain embodiments, the prosthetic nucleus material 60 may remain fluid. In other embodiments, mobility preservation apparatus 10 may be configured for deployment via minimal access, by introducing the hydrogel or polymeric material in a first state or condition (e.g., flowable), and to then allow or induce conversion of the material to a second phase or state, (e.g., to a solid). In this manner, the prosthetic nucleus material 60 can be introduced through the smallest possible access and yet still be provided in sufficient quantity to fill the disc space 860 and provide the desired function. Examples of methods to convert a material from a first flowable state to a second solid state include but are not limited to: a temperature phase change as from a melted state to a frozen state, polymerization of a monomer or low molecular weight polymer such as with the use of a catalyst; laser or UV cross-linking of a liquid polymer resulting in a solid, leaching of a solvent by replacing it with water (for example: polyacrylonitrile-polyacrylamide hydrogel can be dissolved in dimethylsufloxide (DMSO) resulting in a flowable liquid which will instantly transform to a solid in the presence of water, into which the DMSO will preferentially flow), use of reverse gelation polymers, such as Pluronic™, commercially available from BASF, Inc., Mount Olive, N.J. (USA), that are liquid at room temperature and form a solid at elevated temperatures such as body temperature, etc.

As noted earlier, mobility preservation apparatus 10 are typically implanted following complete or partial nucleectomy to remove all or a portion of the nucleus pulposus, respectively, to create a disc space 860 within the intervertebral disc. However, generally the bore 850 through which a prosthetic nucleus apparatus 10 is axially implanted will typically be smaller than the volume of the intervertebral disc space 860 to be augmented or replaced. To compensate for the spatial discrepancy, in one variation, an expandable membrane 18 is inserted in a folded, relaxed, or unfilled state into the prepared disc space 860 and prosthetic nucleus material 60 is injected or infused into the membrane in situ. In situ, the prosthetic nucleus materials 60 are typically delivered through an elongated delivery tube or catheter connected to the syringe. An elongated delivery tube may seat against the proximal end of the proximal body 12 to transfer the prosthetic nucleus material into the proximal lumen 42 of the proximal body 12. In one aspect, the two components may be seated by rotatably engaging one another such as for example by including a Leur Lock type configuration. Alternatively, the elongated delivery tube may be configured to be received within a lumen (e.g. proximal lumen 42, intermediate lumen 44 andlor distal lumen 46) as illustrated in FIGS. 22 to 26. Depending upon the particular embodiment, the prosthetic nucleus material 60 may be communicated into the expansion chamber 20 defined by the expandable membrane 18 directly from the proximal lumen 42, through fenestrations 74 in communication with proximal lumen 42 and/or intermediate lumen 44, or in other ways communicated to the expandable membrane 18 as will be recognized by those skilled in the art upon review of the present disclosure. The distal end of the elongated delivery tube may be inserted through a cannula into the proximal body 12 as illustrated in FIGS. 22 to 26. As the prosthetic nucleus material 60 is provided through the proximal lumen 42 or fenestrations 74 the material engages the inner surface of expandable membrane 18 and, with sufficient internal pressure, causes the expandable membrane 18 to expand by filling the expansion chamber 20.

Figure 2:
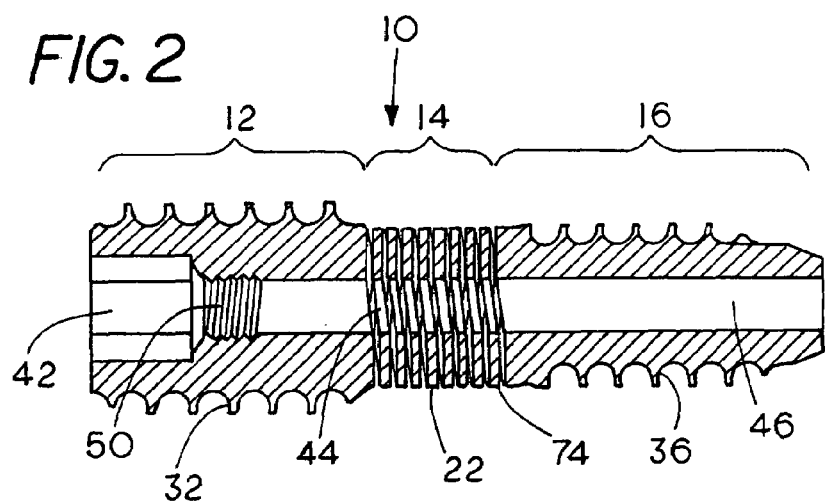
FIG. 2 illustrates a cross-section of a side view of an embodiment of a mobility preservation apparatus without an expandable membrane having a unitary elongated body and a lumen extending over the entire length of the elongated body.
Figure 3:
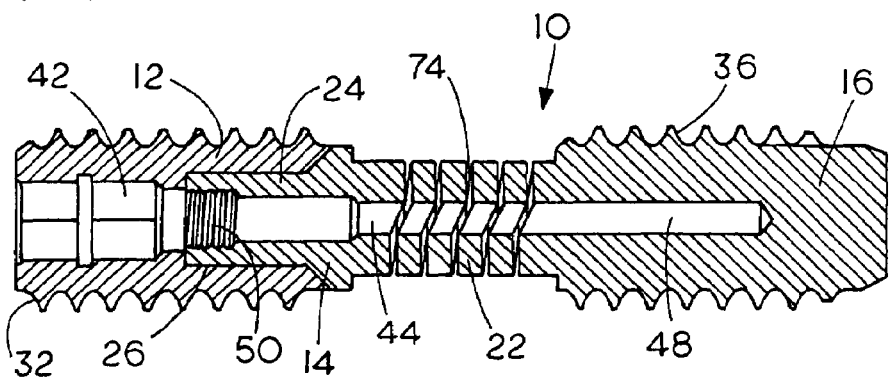
FIG. 3 illustrates a cross-section of a side view of an embodiment of a mobility preservation apparatus without an expandable membrane having a male portion and a female portion and a cavity which terminates prior to the distal end of the distal body.

FIGS. 1 to 4 illustrate an exemplary mobility preservation apparatus 10. The mobility preservation apparatus 10 includes the proximal body 12, intermediate body 14, and distal body 16. The mobility preservation apparatus 10 will typically have an aspect ratio of greater than 1. The mobility preservation apparatus 10 may be formed from a single piece of material, as illustrated in FIGS. 1 and 2, or may be formed by multiple components coupled together as illustrated in FIG. 3. When formed as multiple components, the proximal component and the distal component may be secured to one another to form the mobility preservation apparatus 10.

In the multiple component configurations, one component may include a male portion 24 while the corresponding component will include female portion 26. The male portion 24 is then received in the female portion 26 to couple the two components together. As illustrated in FIG. 3, the intermediate body 14 and the distal body 16 are machined from a single piece of material and include a male portion 24. The proximal body 14 is itself illustrated as machined from a single piece of material and includes a female portion 26. The female portion 26 is generally configured to receive in the male portion 24. In one aspect, the female portion 26 may be sized and/or shaped to rotatably receive the male portion 24. For example, both the male portion 24 and the female portion 26 could have a circular shape about their longitudinal axis to permit rotating when coupled or the female portion 26 could have a circular shape about its longitudinal axis and the male portion 24 could have a hexagonal shape about its longitudinal axis but could be sized to be received within the female portion 26. In this manner, the proximal component and the distal component may be rotated independently of one another which has advantages for spacing and distraction purposes as will be recognized by those skilled in the art. In another aspect, the female portion 26 may be sized and/or shaped to interlockingly receive the male portion 24. For example, both the male portion 24 and the female portion 26 could have a hexagonal shape about their longitudinal axis with corresponding sizes to permit the male portion 24 to be interlocking received within the female portion 26 when the two components are coupled. In this manner, the proximal component and the distal component may be synchronously rotated and, yet, could remain independently implantable.

In operation, embodiments of the multi-component configurations of elongated body 12 may, for example, allow more effective use of the S1 vertebra to drive and lift the L5 segment in a controlled manner and independent of patient anatomy or the location of first thread engagement on/into the L5 vertebral body. Further, the modularity of the multi-component configurations of elongated body 12 may facilitate retention of progression-in-treatment options. For example, a plug inserted into the proximal end of a cannulated female inferior anchor portion, which plug extends sufficiently through and distally into the fenestrated intermediate body 14 of the mobility preservation apparatus to effectively reduce the flexibility of the device. In the extreme, such a plug could effectively convert the spinal mobility apparatus 10 into an immobilization or fusion device.

Figure 15:
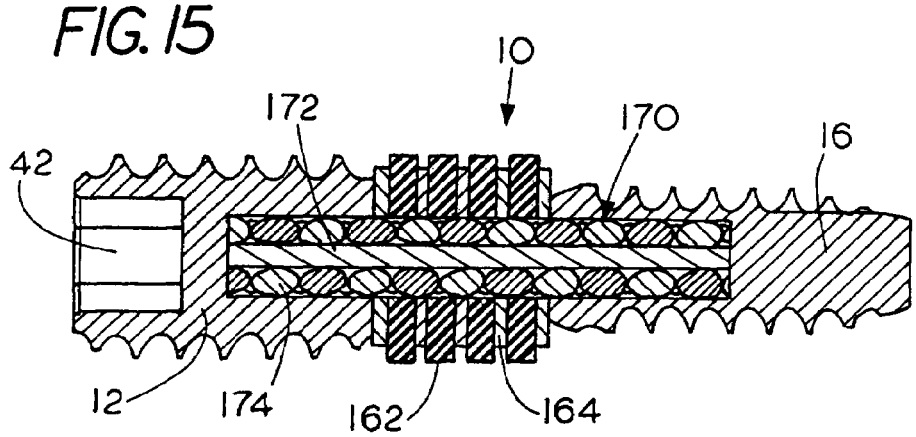
FIG. 15 illustrates a cross-section of a side view of an embodiment of a mobility preservation apparatus with a stacked washer design for the flexible element.
Figure 16:
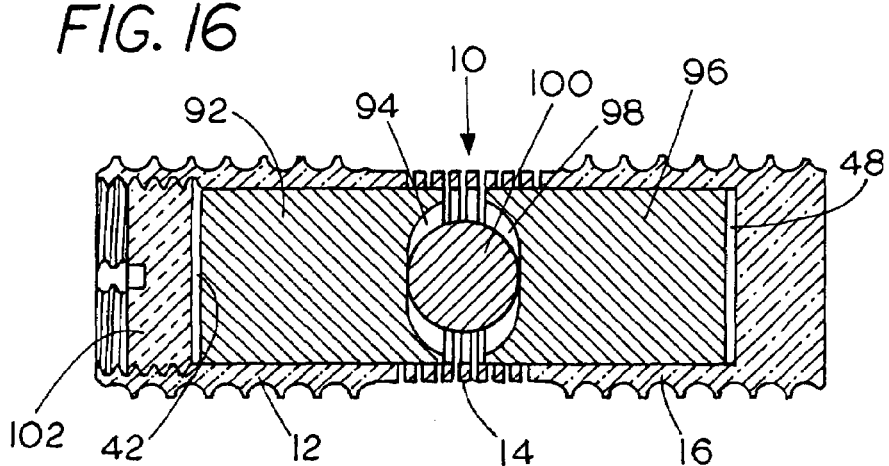
FIG. 16a illustrates a cross-section of a side view of an embodiment of a mobility preservation apparatus with a ball and track configuration for the flexible element.
FIG. 16b illustrates a perspective view of an embodiment of a proximal insert from a mobility preservation apparatus with a ball and track configuration.

The proximal body 12 of FIGS. 1 to 3 includes a set of first threads 32 to secure proximal body 12 to the body of a caudal vertebra 800. The first threads 32 are illustrated for exemplary purposes as extending over substantially the entire length of proximal body 12. The first threads 32 may include a chamfer to ease insertion and removal of the mobility preservation apparatus 10 from various tools involved with its implantation. The proximal body 12 may define a proximal lumen 42, as illustrated in FIGS. 1 and 2. The proximal lumen 42 of the proximal body 12 may be configured to receive a driver 400, such as for example a hex-head driver, to confer a rotational force to insert, remove or position a mobility preservation apparatus 10 within or between vertebral bodies. Alternatively, proximal lumen 42 may be configured to allow the passage of a driver 400 to be received by the intermediate lumen 44 of intermediate body 14 and/or the distal lumen 46 of distal body 16. In addition, proximal lumen 42 of the proximal body 12 may include internal threads 50 to secure a plug 80 and/or a flexure rod 60, as illustrated in FIGS. 11, 15 and 16 and discussed below.

The intermediate body 14 of FIGS. 1, 2, and 4 is secured to proximal body 12. The intermediate body 14 is illustrated as a helical flexure for exemplary purposes. The helical flexure is illustrated as extending over substantially the entire length of intermediate body 14. However, those skilled in the art will recognize that the helical flexure or other flexible element 22 of intermediate body 14 may extend over the entire length or a fraction of the length of intermediate body 14. The intermediate body 14 may also define an intermediate lumen 44. The intermediate lumen 44 may be coaxial and in communication with the proximal lumen 42 of proximal body 12. Intermediate lumen 44, as illustrated in FIGS. 2 and 4, may be configured to receive a driver 400, such as for example a hex-head driver, to confer a rotational force to insert, remove or position a mobility preservation apparatus 10 within or between vertebral bodies. Alternatively, intermediate lumen 44 may be configured to allow the passage of a driver 400 to be received by the distal body 16. In addition, intermediate lumen 44 may include internal threads 50 to secure a plug 80 and/or a flexure rod 60, as illustrated in FIGS. 11, 15 and 16 and discussed below. One or more fenestrations 74 may extend between an outer surface of intermediate body 14 and the intermediate lumen 44. Fenestrations 74 in FIGS. 1 to 3 are illustrated as the space defined between the windings of helical flexure for exemplary purposes. Upon review of the present disclosure, those skilled in the art will recognize that fenestrations 74 may take a wide variety of forms.

The distal body 16 of FIGS. 1 to 4 includes a set of second threads 36 to secure distal body 16 to the body of a cephalad vertebra 900. For exemplary purposes, the second threads 36 are illustrated as extending over substantially the entire length of distal body 16. In one embodiment, the second threads 36 may have an outside diameter that is less than or equal to the inside diameter of the proximal threads. Thus, the second threads 36 may be sized to slidably pass through a bore through which the caudad thread must be rotatably driven. Further, the second threads 36 may include a chamfer to ease insertion and removal of the mobility preservation apparatus 10 from various tools involved with its implantation as well as to assist in placement of the mobility preservation apparatus within a patient. The pitch of the second threads 36 may be less than the pitch of the first threads 32 to provide a degree of distraction as the mobility preservation apparatus 10 is secured into adjacent vertebrae. In one embodiment, the distal body 16 may include second threads 36 having a 12-pitch and the proximal body 12 may include first threads 32 having a 10-pitch. Further, the distal body 16 may be configured as a self-tapping bone screw by, for example, including a chip breaker at the distal end of the distal body 16. As illustrated in FIGS. 2 and 4, the distal body 16 may also define a distal lumen 46. The distal lumen 46 of the distal body 16 may be configured to receive a driver 400 to confer a rotational force to insert, remove or position a mobility preservation apparatus 10 within or between vertebral bodies. In addition, distal lumen 46 may include internal threads 50 to secure a plug 80, as illustrated in FIGS. 11, 15 and 16 and discussed below. Alternatively, the distal body 16 may define a distal cavity 48, having a closed end as illustrated in FIG. 3. The distal cavity 48 may be configured to receive a driver 400 to confer a rotational force to insert, remove or position a mobility preservation apparatus 10, as a whole, or the distal body 16 independently within or between vertebral bodies. Distal cavity 48 may also prevent the migration of infused materials substantially beyond the intermediate body 14, such as in procedures designed to add a prosthetic nucleus onto mobility preservation apparatus 10. In addition, distal cavity 48 of the distal body 16 may include internal threads 50 to secure a plug 80 and/or a stiffening member 82, as illustrated in FIGS. 11, 15 and 16 and discussed below.

FIGS. 5 to 8 illustrate another exemplary mobility preservation apparatus 10. As illustrated, mobility preservation apparatus 10 includes a proximal body 12, an intermediate body 14, a distal body 16 and an expandable membrane 18.

Figure 8:
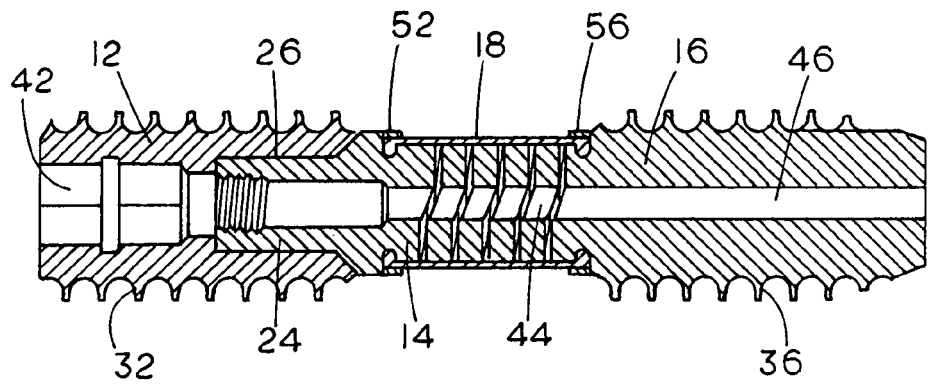
FIG. 8 illustrates a cross-section of a side view of an embodiment of a mobility preservation apparatus having a multi-piece configuration with a male portion and a female portion with an expandable membrane in an unexpanded position.

The mobility preservation apparatus 10 will typically have an aspect ratio of greater than 1. The expandable membrane 18 is secured about the intermediate body 14. The proximal body 12, intermediate body 14, distal body 16 may be formed from a single piece of material, as illustrated in FIGS. 5 to 7, or may be formed by multiple components coupled together, as illustrated in FIG. 8. As illustrated, the proximal component and the distal component may include a male portion 24 and the corresponding component will include female portion 26 to couple the proximal component and the distal component.

In a multiple component embodiment, the female portion 26 is generally configured to receive in the male portion 24. In one aspect, the female portion 26 may be sized and/or shaped to rotatably receive the male portion 24. For example, both the male portion 24 and the female portion 26 could have a circular shape about their longitudinal axis to permit rotating when coupled or the female portion could have a circular shape about its longitudinal axis and the male portion 24 could have a hexagonal shape about its longitudinal axis but could be sized to be received within the female portion 26. In this manner, the proximal component and the distal component may be rotated independently of one another which has advantages for spacing and distraction purposes as will be recognized by those skilled in the art. In another aspect, the female portion 26 may be sized and/or shaped to interlockingly receive the male portion 24. For example, both the male portion 24 and the female portion 26 could have a hexagonal shape about their longitudinal axis with corresponding sizes to permit the male portion 24 to be interlocking received within the female portion 26 when the two components are coupled. In this manner, the proximal component and the distal component may be synchronously rotated and, yet, could remain independently implantable.

In operation, embodiments of the multi-component configurations of mobility preservation apparatus 10 may, for example, allow more effective use of the S1 vertebra to drive and lift the L5 segment in a controlled manner and independent of patient anatomy or the location of first thread engagement on/into the L5 vertebral body. Further, the modularity of the multi-component configurations of elongated body 12 may facilitate retention of progression-in-treatment options. For example, a plug 80 may be inserted into proximal lumen 42 at the proximal end of the proximal body 12 and may extend distally a sufficiently distance through the intermediate lumen 44 of the intermediate section 14 to compromise the flexibility of flexible element 22. If the plug 80 sufficiently compromises the flexibility of the flexible element, mobility preservation apparatus 10 may effectively serves as an immobilization or fusion device.

The proximal body 12 of FIGS. 5 to 8 includes a set of first threads 32 to secure proximal body 12 to the body of a caudal vertebra 800. The first threads 32 are illustrated for exemplary purposes as extending over substantially the entire length of proximal body 12. The first threads 32 may include a chamfer to ease insertion and removal of the mobility preservation apparatus 10 from various tools involved with its implantation. The proximal body 12 may define a proximal lumen 42. The proximal lumen 42, as illustrated in FIG. 6 to 8, may be configured to receive a driver 400, such as for example a hex-head driver, to confer a rotational force to insert, remove or position a mobility preservation apparatus 10 within or between vertebral bodies. Alternatively, proximal lumen 42 may be configured to allow the passage of a driver 400 to be received by the intermediate body 14 and/or distal body 16. In addition, proximal lumen 42 of may include internal threads 50 to secure a plug 80, as illustrated in FIGS. 3 and 4 and discussed below.

The intermediate body 14 of FIGS. 5 to 8 is secured to proximal body 12. The intermediate body 14 is illustrated as a helical flexure for exemplary purposes. The helical flexure is illustrated as extending over substantially the entire length of intermediate body 14. However, those skilled in the art will recognize that the helical flexure or other flexible element 22 of intermediate body 14 may extend over the entire length or a fraction of the length of intermediate body 14. The intermediate body 14 may also define an intermediate lumen 44. The intermediate lumen 44 may be coaxial and in communication with the proximal lumen 42. The intermediate lumen 44, as illustrated in FIGS. 6 to 8, may be configured to receive a driver 400, such as for example a hex-head driver, to confer a rotational force to insert, remove or position a mobility preservation apparatus 10 within or between vertebral bodies. Alternatively, intermediate lumen 44 may be configured to allow the passage of a driver 400 to be received by the distal body 16. In addition, the intermediate lumen 44 may include internal threads 50 to secure a plug 80, as illustrated in FIGS. 11, 15 and 16 and discussed below. One or more fenestrations 74 may extend between an outer surface of intermediate body 14 and the intermediate lumen 44. Fenestrations 74 in FIGS. 6 to 8 are illustrated as the space defined between the windings of helical flexure for exemplary purposes. Upon review of the present disclosure, those skilled in the art will recognize that fenestrations 74 may take a wide variety of forms.

The distal body 16 of FIGS. 5 to 8 includes a set of second threads 36 to secure distal body 16 to the body of a cephalad vertebra 900. For exemplary purposes, the second threads 36 are illustrated as extending over substantially the entire length of distal body 16. In one embodiment, the second threads 36 may have an outside diameter that is less than or equal to the inside diameter of the proximal threads. Thus, the second threads 36 may be sized to slidably pass through a bore through which the caudad thread must be rotatably driven. Further, the second threads 36 may include a chamfer to ease insertion and removal of the mobility preservation apparatus 10 from various tools involved with its implantation as well as to assist in placement of the mobility preservation apparatus within a patient. The pitch of the second threads 36 may be less than the pitch of the first threads 32 to provide a degree of distraction as the mobility preservation apparatus 10 is secured into adjacent vertebrae. In one embodiment, the distal body 16 may include second threads 36 having a 12-pitch and the proximal body 12 may include first threads 32 having a 10-pitch. Further, the distal body 16 may be configured as a self-tapping bone screw by, for example, including a chip breaker at the distal end of the distal body 16. As illustrated in FIG. 8, the distal body 16 may also define a distal lumen 46. The distal lumen 46 may be configured to receive a driver 400 to confer a rotational force to insert, remove or position a mobility preservation apparatus 10 within or between vertebral bodies. In addition, distal lumen 46 may include internal threads 50 to secure a plug 80, as illustrated in FIGS. 11, 15 and 16 and discussed below. Alternatively, the distal body 16 may define a distal cavity 48, having a closed end as illustrated in FIGS. 6 and 7. The distal cavity 48 may be configured to receive a driver 400 to confer a rotational force to insert, remove or position a mobility preservation apparatus 10, as a whole, or the distal body 16 independently within or between vertebral bodies. Distal cavity 48 may also function to prevent the migration of infused materials substantially beyond the intermediate body 14, such as in procedures designed to add a prosthetic nucleus onto mobility preservation apparatus 10. In addition, distal cavity 48 of the distal body 16 may include internal threads 50 to secure a plug 80 (not shown).

An embodiment of an expandable membrane 18 is illustrated in FIGS. 5 to 8 for use in conjunction with the present embodiment having a proximal body 12, an intermediate body 14 and a distal body 16. As illustrated, expandable membrane 18 is secured over the length of intermediate body 14. As illustrated in FIGS. 5 to 8, the expandable membrane 18 is secured at locations both proximal and distal to fenestrations 74. Accordingly, prosthetic nucleus material 60 passing through fenestrations 74 may forcibly expand the expandable membrane 18. For exemplary purposes, the expandable membrane 18 is illustrated as being secured about the intermediate body 14 by a proximal retaining ring 22 and a distal retaining ring 24. The proximal retaining ring 22 and the distal retaining ring 24 are secured over the expandable membrane 18. In one aspect, the proximal retaining ring 52 and the distal retaining ring 54 may be laser welded to secure them in position. Alternatively, the proximal retaining ring 52 and the distal retaining ring 54 may be sized and configured to compressionally secure portions of the expandable membrane 18 about the intermediate body 14. FIGS. 6 and 8 illustrate the expandable membrane 18 in an unexpanded position. Further, for exemplary purposes, the unexpanded position is illustrated with the expandable membrane positioned flush with the intermediate body 14. FIGS. 5 and 6 illustrate the expandable membrane in an at least partially expanded position.

Figure 9:
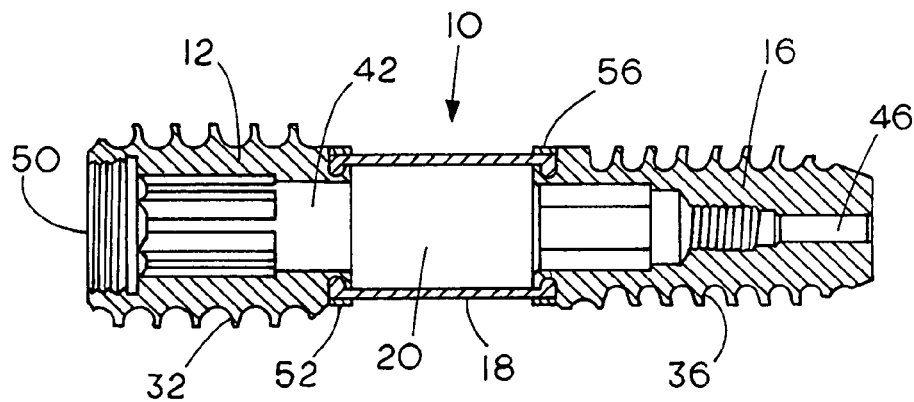
FIG. 9 illustrates a cross-section of a side view of an embodiment of a mobility preservation apparatus having an expandable membrane connecting the proximal body and the distal body in an unexpanded position.
Figure 10:
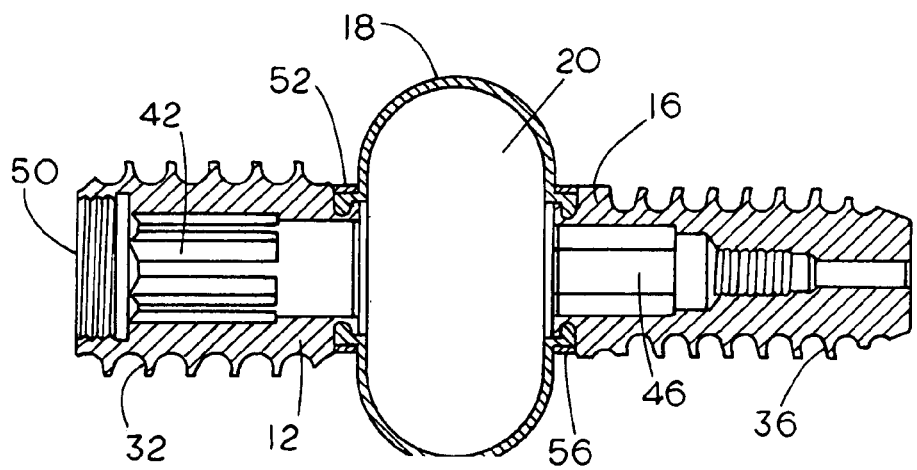
FIG. 10 illustrates a cross-section of a side view of an embodiment of a mobility preservation apparatus having an expandable membrane connecting the proximal body and the distal body in an expanded position and a central lumen which terminates prior to the distal end of the distal body.

FIGS. 9 and 10 illustrate yet another embodiment of a mobility preservation apparatus 10. The mobility preservation apparatus 10 of FIGS. 9 and 10 includes a proximal body 12, a distal body 16 and an expandable membrane 18. FIG. 9 illustrates the expandable membrane 18 in an unexpanded position. FIG. 10 illustrates the expandable membrane 18 in an at least partially expanded position. As illustrated, the proximal body 12 and the distal body 16 are connected by a tubular expandable membrane 18 to form a mobility preservation apparatus 10. The expandable membrane 18 is secured at a proximal end to proximal body 12 and at a distal end to distal body 16.

The proximal body 12 of FIGS. 9 and 10 includes a set of first threads 32 to secure proximal body 12 to the body of a caudal vertebra 800. The first threads 32 are illustrated for exemplary purposes as extending over substantially the entire length of proximal body 12. The first threads 32 may include a chamfer to ease insertion and removal of the mobility preservation apparatus 10 from various tools involved with its implantation. The proximal body 12 may define a proximal lumen 42. The proximal lumen 42, as illustrated in FIGS. 9 and 10, may be configured to receive a driver 400, such as for example a hex-head driver, to confer a rotational force to insert, remove or position a mobility preservation apparatus 10 within or between vertebral bodies. Alternatively, proximal lumen 42 may be configured to allow the passage of a driver 400 to be received by the intermediate body 14 and/or distal body 16. In addition, proximal lumen 42 of may include internal threads 50 to secure a plug 80, as illustrated in FIGS. 3 and 4 and discussed below.

The distal body 16 of FIGS. 9 and 10 includes a set of second threads 36 to secure distal body 16 to the body of a cephalad vertebra 900. For exemplary purposes, the second threads 36 are illustrated as extending over substantially the entire length of distal body 16. In one embodiment, the second threads 36 may have an outside diameter that is less than or equal to the inside diameter of the proximal threads. Thus, the second threads 36 may be sized to slidably pass through a bore through which the caudad thread must be rotatably driven. Further, the second threads 36 may include a chamfer to ease insertion and removal of the mobility preservation apparatus 10 from various tools involved with its implantation as well as to assist in placement of the mobility preservation apparatus within a patient. The pitch of the second threads 36 may be less than the pitch of the first threads 32 to provide a degree of distraction as the mobility preservation apparatus 10 is secured into adjacent vertebrae. In one embodiment, the distal body 16 may include second threads 36 having a 12-pitch and the proximal body 12 may include first threads 32 having a 10-pitch. Further, the distal body 16 may be configured as a self-tapping bone screw by, for example, including a chip breaker at the distal end of the distal body 16. As illustrated in FIG. 8, the distal body 16 may also define a distal lumen 46. The distal lumen 46 may be configured to receive a driver 400 to confer a rotational force to insert, remove or position a mobility preservation apparatus 10 within or between vertebral bodies. In addition, distal lumen 46 may include internal threads 50 to secure a plug 80, as illustrated in FIGS. 11, 15 and 16 and discussed below. Alternatively, the distal body 16 may define a distal cavity 48, having a closed end as illustrated in FIGS. 6 and 7. The distal cavity 48 may be configured to receive a driver 400 to confer a rotational force to insert, remove or position a mobility preservation apparatus 10, as a whole, or the distal body 16 independently within or between vertebral bodies. Distal cavity 48 may also function to prevent the migration of infused materials substantially beyond the distal body 16, such as in procedures designed to add a prosthetic nucleus onto mobility preservation apparatus 10. In addition, distal cavity 48 of the distal body 16 may include internal threads 50 to secure a plug 80 (not shown).

As illustrated, expandable membrane 18 is secured between the proximal body 12 and the distal body 16. The expandable membrane 18 may be secured circumferentially about the adjacent components, within a lumen or cavity associated with the component or may otherwise be secured as will be recognized by those skilled in the art. The expandable membrane 18 may include a proximal lip 62 and a distal lip 66 to engage the proximal body 12 and the distal body 16, respectively. The proximal body 12 may include a proximal groove 64 to receive the proximal lip 62 of the expandable membrane 18. Typically, the proximal groove 64 will extend circumferentially around the proximal body 12 to sealing engage expandable membrane 18. Similarly, the distal body 16 may include a distal groove 68 to receive the distal lip 66 of the expandable membrane 18. Typically, the distal groove 68 will extend circumferentially around the distal body 16 to sealing engage expandable membrane 18. The expandable membrane 18 may be further secured about the intermediate body 14 by a proximal retaining ring 22 and a distal retaining ring 24. The proximal retaining ring 22 and the distal retaining ring 24 are secured over the expandable membrane 18. In one aspect, the proximal retaining ring 52 and the distal retaining ring 54 may be laser welded to secure them in position. Alternatively, the proximal retaining ring 52 and the distal retaining ring 54 may be sized and configured to compressionally secure portions of the expandable membrane 18 about the intermediate body 14. In addition or alternatively, an adhesive may be provided to bind the expandable membrane 10 to the proximal body 12 and the distal body 16. Regardless of how the expandable membrane 18 is secured, the expandable membrane 18 is sufficiently secure to permit prosthetic nucleus material 60 passing through proximal lumen 42 may forcibly expand the expandable membrane 18 without dislodging the expandable membrane 18.

An embodiment of an expandable membrane 18 is illustrated in FIGS. 9 and 10 for use in conjunction with the present embodiment having a proximal body 12 and a distal body 16. The expandable membrane will typically lack sufficient torsional rigidity to permit the implantation of mobility preservation apparatus using a driver 400 which engages only the proximal body 12. Accordingly, a driver 400 will typically be provided to simultaneously engage both the proximal body 12 and the distal body 16 to synchronously rotate the proximal body 12 and distal body 16 during implantation. This may be accomplished by having two heads on driver 400 the more distal head sized to pass through proximal lumen 42 and to engage distal lumen 46 and the more proximal head being sized to engage proximal lumen 42. In one aspect, driver 400 may be configured to engage the mobility preservation apparatus 10 to prevent the dislodgement of the heads during implantation.

In one exemplary methodology, the mobility preservation apparatus 10 illustrated in FIGS. 1 to 10 may be implanted trans-sacrally. Where after paracoccygeal entry, a mobility preservation apparatus 10 may be deployed into the L5-S1 spinal motion segment via the trans-sacral axial techniques and instrumentation disclosed in co-pending and commonly assigned U.S. patent application entitled "Access Assembly for Guiding Instrumentation Through Soft Tissue to a Point on the Spine", attorney docket number AXIAMD.015A, filed concurrently herewith on Oct. 22, 2004, the contents of which are hereby incorporated in entirety into this disclosure by reference.

More specifically, in a preferred procedure the blunt-tipped stylet is introduced percutaneously through the guide pin introducer and safely enables advancement of the guide pin introducer through the soft tissue of the pre-sacral track up to the anterior target site on sacral face. The stylet is withdrawn from the guide pin introducer now positioned in place at the target site, and a beveled guide pin of about 0.125" O.D. is inserted, with its handle attached by engagement means of a hex and thumb screw lock, into the guide pin introducer, forming a guide pin-guide pin introducer assembly. Under fluoroscopic guidance to appropriately maintain anterior/posterior alignment, the beveled tip at the distal end of the guide pin is advanced into the sacrum from the target site on the sacral face by means of tapping the proximal end with a hammer or mallet. The guide pin is driven through the sacrum; the L5-S1 disc space, and anchored into L5 prior to bone dilation. The thumb screw is loosened and the guide pin handle is removed from the guide pin's proximal end, to enable attachment of the guide pin extension. The guide pin introducer is then removed without disturbing the guide pin.

Next, a cannulated 6 mm dilator is inserted over the guide pin extension and its distal end is advanced, by means of tapping with a slap hammer, also inserted over the guide wire, against the handle at the proximal end of the dilator, up to (or in close proximity, e.g., within about 6-10 mm) the vertebral end plate. The 6 mm dilator is then withdrawn over the guide pin, and the same process is sequentially repeated using first a cannulated 8 mm dilator, and then a cannulated 10 mm dilator as part of an assembly in engagement with a tapered (approximately 0.375" OD) dilator sheath, respectively inserted over the guide pin and advanced into the sacrum. The dilator handle is then disengaged from the sheath and the dilator is withdrawn over the guide pin, leaving the dilator sheath in place, to preserve trajectory. The guide pin is then removed to enable insertion of a (non-cannulated) 9 mm twist drill through the dilator sheath, which is used to drill, through the large dilator sheath, through S1 into the L5-S1 intervertebral disc, through the inferior endplate of L5 and to axially advance into L5. For L5-S1 procedures, i.e., where multi-level implants or therapies are not prescribed, the axial access track is not drilled through L5 into the L4-L5 intervertebral disc, and stops often about 10 mm caudally from the superior vertebral endplate of L5, and the length of the axial track accommodates the distal anchor of the particular mobility preservation apparatus 10 to be implanted.

Then, following removal of the 9 mm drill, the 10 mm dilator tapered large dilator sheath is further advanced, if necessary, through which nucleectomy is performed, by using 3-4 cutters with a plurality of (preferably teardrop shaped) blade configurations, e.g., lengths, and about 6 tissue extraction tools to create an intervertebral disc space 860. After removal of the nucleus pulposus (typically taking care not to scrape cartilage from the vertebral endplates so as to cause bleeding that would enhance undesired fusion) and withdrawal of tissue cutter and extraction tools, typically, an approximately 23" long guide pin of about 0.09" diameter is inserted through the dilator sheath, and the exchange bushing is inserted over the pin, over the dilator sheath and advanced to the target site on the sacral face. Then, the exchange cannula is inserted over the exchange bushing, and left in place following subsequent removal of the bushing. The 10 mm dilator is then inserted into the dilator sheath, to engage and remove it.

At this point in the procedure is generally illustrated in FIGS. 22 to 26, mobility preservation apparatus 10 are delivered generally via torque driver inserter tools such as driver 400 appropriately configured with male components to engage (e.g., via hex head) female sockets of the mobility preservation apparatus 10 (or a female component on a driver 400 engaging a male component on a mobility preservation apparatus 10) within a cannula, over the guide wire and deployed through the exchange system and into or through the intervertebral disc space 860. The guide pin is removed and disc spaces are augmented with prosthetic nucleus material 60, e.g., by injection through a suitable insertion media injector either into/within an expandable membrane 18 of an accompanying mobility preservation apparatus 10, or via deployment directly into the intervertebral disc space 860, e.g., by engaging the distal end of the inserter with the proximal end of the mobility preservation apparatus 10 and injecting the augmentation media therein, e.g., delivery into a membrane 18, or through fenestrations 74, or directly into the intervertebral disc space 860. Deployment of prosthetic nucleus material 60 directly into the intervertebral disc space 860 may be performed by various means and techniques, e.g., an exemplary multi-step procedure wherein a barrier sealant membrane is introduced to seal (e.g., annular) fissures followed by subsequent introduction of bulk prosthetic nucleus material 60, such as disclosed in co-pending and commonly assigned U.S. Provisional Patent Application having Ser. No. number 60/599,989 filed Aug. 9, 2004 the contents of which are hereby incorporated in entirety into this disclosure by reference.

For example, in deploying a mobility preservation apparatus 10, the distal end of the mobility preservation apparatus 10 is deployed over the proximal end of the extended guide pin and delivered into and through the exchange cannula. More specifically, the proximal end of the proximal body 12 is engaged to a torque (e.g., rotatable) rod driver tool, and the preloaded mobility preservation apparatus 10 is inserted over the guide pin to axially advance, by means of rotation, the implant through S1, through the L5-S1 disc intervertebral disc space 860 and into L5. When mobility preservation apparatus 10 are configured to comprise a proximal body 12 having first threads 32 and a distal body 16 having second threads 36 where the respective threads may be configured with differential pitches, such rotation distracts the L5 and S1 vertebral bodies, as the device is driven into L5.

After mobility preservation apparatus 10 deployment in vivo and insertion of the prosthetic nucleus material 60 by means of an appropriate augmentation media inserter, the extended guide pin is reinserted and stop-flow means 80, e.g., typically a cannulated, female-threaded axial rod plug 80, is next inserted, as follows: the proximal end of the plug 80 is fitted on the distal end of the rod driver that is configured (e.g., male hex head) to engage the plug 80, and which is then inserted and axially advanced into the proximal end of the proximal body of the deployed mobility preservation apparatus 10. Next, the plug driver is removed. Once the plug driver has been removed from the access track, site closure is performed by the surgeon.

In one aspect of the invention, when a threaded mobility preservation apparatus 10 having a proximal body 12 and a distal body 16 with no intermediate body 14 and which may include an expandable membrane 18, are deployed, the mobility preservation apparatus 10 implants are deployed by means of a driver 400 that is configured as a dual-headed rod driver, e.g., with rotatable hex heads 404, 406, such as disclosed in co-pending and commonly assigned United States Patent Provisional Application entitled "Multi-Part Assembly for Introducing Axial Implants into the Spine", attorney docket number TranS1041022LLG-6, filed concurrently herewith on Oct. 22, 2004, the disclosure of which is hereby incorporated by reference. More specifically, the implant deployment tool comprises a driver shaft configured to securely engage non-contiguous distal and proximal bodies, respectively, during deployment while maintaining their spatial relationship, i.e., the separation distance, axially, remains constant between the distal and proximal bodies relative one to the other during introduction in vivo. In this manner, mobility preservation apparatus 10 configured with distal and proximal bodies with differential thread pitches, and wherein the major diameter of the first threads 32 of the distal body 16 is less than the major diameter of the second threads 36 of the proximal body 12 and the proximal end of the distal body 16 and the distal end of the proximal body 12 are not mutually engaged, may be axially introduced and distract the cephalad (e.g., L5) vertebral body relative to the caudal (e.g., S1) vertebral body. In an exemplary aspect, the driver tool is configured wherein the more proximal male hex head engaging the proximal body 12 is of larger diameter than that of the distal male hex head engaging the distal body. The distal body 16 is additionally retained in place on the distal head of the dual headed driver during axial advancement (to preclude axial translation) by means of an externally threaded retainer wire which engages internal threads 50 in a distal lumen 46 or distal cavity 48 of the distal body 16. The proximal body 12 is retained in place on the proximal head of the dual headed driver by means of a retaining coupler with male threads on its distal end that engage female threads (socket) in the proximal end of the proximal body 12. The mobility preservation apparatus 10 is advanced in a preloaded configuration on and by means of the driver tool to rotatably engage and distract the vertebral bodies, after which prosthetic nucleus material 60 is sequentially introduced by means as described above, to first fill the disk space surrounding the implant and driver, then with additional prosthetic nucleus material 60 deployed to fill space vacated by the driver 400 once it is disengaged from the proximal and distal bodies and removed from the axial access tract. The distal body 16 may optionally be plugged (e.g., with silicone elastomer tamped into the cannulated space vacated by the distal retention wire) prior to introduction of prosthetic nucleus material 60, and after deployment of prosthetic nucleus material 60, the proximal end of the proximal body 12 is plugged and the site closure is performed as noted above.

Still another embodiment of a mobility preservation apparatus 10 is illustrated in FIGS. 11 to 13, and 29. The mobility preservation apparatus of FIGS. 11 to 13 and 29 generally includes a proximal body 12 and an expandable membrane 18. In one aspect of the present invention, the mobility preservation apparatus may not include an expandable membrane 18. In an exemplary configuration, the overall length of mobility preservation apparatus 10 may range from about 20 mm to about 50mm with the expandable membrane 18 in the expanded position. The mobility preservation apparatus in accordance with the present invention will typically have an aspect ratio of greater than 1.

The proximal body 12 is generally configured to be secured within a vertebral body to position the expandable membrane 18 in or adjacent to the disc space, for example the disc space 860 between L5 and S1. The expandable membrane 18 is generally configured to expand into the disc space 860 to provide a degree of support to adjacent vertebral bodies. Proximal body 12 is generally configured to secure the proximal end of mobility preservation apparatus 10 to a caudally positioned vertebra 800. As illustrated for exemplary purposes throughout the figures, proximal body 12 may include first threads 30 to secure proximal body 12 in a bore 850 through the body of a vertebra.

As illustrated, the proximal body 12 is formed from a single piece of material. The expandable membrane 18 is secured within the lumen 40 for exemplary purposes. Typically, the proximal body 12 is formed by machining or molding as a single piece of material. As illustrated, the proximal body 12 includes a set of first threads 32 to secure proximal body 12 to the body of a caudal vertebra 800. The first threads 32 are illustrated for exemplary purposes as extending over substantially the entire length of proximal body 12. The first threads 32 may include a chamfer to ease insertion and removal of the mobility preservation apparatus 10 from various tools involved with its implantation. The proximal body 12 may define a proximal lumen 42. The proximal lumen 42 of the proximal body 12, as illustrated in FIGS. 1 and 2, may be configured to receive a driver to confer a rotational force to insert, remove or position a mobility preservation apparatus 10 within or between vertebral bodies. In addition, proximal lumen 42 may include internal threads 50 to secure a plug 80, as illustrated in FIGS. 11, 15 and 16 and discussed below.

The expandable membrane 18 is secured to the distal end of the proximal body 12. The expandable membrane 18 is typically secured to the proximal body 12 to permit the expandable membrane 18 to be expanded in situ after the axial implantation of the proximal body within a vertebral body 800, 900. In one aspect, a proximal portion of the expandable membrane 18 is secured to the proximal body and is in fluid communication with the proximal lumen 42 to permit the introduction of a prosthetic nucleus material 60 into the expandable membrane 18. The expandable membrane 18 may be secured to the proximal body 12 using adhesives, mechanical couplings, or otherwise as will be recognized by those skilled in the art. One suitable adhesive for securing the expandable membrane 18 to proximal body 12 is a silicone adhesive. Alternatively, one or more proximal retainer rings 52 may be provided about or within the expandable membrane 18 to secure it to the proximal body 12. The retainer ring 52 may be laser-welded to further secure the ring about the expandable membrane 18. As shown in cross-section in FIGS. 12 and 13 for exemplary purposes, the expandable membrane 18 may include a proximal lip 62 that is received internally within the proximal lumen 42 by a proximal groove 64. The proximal lip 62 of expandable membrane 18 may be compressionally secured in proximal groove 64 by a proximal retaining ring 52 that is compressibly fitted within proximal lumen 42. Further, an adhesive may also be provided to further secure the expandable membrane to the proximal body 12. As illustrated in FIGS. 12 and 13, proximal retaining ring 52 includes internal threads 50 to which plug 80 may be secured. As illustrated, expandable membrane 18 is secured within proximal lumen 42 of proximal body 12. Accordingly, prosthetic nucleus material 60 passing through proximal lumen 42 may forcibly expand the expandable membrane 18. Alternatively, the expandable membrane 18 may be externally secured about the proximal body 12 with a proximal retaining ring 52. The proximal retaining ring 52 can be secured over the expandable membrane 18. In one aspect, the proximal retaining ring 22 may be laser welded to secure them in position. Alternatively and as illustrated, the proximal retaining ring 22 may be sized and configured to compressionally secure portions of the expandable membrane 18 about proximal body 12. As illustrated in FIGS. 13 and 14, expandable membrane 18 is secured between the proximal body 12 and the distal body 16. The expandable membrane 18 may include a proximal lip 62 and a distal lip 66 to engage the proximal body 12 and the distal body 16, respectively. The proximal body 12 may include a proximal groove 64 to receive the proximal lip 62 of the expandable membrane 18. Typically, the proximal groove 64 will extend circumferentially around the proximal body 12 to sealing engage expandable membrane 18.

Similarly with embodiments having a distal body 16, the distal body 16 may include a distal groove 68 to receive the distal lip 66 of the expandable membrane 18. Typically, the distal groove 68 will extend circumferentially around the distal body 16 to sealing engage expandable membrane 18. The expandable membrane 18 may be further secured about the intermediate body 14 by a proximal retaining ring 52 and a distal retaining ring 56. The proximal retaining ring 52 and the distal retaining ring 56 are secured over the expandable membrane 18. In one aspect, the proximal retaining ring 52 and the distal retaining ring 54 may be laser welded to secure them in position. Alternatively, the proximal retaining ring 52 and the distal retaining ring 54 may be sized and configured to compressionally secure portions of the expandable membrane 18 about the intermediate body 14. In addition or alternatively, an adhesive may be provided to bind the expandable membrane 10 to the proximal body 12 and the distal body 16. Regardless of how the expandable membrane 18 is secured, the expandable membrane 18 is sufficiently secure to permit prosthetic nucleus material 60 passing through proximal lumen 42 may forcibly expand the expandable membrane 18 without dislodging the expandable membrane 18.

In one exemplary methodology, the mobility preservation apparatus 10 illustrated in FIGS. 11 to 13 may be implanted trans-sacrally. Where utilizing paracoccygeal entry, a mobility preservation apparatus 10 may be deployed into the L5-S1 spinal motion segment via the trans-sacral axial techniques and instrumentation disclosed in co-pending and commonly assigned U.S. patent application entitled "Access Assembly for Guiding Instrumentation Through Soft Tissue to a Point on the Spine", attorney docket number AXLAMD.015A, filed concurrently herewith on Oct. 22, 2004, the contents of which are hereby incorporated in entirety into this disclosure by reference.

More specifically, in a preferred procedure the blunt-tipped stylet is introduced percutaneously through the guide pin introducer and safely enables advancement of the guide pin introducer through the soft tissue of the pre-sacral track up to the anterior target site on sacral face. The stylet is withdrawn from the guide pin introducer now positioned in place at the target site, and a beveled guide pin of about 0.125" O.D. is inserted, with its handle attached by engagement means of a hex and thumb screw lock, into the guide pin introducer, forming a guide pin-guide pin introducer assembly. Under fluoroscopic guidance to appropriately maintain anterior/posterior alignment, the beveled tip at the distal end of the guide pin is advanced into the sacrum from the target site on the sacral face by means of tapping the proximal end with a hammer or mallet. The guide pin is driven through the sacrum; the L5-S1 disc space, and anchored into L5 prior to bone dilation. The thumb screw is loosened and the guide pin handle is removed from the guide pin's proximal end, to enable attachment of the guide pin extension. The guide pin introducer is then removed without disturbing the guide pin.

Next, a cannulated 6 mm dilator is inserted over the guide pin extension and its distal end is advanced, by means of tapping with a slap hammer, also inserted over the guide wire, against the handle at the proximal end of the dilator, up to (or in close proximity, e.g., within about 6-10 mm) the vertebral end plate. The 6 mm dilator is then withdrawn over the guide pin, and the same process is sequentially repeated using first a cannulated 8 mm dilator, and then a cannulated 10 mm dilator as part of an assembly in engagement with a tapered (approximately 0.375" OD) dilator sheath, respectively inserted over the guide pin and advanced into the sacrum. The dilator handle is then disengaged from the sheath and the dilator is withdrawn over the guide pin, leaving the dilator sheath in place, to preserve trajectory. The guide pin is then removed to enable insertion of a (non-cannulated) 9 mm twist drill through the dilator sheath, which is used to drill, through the large dilator sheath, through S1 into the L5-S1 intervertebral disc.

Then, following removal of the 9 mm drill, the 10 mm dilator tapered large dilator sheath is further advanced, if necessary, through which nucleectomy is performed, by using 3-4 cutters with a plurality of (preferably teardrop shaped) blade configurations, e.g., lengths, and about 6 tissue extraction tools to create an intervertebral disc space 860. After removal of the nucleus pulposus (typically taking care not to scrape cartilage from the vertebral endplates so as to cause bleeding that would enhance undesired fusion) and withdrawal of tissue cutter and extraction tools, typically, an approximately 23" long guide pin of about 0.09" diameter is inserted through the dilator sheath, and the exchange bushing is inserted over the pin, over the dilator sheath and advanced to the target site on the sacral face. Then, the exchange cannula is inserted over the exchange bushing, and left in place following subsequent removal of the bushing. The 10 mm dilator is then inserted into the dilator sheath, to engage and remove it.

As is generally illustrated in FIGS. 22 to 26, mobility preservation apparatus 10 may then be delivered generally via torque driver inserter tools such as driver 400 appropriately configured with male components to engage (e.g., via hex head) female sockets of the mobility preservation apparatus 10 (or a female component on a driver 400 engaging a male component on a mobility preservation apparatus 10 ) within a cannula, over the guide wire and deployed through the exchange system and into, to or proximate the intervertebral disc space 860. The guide pin is removed and disc spaces are augmented with prosthetic nucleus material 60, e.g., by injection through a suitable insertion media injector either into/within an expandable membrane 18 of an accompanying mobility preservation apparatus 10, or via deployment directly into the intervertebral disc space 860, e.g., by engaging the distal end of the inserter with the proximal end of the mobility preservation apparatus 10 and injecting the augmentation media therein, e.g., delivery into a membrane 18 or directly into the intervertebral disc space 860. Deployment of prosthetic nucleus material 60 directly into the intervertebral disc space 860 may be performed by various means and techniques, e.g., an exemplary multi-step procedure wherein a barrier sealant membrane is introduced to seal (e.g., annular) fissures followed by subsequent introduction of bulk prosthetic nucleus material 60.

For example, in deploying a mobility preservation apparatus 10, the distal end of the mobility preservation apparatus 10 is deployed over the proximal end of the extended guide pin and delivered into and through the exchange cannula. More specifically, the proximal end of the proximal body 12 is engaged to a torque (e.g., rotatable) rod driver tool, and the preloaded mobility preservation apparatus 10 is inserted over the guide pin to axially advance, by means of rotation, the implant into S1.

After mobility preservation apparatus 10 deployment in vivo and insertion of the prosthetic nucleus material 60 by means of an appropriate augmentation media inserter, the extended guide pin is reinserted and stop-flow means 80, e.g., typically a cannulated, female-threaded axial rod plug 80, is next inserted, as follows: the proximal end of the plug 80 is fitted on the distal end of the rod driver that is configured (e.g., male hex head) to engage the plug 80, and which is then inserted and axially advanced into the proximal end of the proximal body 12 of the deployed mobility preservation apparatus 10. Next, the plug driver is removed. Once the plug driver has been removed from the access track, site closure is performed by the surgeon.

FIG. 14 illustrates an embodiment of a mobility preservation apparatus 10 having an intermediate body 14 including a cable 170 as the flexible element 22 of intermediate body 14. The cable 170 of intermediate body 14 is generally configured to limit the relative movement between of the proximal body 12 and the distal body 16. An expandable membrane 18, not shown, may be provided about cable 170. The expandable membrane 18 may be sealingly secured to the distal end of the proximal body 12 and the proximal end of the distal body 16. The cable 170 is generally selected to have the flex and compression properties desired for a particular application. For exemplary purposes, cable 170 is illustrated with a core 172 having a plurality of wires 174 spirally wound about the core 172. The cable 170 may be manufactured from a material, such as for example rubbers, silicones, plastics, metals, hard plastics, or composites thereof, among others. Typically, cable 170 is manufactured from a biocompatible material.

FIG. 15 illustrates an embodiment of a mobility preservation apparatus 10 having a having an intermediate body 14 including a plurality of stacked washers 160 as a flexible element 22. The stacked washers 160 are generally configured to limit the relative movement between of the proximal body 12 and the distal body 16. The stacked washers 160 are generally positioned about a cable 170. The cable 170 may be selected to have the flex and compression properties which is cooperation with the particular washer configuration result in the desired properties for the mobility preservation apparatus 10. For exemplary purposes, cable 170 is illustrated with a core 172 having a plurality of wires 174 spirally wound about the core 172. An expandable membrane 18, not shown, may be provided about cable 170. The expandable membrane 18 may be sealingly secured to the distal end of the proximal body 12 and the proximal end of the distal body 16. The washers may be arranged along cable 170 to alternate between compressible washers 162 and non-compressible washers 164, as is illustrated in FIG. 14 for exemplary purposes. The compressible washers 162 may be manufactured from a material having a desired degree of compressibility and elasticity, such as for example rubbers, silicones, plastics, among other materials or combinations of materials. The non-compressible washers 164 may be manufactured from a material having a desired degree of rigidity, such as for example metal, hard plastics, among other materials or combinations of materials. Typically, both the compressible washers 162 and the non-compressible washers 164 are manufactured from biocompatible materials.

FIG. 16*a* illustrates an embodiment of a mobility preservation apparatus 10 having an intermediate body 14 including a flexible element 22 in a ball and track configuration to provide support while allowing relative movement of the proximal body 12 and the distal body 16. The ball and track configuration of flexible element 22 may further provide a degree of translation in the anterior-posterior plane.

generally, the ball and track configuration may include a distally opening concavity 94 defined on a distal end of proximal body 12 and a proximal opening concavity 98 defined on a proximal end of distal body 16 and a movable radially symmetrical pivot 100. Radially symmetrical pivot 100 is illustrated in the figures as a ball for exemplary purposes. Radially symmetrical pivot 100 received within the each of the distally opening concavity 94 and the proximal opening concavity 98 to maintain the relative positions of the proximal body 12 and the distal body 16. In one aspect, the intermediate body 14 including a ball and track configuration may include an expandable membrane 18 or other barrier to prevent material from entering the mobility preservation apparatus and disrupting the function of the ball and track configuration.

As illustrated in FIG. 16, the ball and track configuration for a flexible element 22 includes a first insert 92 defining a distally opening concavity 94 which forms a track to receive a radially symmetrical pivot 100 and a second insert 96 defining a proximal opening concavity 98 to simultaneously receive the radially symmetrical pivot 100. The radially symmetrical pivot 100, first insert 92 and second insert 96 are typically formed from a biocompatible material that is abrasion or wear resistant. The first insert 92 may be configured to be received within the proximal lumen 42 of the proximal body 12. The second insert 98 may be configured to be received within the distal lumen 46 or distal cavity 48 of distal body 16. In one aspect, the first insert 92 and second insert 96 are further configured to be received into the proximal body 12 and distal body 16, respectively, in a manner which allows motion in and out of the anchor but does not allow rotation. Moreover, the first insert 92 and second insert 96 may interface with the proximal body 12 and distal body 16 in a manner where elastomeric bumpers, bushings, or shock absorbers reside at the interfaces. In one embodiment, an insert anchor 102 may be provided within the proximal lumen 42 of the proximal body to secure the first insert 92, second insert 96 and ball 100 within the apparatus.

Situated in between the distally opening concavity 94 and the proximal opening concavity 98 is radially symmetrical pivot 100 that may be formed from the same materials as the proximal body 12 and distal body 16 and/or first insert 92 and second insert 98. The radially symmetrical pivot 100 resides in the distally opening concavity 94 and the proximal opening concavity 98 and may be free to roll and translate within and along one or more elongated concavities which is oriented such that its long axis is substantially parallel to the anterior—posterior axis of the human body. The radially symmetrical pivot 100 may function to receive at least a portion of the weight transferred through the proximal body 12 and the distal body 16. Each of the respective concavities is typically situated in substantially parallel alignment with the corresponding adjacent vertebral endplate and form bearing surface for forces transferred from the spine at least in part through the radially symmetrical pivot 100.

In one aspect, one of the distally opening concavity 94 and the proximal opening concavity 98 may be spherical and the other cavity may be spherical and elongated. The distally opening concavity 94 and the proximal opening concavity 98 may also be configured such that their lengths are the same, and also they are not symmetrical about the centerline, rather, they are offset in the anterior—posterior plane and also oriented to be offset in directions that are opposite with respect to each other, e.g., with the L5 component being offset in the posterior direction and the S1 component being offset in the anterior direction. In this manner, the opposing offsets of elongated concavities may allow the ball 100 to roll anteriorly in flexion and posteriorly in extension.

Figure 16B:
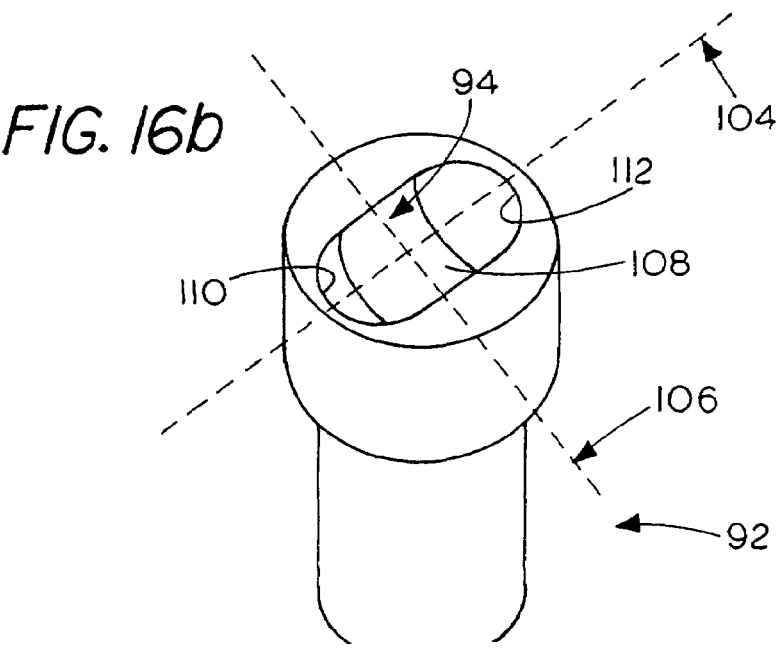

Referring to FIG. 16*b*, there is illustrated a first insert 92 from a ball and track embodiment as described above. In the illustrated embodiment, the distally opening concavity 94 may be characterized by a longitudinal axis 104 and a transverse axis 106. The length of the distal opening concavity 102 along the longitudinal axis may vary from no less than about 50% of the diameter of the corresponding ball to as much as 3 or 4 times the diameter of the corresponding ball. Generally, the longitudinal length of the distal opening concavity 102 will be within the range of from about equal to the diameter of the corresponding ball to about 3 times the diameter of the corresponding ball. In embodiments having a ball with a diameter within the range of from about 5 mm to about 15 mm, the length of the distal opening concavity 102 along the longitudinal axis 104 will often be no greater than about the diameter of the ball plus 5 mm.

The distally opening concavity 94 comprises a generally cylindrical section 108 having a substantially constant radius of curvature. The radius of the cylindrical section 108 may be varied, depending upon the desired lateral range of motion through the ball and track embodiment, as will be apparent to those of skill in the art in view of the disclosure herein. In general, the radius of cylindrical section 108 may be substantially the same as the radius of the corresponding ball, in an embodiment designed to restrict lateral translation across the mobility preservation device. The radius of the cylindrical section 108 may be increased to at least about 105% or 110% or 120% or more of the radius of the ball, in an embodiment in which lateral movement is desirable.

The distal opening concavity 102 is also defined by a first end 110 and a second end 112. In the illustrated embodiment, the first and second ends 110, 112 are provided with constant radius curvature which conforms substantially to a portion of the surface of the ball. Alternatively, the radius of the first and second ends, as measured in a plane which intersects the longitudinal axis 104 and bisects the first insert 92 may be greater than the radius of the ball. In this construction, the first and second ends, in cooperation with the weight of the patient, will provide a dampening effect on the ends of the range of motion of the first insert 92 along longitudinal axis 104 with respect to the corresponding distal insert.

The first insert 92 and corresponding distal insert and ball subassembly may be assembled in place, such by advancing the components sequentially along the access pathway. Alternatively, the opposing inserts and ball may be provided as a subassembly, for insertion as a single unit. This may be accomplished, for example, by providing a tubular polymeric membrane around at least a portion of each of the proximal insert and distal insert, and spanning the region of the ball. Encapsulating the ball and track in a barrier membrane additionally serves to isolate the ball and track from tissue ingrowth and body fluids.

Figure 17:
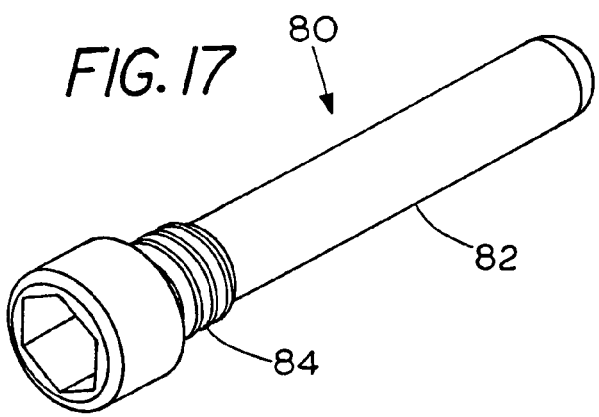
FIG. 17 illustrates a perspective view of an embodiment of a plug in accordance with the present invention.
Figure 18:
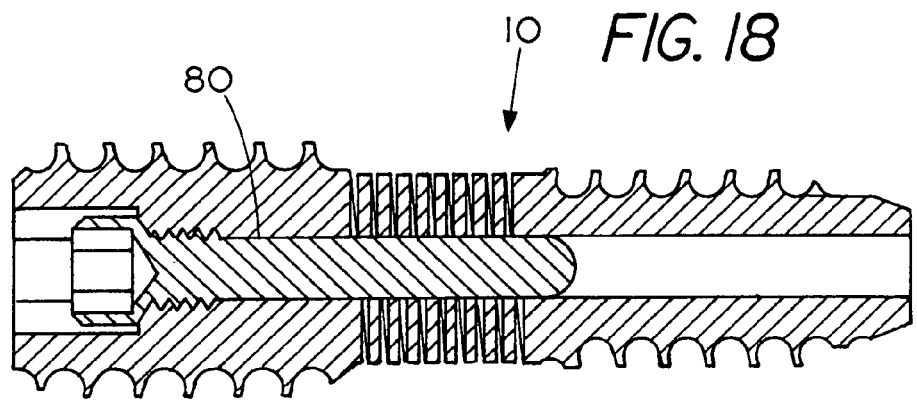
FIG. 18 illustrates a cross-section of a side view of an embodiment of a mobility preservation apparatus in accordance with the present invention including a plug within the proximal lumen and intermediate lumen.

In another aspect of the present invention, a plug 80 may be provided to be received within proximal lumen 42 and/or intermediate lumen 44. Exemplary embodiments of plug 80 are illustrated in FIGS. 13, 17 and 18. As illustrated, plug 80 is configured to be inserted into the caudad end of proximal lumen 42. Plug 80 may be provided with a stiffening member 82. FIGS. 17 and 18 illustrate plug 80 and stiffening member 82 as an integral component for exemplary purposes. Plug 80 may be provided to preclude leakage or migration of the osteogenic, osteoconductive, or osteoinductive gel or paste, any fluid prosthetic nucleus material which may have been inserted into the disc space 860 following a nucleectomy procedure or after implantation of a mobility preservation apparatus 10 as well as any other fluid or discharge from the nucleus. Accordingly, the plug 80 is typically configured to be secured within the proximal lumen 42 at a location caudad to the most caudad positioned fenestration 74 although the plug 80 may be secured in the intermediate lumen 44, the distal lumen 46 or the distal cavity 48 in certain configurations. In one aspect, plug 80 provides a seal to substantially prevent fluid migration through proximal lumen 42. External threads 84 may be provided to secure plug 80 in proximal lumen 42. As illustrated, external threads 52 may be rotatably received by the internal threads 50 of lumen 40. As illustrated for exemplary purposes, plug 80 is configured to be inserted using a hex-head driver. Plug 80 may be fabricated from stainless steel, other suitable metals or alloys, or suitable polymeric material as will be recognized by those skilled in the art.

The stiffening member 82 may also or alternatively be secured within a lumen of mobility preservation apparatus 10. Stiffening member 82 may be provided with external threads 84 to secure the stiffening member 82 within proximal lumen 42 and/or intermediate lumen 44. When extending into the intermediate lumen 44, stiffening member 82 may stiffen the intermediate body 44 to convert the mobility preservation apparatus 10 functionally into a fusion apparatus depending on how much the mobility preservation apparatus 10 is stiffened by the addition of the stiffening member 82. In one aspect, the intermediate body may be stiffened by having the stiffening member 82 extend to or beyond the flexible element 22 of the intermediate body 14. As illustrated, external threads 84 may be rotatably received by the internal threads 50 of proximal lumen 42. As illustrated for exemplary purposes, stiffening member 82 is configured to be inserted using a hex-head driver, which may be configured as a driver 400 illustrated in FIGS. 22 to 26. Stiffening member 82 may be configured to increase the stiffness of a mobility preservation apparatus 10. Further, a stiffening member 82 may function to abut fenestrations 74 to preclude any fluid leakage. The stiffening member 82 may be configured in a variety of shapes and sizes and made from a wide range of materials to achieve the desired modification to the flex properties of a mobility preservation apparatus. Stiffening member 82 may be fabricated from stainless steel, other suitable metals or alloys, or suitable polymeric material as will be recognized by those skilled in the art. A series of distinct fusion rods may be indicated to provide a progression of therapy in a single patient over time or a single stiffening member 82 may be provided at the time of implantation of the mobility preservation apparatus 10. For example, a plug 80 having an integral stiffening member 82 inserted into intermediate lumen 44 may extend sufficiently through and distally into the intermediate lumen 44 to reduce the flexibility of the intermediate body 14 so that it effectively serves as an immobilization or fusion device.

Figure 19:
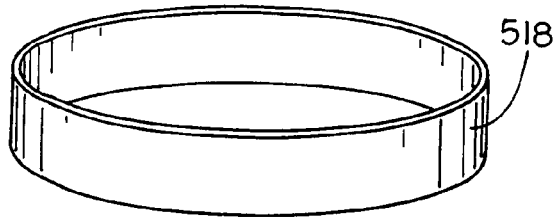
FIG. 19 illustrates a perspective view of a collar in accordance with the present invention.
Figure 20:
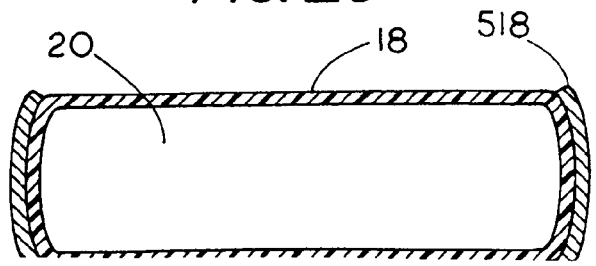
FIG. 20 illustrates a cross-section of a side view of a collar secured to an expandable membrane.

As illustrated in FIGS. 19 and 20, a collar 518 may be deployed about the expandable membrane 18 of the mobility preservation apparatus 10. Typically, the collar 518 is positioned radially about the expanded expandable membrane in disc space 860. The collar 518 is generally configured to modify the expansion characteristics of the expandable membrane 18. In one aspect, the collar 518 may be configured to reinforce the annulus. The collar 518 may be integral with the expandable membrane or may be a separate component. When integral, the collar 518 may be formed as a thickened region of material around the expandable membrane 18 and may be integrally formed. Alternatively, an integral collar 518 may be mechanically and/or chemically attached to the expandable membrane 18 such as for example with an adhesive. When separate, the collar 518 may be positioned in situ prior to implantation although collar 518 may be configured on or within expandable membrane 18. In one aspect, the collar 518 is silicone or polyurethane and is configured to conform to the annulus to prevent migration or leakage of the membrane through herniations. Accordingly, the collar 518 is typically stiffer than the expandable membrane 18. In a one embodiment, the collar is from between about 8 mm-12 mm high and about 0.5 to 1.0 mm thick. In operation, the collar 518 may be configured to abut the annulus from the inside and to share load with the annulus under higher stress conditions and also be strong enough to buttress any weak or herniated portions of annulus.

Figure 22:
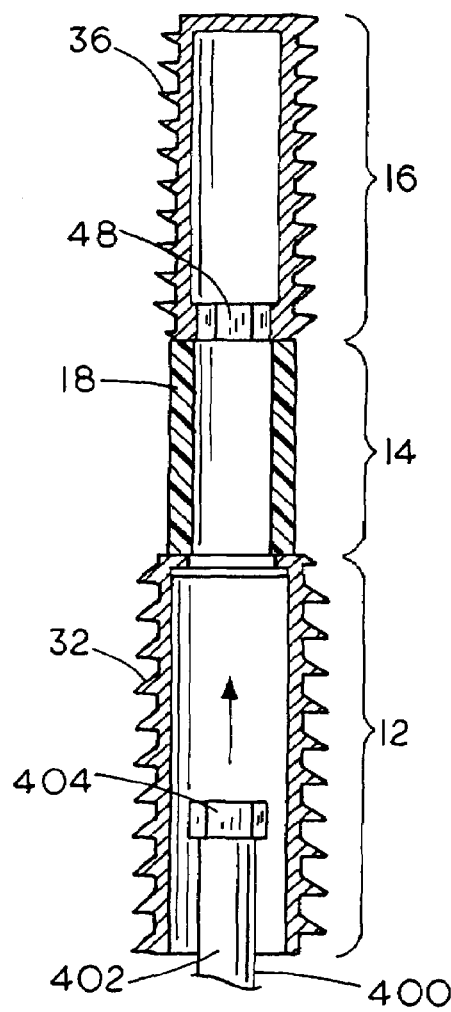
FIG. 22 illustrates a partial cross-section of an embodiment of a proximal body of a mobility preservation apparatus in accordance with the present invention receiving a driver.
Figure 23:
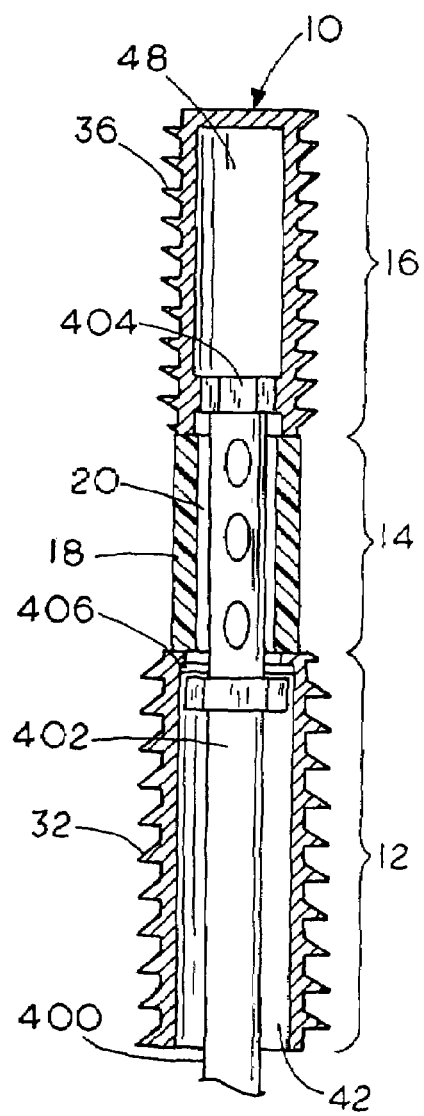
FIG. 23 illustrates a partial cross-section of an embodiment of a mobility preservation apparatus in accordance with the present invention with a driver positioned to axially rotate the mobility preservation apparatus with the illustrated driver incorporating an introducer to infuse prosthetic nucleus material into the intervertebral disc space.

FIGS. 22 and 26 illustrate an exemplary embodiment of a driver 400 to position an embodiment of a mobility preservation apparatus 10 within a patient. As illustrated, the driver 400 includes an elongated drive shaft 402 having a distal drive head 404. A proximal drive head 406 may also be provided at a proximal position along drive shaft 402. Distal drive head 404 and proximal drive head 406 are illustrated with a hexagonal shape in axial cross section for exemplary purposes. Distal drive head 404 and proximal drive head 406 may be generally configured to be received by or to receive an aspect of a mobility preservation apparatus 10 to confer a rotational force for the purposes of implanting or positioning the mobility preservation apparatus. Accordingly, drive shaft 404 may be configured to confer a rotational force to drive head 404 where the rotational force originates from a location outside of the patient.

As discussed above and illustrated in FIGS. 24, 26, 27, 28, 30, 33, and 34, the mobility preservation apparatus 10 may be introduced via the axial pathway or bore 850 through at least one vertebral body of a caudal vertebra 800, across an intervertebral disc space 860, and into a vertebral body of a cephalad vertebra 900. Here, the cephalad end of the mobility preservation apparatus 10 may be inserted into place by a driver 400 engaged to the caudad end of the apparatus, and by manually turning it like a screw. In a multi-piece apparatus, the mobility preservation apparatus 10 may be rotated into place by first rotating on the caudad end of the distal body 16 of the apparatus into the cephalad vertebra 900 prior to insertion of the intermediate body 14 and proximal body 12. This insertion method as just described may be used for both apparatus deployment and/or for distraction. After the distal body 16 is seated into the axial pathway or bore 850 through a vertebral body, the mobility preservation apparatus 10 may be rotated in the cephalad direction to cause the second threads 36 to screw into the wall of the axial pathway or bore 850. The diameter of the axial bore 850 may be matched to the largest minor thread diameter of the mobility preservation apparatus 10. Generally, the mobility preservation apparatus 10 has been properly positioned when at least a portion of the intermediate body 14 and/or expandable membrane 18 is positioned within the disc space 860. However, proper positioning will vary depending upon the particular embodiment of the mobility preservation apparatus 10 and the condition of the patient.

In another aspect of the present invention, a mobility preservation apparatus 10 may be provided with a prosthetic nucleus either by forming the prosthetic nucleus in situ or by inserting a pre-formed prosthetic nucleus 200 as illustrated in FIGS. 30 to 32. The prosthetic nuclei may be manufactured from a wide range of prosthetic nucleus materials 60 such as for example silicone, polyurethane, hydrogel, among others. If using a hydrogel, polyethylene glycol (PEG) is an example of a hydrogel with adequate physical properties. In one aspect, the prosthetic nucleus material 60 approximates the physiological properties (e.g., biomechanical; hydrophicity) of natural nucleus. Accordingly, the prosthetic nucleus material 60 may have a Shore D range from between A10 to D90. One exemplary prosthetic nucleus material 60 for the mobility preservation apparatus may include a cross-linked hyaluronic acid. Similarly, many natural and man-made hydrogels can be configured to achieve similar properties.

A prosthetic nucleus 200 may be formed in situ within the disc space 860 after or prior to implantation of a mobility preservation apparatus 10. In one embodiment, the mobility preservation apparatus 10 includes a prosthetic nucleus formed from a prosthetic nucleus material 60 infused into the disc space 860. By flowing into the disc space 860, the prosthetic nucleus material 60 may fill the disc space. Further, the prosthetic nucleus material 60 may conform to and match the disc space 860 created during the nucleotomy procedure. As illustrated in FIGS. 26 to 29 and 34, the formation of a prosthetic nucleus 200 about a mobility preservation apparatus 10 in situ may include the introduction of a liquid or granular prosthetic nucleus material 60 through proximal lumen 42 of a mobility preservation apparatus 10 and into the disc space 860 through fenestrations 74 or through proximal lumen 42 of the mobility preservation apparatus 10. The prosthetic nucleus material 60 may be introduced into the mobility preservation apparatus 10 with an elongated introducer 500 which is positioned to introduce the prosthetic nucleus material 60 into the lumen 40 of the mobility preservation apparatus 10 or directly into fenestrations 74, as illustrated in FIG. 30. After the disc space 860 has been adequately filled, a plug 80 or a distraction rod may be secured within the lumen 40 to prevent the prosthetic nucleus material 60 from leaking from the disc space 860. Alternatively, the prosthetic nucleus material 60 may polymerize within the disc space 860 or the lumen 40 may be otherwise sealed to eliminate the need for plugging the proximal lumen 42 and/or fenestrations 74. In other aspects, it may be preferable to seal the access bore 850 in the sacrum in order to prevent the escape of the prosthetic nucleus material 60. A variety of configurations of plugs and/or seals known in the art can be used to seal the access bore 850, such as, for example, absorbable or non-absorbable threaded plugs, conventional poly-methylmethacrylate (PMMA) bone cement, autologous or allograft bone dowels, and combinations thereof. This approach is most applicable in situations where the annulus is fully intact, or has been otherwise sealed to preclude potential leaking or migration of material from within the disc space 860 through annular fissures, lesions, or herniations.

In another variation of the present invention, the previously noted spatial discrepancy between the mobility preservation apparatus 10 and the remaining nucleus or annulus is obviated by prosthetic nucleus materials which are deployed directly into the intervertebral disc space 860 to augment or replace the intervertebral disc, after which the access tract is sealed in order to retain the prosthetic nucleus material by precluding migration or expulsion More specifically, prosthetic nucleus material 60, independent of a containment membrane or envelope, is introduced directly into the prepared intervertebral disc space 860, when the annulus is known to be intact. In this embodiment, the prosthetic nucleus material serves as the "air" in the "tire" of the disc, and is selected based on, among other attributes, biocompatibility; resistance to fractional mass loss over time and hence ability to provide or maintain distraction over time; distribute loads (hydrostatic pressure in the disc), for example, to restore tensile hoop stress in the annulus. The prosthetic nucleus material 60 preferably comprises biomedical grade hydrogels or blends thereof (e.g., hydrogel/hydrogel, or hydrogel/elastomer). Cross-linked hyaluronic acid, such as is available from Fidia Corporation in Italy, is an example of a suitable material, however, many natural and man-made hydrogels or blends thereof may be configured to achieve similar properties without inflammatory response. The efficacy of this embodiment for its intended function is further predicated on the requirement that the access site to the disc space 860 is sealed to preclude prosthetic nucleus material migration or expulsion. Any one of numerous valve configurations, e.g., self-sealing valve assemblies or flow-stop devices may suitably serve this function. Materials suitable for anchoring are similarly suitable as plugs, such as non-absorbable threaded plugs, including those fabricated from medical grade polyether-ether-ketone (PEEK) such as that commercially available from Invibio Inc., in Lancashire, United Kingdom, or polyether-ketone-ketone PEKK available from Coors-Tech Corporation, in Colorado, or alternatively, conventional polymethylmethacrylate (PMMA); ultra high molecular weight polyethylene (UHMWPE), or other suitable polymers in combination with autologous or allograft bone dowels may be used as plugs.

One advantage of this embodiment as just described would be the concomitant use of prosthetic nucleus material 60 comprising hydrogels as in situ delivery vehicles for a range of therapeutic compounds such as, for example, progenitor cells analgesic and the like (e.g., capitalizing on their biodegradability, through chemical hydrolysis or as enzymatically catalyzed). Moreover, certain bioactive hydrogels (e.g., such as those based on photo-crosslinked poly(ethylene oxide) [PEO], or block polypeptide or amino acid hydrogels), may be used in one aspect of the present invention to engineer tissue, e.g., cartilage; or to serve as a dimensional matrix that promotes nerve regeneration, or reduces scar tissue formation.

Once positioned, a prosthetic nucleus may be formed in situ by expanding the expandable membrane 18 with a prosthetic nucleus material 60 as generally illustrated in FIGS. 26, 27, 29, and 34. In one aspect, the prosthetic nucleus material 60 approximates the physiological properties (e.g., biomechanical; hydrophicity) of natural nucleus. For example, one appropriate prosthetic nucleus material 60 for the mobility preservation apparatus may include a cross-linked hyaluronic acid. Similarly, many natural and man-made hydrogels can be configured to achieve similar properties.

As is generally illustrated in the FIGS. 26 to 29 and 34, a prosthetic nucleus may be formed in situ within the disc space 860 after implantation of a mobility preservation apparatus 10. In one embodiment, the apparatus 10 includes a prosthetic nucleus formed from a prosthetic nucleus material 60 infused into the disc space 860. By flowing into the disc space 860, the prosthetic nucleus material 60 may fill the disc space. Further, the prosthetic nucleus material 60 may conform to and match the disc space 860 created during the nucleotomy procedure. As illustrated in FIGS. 8 and 9, the formation of a prosthetic nucleus 200 about a mobility preservation apparatus 10 in situ may include the introduction of a liquid or granular prosthetic nucleus material 60 through proximal lumen 42 of a mobility preservation apparatus 10 and into the disc space 860 through fenestrations 74 of the mobility preservation apparatus 10. The prosthetic nucleus material 60 may be introduced into the apparatus with an elongated introducer 500 which is positioned to introduce the prosthetic nucleus material 60 into the lumen 40 of the mobility preservation apparatus 10 or directly into fenestrations 74. After the disc space 860 has been adequately filled, a plug 80 or distraction rod 60 may be secured within the lumen 40 to prevent the prosthetic nucleus material 60 from leaking from the disc space. Alternatively, prosthetic nucleus material 60 may polymerize within the disc space 860 or the lumen 40 may be otherwise sealed to eliminate the need for plugging the lumen 40 and or fenestrations 74. In other aspects, it may be preferable to seal the access hole 850 in the sacrum in order to prevent the escape of the prosthetic nucleus material 60. A variety of configurations of plugs and/or seals known in the art can be used to seal the access hole 850, such as, for example, absorbable or non-absorbable threaded plugs, conventional poly-methyl-methacrylate (PMMA) bone cement, autologous or allograft bone dowels, and combinations thereof. This approach is most applicable in situations where the annulus is fully intact, or has been otherwise sealed to preclude potential leaking or migration of material from within the disc space 860 through annular fissures, lesions, or herniations.

If there is a tear or fissure in the annulus, it could be repaired using a device that is passed through the dilator sheath following the creation of a channel into the disc space 860 (using bone dilation, drilling, or a combination of the two). The device could tunnel through the disc material and deliver a glue (such as cyanoacrylate or a fibrin based glue) substance to bolster the internal lamina of the disc annulus. Such a delivery device could be made out of several materials including nitinol tubing, or a flexible plastic material such as polyethylene. The device would have to fit within the dilator sheath (Sheath ID=0.355") and be at least 10" in length to track from outside the body to the site of application. The ID of the delivery device needs to be large enough to allow insertion of the osteogenic promoter material which may very in viscosity (chunks or paste) depending on the need. A flexible tube is inserted through the dilator sheath, or alternatively through a fenestrated plug or rod into the disc space 860 to deliver such augmentation material.

In yet another aspect of the present invention, a preformed prosthetic nucleus 200 can be deployed in the disc space 860 as illustrated in FIGS. 30 to 32. Once deployed, the preformed prosthetic nucleus may occupy at least a portion of the disc space 860 to provide additional load bearing surface and capability, shock absorbing capacity, and additional cushioning and resistance in motion. In this aspect of the present invention, mobility preservation apparatus 10 may include a preformed prosthetic nucleus 200. In general, the preformed prosthetic nucleus 200 interfaces in contact with proximal and distal vertebral bodies after implantation about a mobility preservation apparatus 10.

With reference to FIGS. 30 to 32, in accordance with one aspect of the present invention, there is provided a preformed prosthetic nucleus 200 for replacing or augmenting the spinal disc nucleus comprising a superior surface 532 for contacting an adjacent, superior vertebral body end plate 533, an inferior surface 534, for contacting an adjacent, inferior vertebral body end plate 535, and a radial surface 536, for facing in the direction of an annulus 408. In one embodiment, the superior and inferior surfaces 532, 534 preferably have a compliancy sufficient to permit conformation to the respective, adjacent end plates 533, 535, and the physical characteristics of the preformed prosthesis 200 are selected such that a first portion or component of an axial compression force exerted on the prosthesis 200 is transferred across the prosthesis 200 to the superior and inferior end plates 533, 535, while a second portion of the axial compression force is deflected laterally in the direction of the annulus 408 (and/or via means of an intervening elastomeric collar) to allow load sharing by the annulus.

The outer wall of the preformed prosthetic nucleus 200 preferably includes a compliant membrane. With reference to FIGS. 11a, 12a and 12b, in one embodiment, compliancy of the radial surface 536 is less than the compliancy of at least one of the superior and inferior surfaces 532, 534. In another embodiment, the wall supporting the radial surface 536 is semi-compliant, e.g., is stiffer or has a greater thickness than the walls supporting the superior and inferior surfaces 532, 534.

In yet another embodiment, the preformed prosthetic nucleus 200 may include a collar 518 carried by or within the radial surface 536. An exemplary embodiment of an collar 518 is illustrated in FIGS. 19 and 20. As illustrated, the pre-formed prosthesis resumes its pre-formed shape once implanted inside the treatment site, such as, for example, the disc space.

In one embodiment, shown in FIG. 31, the prosthesis 200 is preformed, designed, or biased in a manner so that the prosthesis 200 naturally assumes a partially open donut or ring structure or shape, where the leading and distal ends 540, 542 of the prosthesis 200 are located near each other. Here, the leading end 540 and distal end 542 move and remain close to each other without actually touching, thereby leaving a space in between them, so that the prosthesis 200 assumes a C-shape with the ends 540, 542 close to each other. In another embodiment, not illustrated, the ends 540, 542 come into contact with each other, thereby closing the gap between the ends 540, 542 so that prosthesis 200 forms a closed donut or ring structure.

With reference to FIG. 30, in one embodiment, one or more sections of the prosthesis 200 can be temporarily straightened or re-shaped for the purpose of introducing the prosthesis 200 into the treatment site, such as, for example, the disc space 860 resulting from a nucleotomy or discectomy procedure. With reference to FIG. 32, the prosthesis 200 preferably re-forms or resumes its natural shape. In this particular embodiment, the natural shape is a donut or ring shape. It will be understood, the natural shape or bias of the preformed prosthesis 200 can be any shape or configuration appropriate for a given application or treatment. It will also be understood that the prosthesis 200 does not necessarily assume the identical preformed shape or structure within the treatment site. Here, variations in the shape of the prosthesis 200 in the treatment site will depend on factors, such as, the area and shape of any structures in the treatment site. However, in it will be understood that the preformed shape of the prosthesis 200 will preferably be selected or determined with the shape, area, and/or geometry of the treatment site in mind.

With reference to FIG. 30, in one approach, the method of implanting the preformed prosthesis 200 into a treatment site includes the steps of introducing a modified distraction rod 550, in axial alignment with the longitudinal axis of the vertebral motion segment using the anterior method into the treatment site. For this particular illustrative embodiment, the treatment site includes a disc space 860 and portions of the superior and inferior vertebral bodies 800, 900 that abut the disc space 860. Here the modified distraction rod 550 includes a lumen 552 extending along at least a portion of the length of the rod 550, an aperture 554 allowing communication between the lumen 552 and the disc space 860, and appropriately selected threads 556, 558 on the leading and trailing sections of the rod 550 to achieve the desired degree of distraction of the vertebral bodies 800, 900. In one approach, the vertebral bodies are "over distracted" to facilitate the introduction of the preformed prosthesis 200 into the disc space 860. In another approach, the vertebral bodies are distracted just enough to allow entry of the prosthesis 200 into the disc space.

The method of implanting the preformed prosthesis 200 into a treatment site may also include the steps of advancing the preformed prosthesis 200 through the lumen 552 of the rod 550, and advancing the prosthesis 200 into the disc space 860 through the aperture 554. In one approach, illustrated in FIG. 30, the prosthesis 200 is advanced or pushed through the lumen 552 of the rod 550 and into the disc space 860 by a push-rod. The push rod 560 is configured and dimensioned to fit within the lumen 552 and has a prosthesis-engaging structure 562 on its leading end. In one embodiment, shown in FIG. 12a, the prosthesis-engaging structure 562 includes a concave or cupped structure which engages with the trailing end 542 of the prosthesis 530. Here, the prosthesis 200 is advanced through the rod 550 and into the disc space 860 by pushing the push-rod 560 in the cephalad direction. In this particular embodiment, the rod 550 includes a curved wall 555 that directs the prosthesis 200 toward the aperture 554 and out into the disc space 860 as the 200 prosthesis is advanced cephalad.

Once inside the disc space, the prosthesis 200 assumes its preformed shape—namely, a partially open donut shape in this particular illustrative embodiment (see FIGS. 11a and 11b). In one approach, the rod 550 is removed so that the vertebral bodies 800, 900 settle toward each other and onto the prosthesis 200, thereby causing the prosthesis to slightly bulge radially outward toward the annulus. It will be understood that the materials and dimensions of the preformed prosthesis 200 are selected in a manner so that the prosthesis mimics the properties of natural, healthy nucleus material. The material and dimensions of the prosthesis will depend on numerous factors, such as, for example, the size of the disc space 860 or treatment site, the size and anatomical characteristics of the patient, etc.

In accordance with another aspect of the present invention, there is provided a mobility preservation apparatus 10 comprising an elastic sleeve structure illustrated in FIGS. 33 and 34. The elastic sleeve prosthesis 400 may have a proximal body 12, a distal body 16, and an intermediate body 14 which are substantially continuous in structure. The prosthesis 400 comprises a mesh structure. The prosthesis 400 can me made of any number of suitable materials known in the art, such as, for example, an elastomerll. It will be understood that the material(s) of used to form the mesh structure of the mobility preservation apparatus 10 are preferably semi-compliant. As used herein, semi-compliant refers to biomechanical properties, e.g., modulus, that permit conformability with the pertinent vertebral structures but that do not render the device too compressible such that it would be able to extrude from the disc space 860 (e.g., through herniations in the annulus, or back through the deployment pathway) nor so stiff that loads are not distributed to!shared by physiological structures (potentially leading to, for example, transition syndrome). In another embodiment, the elastic sleeve 400 of the mobility preservation apparatus 10 comprises a solid or non-mesh structure. As with the mesh structure, the material(s) of the mobility preservation apparatus 10 are semi-compliant, that is balanced to be firm yet flexible and resilient.

With reference to FIGS. 33 and 34, in one exemplary approach, the elastic sleeve 400 is inserted into the treatment site comprising a disc space 860 and sections of the two vertebral bodies 800, 900 abutting the disc space 860. In one preferred approach, the elastic sleeve 400 is introduced into treatment site after the vertebral bodies 800, 900 have been distracted. With reference to FIG. 34, after the elastic sleeve 400 is inserted into the disc space 860 and any distraction tools or mechanisms (not shown) have been removed, the vertebral bodies 800, 900 settle toward each other and onto the elastic sleeve 400 in a manner that causes the intermediate body 14 of the elastic sleeve 400 to bulge radially outward toward the annulus 408 so that a superior surface 578, an inferior surface 580, and a radial surface 582 form near the intermediate body 14 of the elastic sleeve 400. Here, the superior surface 578 contacts or engages with a superior vertebral body end plate 533, the inferior surface 580 engages with an inferior vertebral body end plate 535, and the radial surface 582 faces in the direction of the annulus 408. In one embodiment, the radial surface 582 engages with nucleus material between the elastic sleeve 400 and the annulus 408. In another embodiment, the radial surface 582 engages directly with the annulus 408.

With continued reference to FIG. 34, the prosthesis 400 provides axial compressive strength at the treatment site. In one embodiment, a first portion or component of an axial compression force exerted on the prosthesis 400 is transferred across the prosthesis 400 to the superior and inferior end plates 533, 535, while a second portion of the axial compression force is deflected laterally in the direction of the annulus 408 to allow load sharing by the annulus 408. In one preferred embodiment, the elastic sleeve 400 abuts the annulus 408, thereby facilitating the transfer a portion of any axial compression force(s) as lateral force(s) for absorption by the annulus 408. While the present invention has been illustrated and described with particularity in terms of preferred embodiments, it should be understood that no limitation of the scope of the invention is intended thereby.

While the present invention has been illustrated and described with particularity in terms of preferred embodiments, it should be understood that no limitation of the scope of the invention is intended thereby. Features of any of the foregoing methods, and exemplary devices shown and briefly described below, may be substituted or added into the others, as will be apparent to those of skill in the art. The scope of the invention is in no way intended to be limited by the brevity or exemplary nature of the material below, and may be further understood from the accompanying Figures. It should also be understood that variations of the particular embodiments described herein incorporating the principles of the present invention will occur to those of ordinary skill in the art and yet be within the scope of the materials described and shown herein.

Features of any of the foregoing methods and devices may be substituted or added into the others, as will be apparent to those of skill in the art. It should also be understood that variations of the particular embodiments described herein incorporating the principles of the present invention will occur to those of ordinary skill in the art and yet be within the scope of this disclosure.

The invention claimed is:

1. An implantable spinal mobility preservation apparatus, comprising:
   a intermediate body having a proximal end and a distal end and including at least one flexible element positioned between the proximal end and the distal end;
   a proximal body including a first retention structure secured to the proximal end of the intermediate body and defining a proximal lumen, with the first retention structure comprising a first external thread oriented for engagement of an axial bore through an caudad vertebral body;
   a distal body including a second retention structure secured to the distal end of the intermediate body, with the second retention structure comprising a second external thread oriented for engagement of an axial bore through a cephalad vertebral body wherein the pitch of the second external thread is finer than the pitch of the first external thread to induce distraction between the caudad vertebral body and the cephalad vertebral body during implantation; and
   an expandable membrane secured over at least a portion of the intermediate body, the proximal body, the intermediate body, and the distal body defining a longitudinal axis, with the combination of the proximal body, the intermediate body and the distal body having an aspect ratio of greater than 1 wherein the aspect ratio is the ratio of an overall length along the longitudinal axis to a largest diameter along the overall length with the expandable membrane in an unexpanded configuration.

2. An implantable spinal mobility preservation apparatus, comprising:
   a intermediate body having a proximal end and a distal end and including at least one flexible element positioned between the proximal end and the distal end;
   a proximal body including a first retention structure secured to the proximal end of the intermediate body and defining a proximal lumen;
   a distal body including a second retention structure secured to the distal end of the intermediate body;
   an expandable membrane secured over at least a portion of the intermediate body, the proximal body, the intermediate body, and the distal body defining a longitudinal axis, the expandable membrane defining an expansion chamber and the expansion chamber in fluid communication with the proximal lumen, and with the combination of the proximal body, the intermediate body and the distal body having an aspect ratio of greater than 1 wherein the aspect ratio is the ratio of an overall length along the longitudinal axis to a largest diameter along the overall length with the expandable membrane in an unexpanded configuration; and
   a prosthetic nucleus material positioned within the expansion chamber wherein the prosthetic nucleus material is an elastomeric solid.

3. An implantable spinal mobility preservation apparatus, comprising:
   a intermediate body having a proximal end and a distal end and including at least one flexible element positioned between the proximal end and the distal end;
   a proximal body including a first retention structure secured to the proximal end of the intermediate body and defining a proximal lumen;
   a distal body including a second retention structure secured to the distal end of the intermediate body;
   an expandable membrane secured over at least a portion of the intermediate body, the proximal body, the intermediate body, and the distal body defining a longitudinal axis, the expandable membrane defining an expansion chamber and the expansion chamber in fluid communication with the proximal lumen, and with the combination of the proximal body, the intermediate body and the distal body having an aspect ratio of greater than 1 wherein the aspect ratio is the ratio of an overall length along the longitudinal axis to a largest diameter along the overall length with the expandable membrane in an unexpanded configuration; and a prosthetic nucleus material positioned within the expansion chamber wherein a proximal surface and a distal surface have a greater compliancy than a radial surface.

4. A method for supporting the spine, comprising:

providing an implantable spinal mobility preservation apparatus having a intermediate body having a proximal end and a distal end and including at least one flexible element positioned between the proximal and the distal end, a proximal body including a first retention structure secured to the proximal end of the intermediate body, the proximal body defining a proximal lumen, a distal body including a second retention structure secured to the distal end of the intermediate body, and an expandable membrane secured over at least a portion of the intermediate body, the expandable membrane defining an expansion chamber and the proximal lumen providing an internal path for fluid communication from a proximal end of the proximal body to an expansion chamber of the expandable membrane;

forming an axial bore through a caudad vertebral body, an intervertebral disc and a cephalad vertebral body;

removing at least a portion of a nucleus pulposus of the intervertebral disc through the axial bore to form a disc space; and axially inserting the implantable spinal mobility preservation apparatus through the axial bore;

securing the distal body of the implantable mobility preservation apparatus in the cephalad vertebral body;

securing the proximal body of the implantable mobility preservation apparatus in the caudad vertebral body; and providing a prosthetic nucleus material through the proximal lumen into the expansion chamber of the spinal mobility preservation apparatus.

5. An implantable spinal mobility preservation apparatus, comprising:

a intermediate body configured in the shape of a rod and defining a longitudinal axis and having a proximal end and a distal end, the intermediate body including at least one flexible element positioned between the proximal and the distal end to increase the flexibility of the intermediate body, the intermediate body defining an intermediate lumen, and the intermediate body defining at least one fenestration, the one or more fenestrations in fluid communication with the intermediate lumen;

a proximal body configured in the share of a rod and defining a longitudinal axis, the proximal body secured to the proximal end of the intermediate body, the proximal body including a first external thread to rotatably position the proximal body through an axial bore in a body of a caudad vertebra, the proximal body defining a proximal lumen in fluid communication with the at least one fenestration of the intermediate body;

a distal body configured in the shape of a rod and defining a longitudinal axis, the distal body secured to the distal end of the intermediate body, the distal body including second external thread to rotatably position the distal body through an axial bore in a body of a cephalad vertebra;

an expandable membrane having a substantially tubular shape, the expandable membrane secured over at least a portion of intermediate body which includes the at least one fenestration. the expandable membrane defining an expansion chamber in fluid communication with the at least one fenestration of the intermediate body; and the longitudinal axis of the proximal body, the longitudinal axis of the intermediate body and the longitudinal axis of the distal body aligned substantially coaxial with one another.

6. An implantable spinal mobility preservation apparatus, comprising:

a intermediate body configured in the shape of a rod and defining a longitudinal axis and having a proximal end and a distal end, the intermediate body including at least one flexible element positioned between the proximal and the distal end to increase the flexibility of the intermediate body, and the intermediate body defining at least one fenestration;

a proximal body configured in the shape of a rod and defining a longitudinal axis, the proximal body secured to the proximal end of the intermediate body, the proximal body including a first external thread to rotatably position the proximal body through an axial bore in a body of a caudad vertebra, the proximal body defining a proximal lumen in fluid communication with the at least one fenestration of the intermediate body the proximal lumen configured to receive a driver substantially aligned along the longitudinal axis of at least the proximal body;

a distal body configured in the shape of a rod and defining a longitudinal axis, the distal body secured to the distal end of the intermediate body, the distal body including second external thread to rotatably position the distal body through an axial bore in a body of a cephalad vertebra;

an expandable membrane having a substantially tubular shape, the expandable membrane secured over at least a portion of intermediate body which includes the at least one fenestration, the expandable membrane defining an expansion chamber in fluid communication with the at least one fenestration of the intermediate body: and the longitudinal axis of the proximal body, the longitudinal axis of the intermediate body and the longitudinal axis of the distal body aligned substantially coaxial with one another.

7. An implantable spinal mobility preservation apparatus, comprising:

a intermediate body configured in the shape of a rod and defining a longitudinal axis and having a proximal end and a distal end, the intermediate body including at least one flexible element positioned between the proximal and the distal end to increase the flexibility of the intermediate body, and the intermediate body defining at least one fenestration;

a proximal body configured in the shape of a rod and defining a longitudinal axis, the proximal body secured to the proximal end of the intermediate body, the proximal body including a first external thread to rotatably position the proximal body through an axial bore in a body of a caudad vertebra, the proximal body defining a proximal lumen in fluid communication with the at least one fenestration of the intermediate body:

a distal body configured in the shape of a rod and defining a longitudinal axis, the distal body secured to the distal end of the intermediate body, the distal body including second external thread to rotatably position the distal body through an axial bore in a body of a cephalad vertebra wherein the pitch of the second external thread is finer than the pitch of the first external thread to induce distraction between the body of the caudad vertebra and the body of the cephalad vertebra during implantation;

an expandable membrane having a substantially tubular shape, the expandable membrane secured over at least a portion of intermediate body which includes the at least one fenestration, the expandable membrane defining an expansion chamber in fluid communication with the at least one fenestration of the intermediate body; and the longitudinal axis of the proximal body, the longitudinal axis of the intermediate body and the longitudinal axis of the distal body aligned substantially coaxial with one another.

8. A method for supporting the spine, comprising:

providing an implantable spinal mobility preservation apparatus having a intermediate body being substantially radially symmetrical about a longitudinal axis and having a proximal end and a distal end, the intermediate body including at least one flexible element positioned between the proximal and the distal end to increase the flexibility of the intermediate body, and the intermediate body defining at least one fenestration, a proximal body being substantially radially symmetrical about a longitudinal axis, the proximal body secured to the proximal end of the intermediate body, the proximal body including a first thread to rotatably position the proximal body through an axial bore in a body of a caudad vertebra, the proximal body defining a proximal lumen in fluid communication with the at least one fenestration of the intermediate body, a distal body being substantially radially symmetrical about a longitudinal axis, the distal body secured to the distal end of the intermediate body, the distal body including second thread to rotatably position the distal body through an axial bore in a body of a cephalad vertebra, and an expandable membrane having a substantially tubular shape, the expandable membrane secured over at least a portion of intermediate body which includes the at least one fenestration, the expandable membrane defining an expansion chamber in fluid communication with the at least one fenestration of the intermediate body;

forming an axial bore through a caudad vertebral body, an intervertebral disc and a cephalad vertebral body;

removing at least a portion of a nucleus pulposus of the intervertebral disc through the axial bore to form a disc space; and axially inserting the implantable spinal mobility preservation apparatus through the axial bore;

securing the distal body of the implantable mobility preservation apparatus in the cephalad vertebral body;

securing the proximal body of the implantable mobility preservation apparatus in the caudad vertebral body; and providing a prosthetic nucleus material through the proximal lumen into the expansion chamber of the spinal mobility preservation apparatus.

* * * * *